(12) United States Patent
Royal et al.

(10) Patent No.: US 10,501,632 B2
(45) Date of Patent: Dec. 10, 2019

(54) DIHYDROPYRENE DERIVATIVES, PROCESSES FOR PREPARING THE SAME AND THEIR USES

(71) Applicant: UNIVERSITE GRENOBLE ALPES, Saint Martin d'heres (FR)

(72) Inventors: Guy Royal, Cruet (FR); Saioa Cobo, Voreppe (FR); Eric Saint-Aman, Grenoble (FR); Veronique Josserand, La Tronche (FR); Didier Boturyn, La Buisse (FR)

(73) Assignee: Université GRENOBLE ALPES, Saint-Martin-d'Heres (FR)

( * ) Notice: Subject to any disclaimer, the term of this patent is extended or adjusted under 35 U.S.C. 154(b) by 0 days.

(21) Appl. No.: 15/577,784

(22) PCT Filed: Jun. 3, 2016

(86) PCT No.: PCT/EP2016/062715
§ 371 (c)(1),
(2) Date: Nov. 29, 2017

(87) PCT Pub. No.: WO2016/193471
PCT Pub. Date: Dec. 8, 2016

(65) Prior Publication Data
US 2018/0127586 A1   May 10, 2018

(30) Foreign Application Priority Data
Jun. 4, 2015 (WO) .................. PCT/IB2015/001934

(51) Int. Cl.
| | |
|---|---|
| *A61K 47/61* | (2017.01) |
| *C09B 57/00* | (2006.01) |
| *C07D 493/08* | (2006.01) |
| *C07D 213/06* | (2006.01) |
| *C07D 213/20* | (2006.01) |
| *A61K 47/54* | (2017.01) |
| *A61K 47/64* | (2017.01) |
| *A61P 35/04* | (2006.01) |
| *A61P 35/00* | (2006.01) |
| *A61K 41/00* | (2006.01) |
| *A61K 49/00* | (2006.01) |

(52) U.S. Cl.
CPC ........ *C09B 57/001* (2013.01); *A61K 41/0057* (2013.01); *A61K 47/545* (2017.08); *A61K 47/61* (2017.08); *A61K 47/64* (2017.08); *A61K 49/0015* (2013.01); *A61P 35/00* (2018.01); *A61P 35/04* (2018.01); *C07D 213/06* (2013.01); *C07D 213/20* (2013.01); *C07D 493/08* (2013.01)

(58) Field of Classification Search
USPC ........................................ 546/296
See application file for complete search history.

(56) References Cited

PUBLICATIONS

Roldan, Journal of the American Chemical Society (2013), 135(16), 5974-5977.*
Drebov, Zeitschrift fuer Naturforschung, B: Chemical Sciences (2005), 60(1), 75-82.*
Trabanco, Synlett 2000, No. 7, 1010-1012.*
Morita, J. Exp. Med., 1997 186 (10), 1997 1763-1768.*
Otsu, Cell Biology International 32 (2008) 1380-1387.*
Liu, ITE Letters on Batteries, New Technologies & Medicine (2001), 2(1), 98-101.*
Bak, Phytochemistry. 51 (7): 891-98.*
Nam Life Sciences. 69 (2): 229-37.*
Marriott, Pharmaceutical Compound and Dispensing, Second Edition, 2010, 1-288.*
Cerfontain, Liebigs Annalen/Recueil (1997), (5), 873-878.*
Diego Roldan et al.: "A Multi-Addressable Switch Based on the Dimethyldihydropyrene Photochrome with Remarkable Proton-Triggered Photo-opening Efficiency", Chemistry—A European Journal., vol. 21, No. 1, Oct. 30, 2014 (Oct. 30, 2014), Weinheim, DE, pp. 455-467, XP055231538, ISSN: 0947-6539, DOI: 10.1002/chem. 201404858.
Nedko Drebov et al.: "Photoswitching of Redox Potentials and Spectroscopic Properties in the UV/vis Region", Zeitschrift Für Naturforschung B, Jan. 1, 2005 (Jan. 1, 2005), pp. 75-82, XP055232753, Retrieved from the Internet <URL:http://www.znaturforsch.com/ab/v60b/s60b0075.pdf> [retrieved on Dec. 2, 2015], DOI: 10.1515/znb-2005-0112.
Assil Bakkar et al.: "A new surface-bound molecular switch based on the photochromic dimethyldihydropyrene with light-driven release of singlet oxygen properties", Journal of Materials Chemistry C: Materials for Optical and Electronic Devices, vol. 3, No. 46, Nov. 5, 2015 (Nov. 5, 2015), UK, pp. 12014-12017, XP055287319, ISSN: 2050-7526, DOI: 10.1039/C5TC02900G.
International Search Report, dated Jul. 21, 2016, from corresponding PCT/EP2016/062715 application.
International Search Report, dated Dec. 15, 2015, from corresponding PCT/IB2015/001934 application.

\* cited by examiner

*Primary Examiner* — Nizal S Chandrakumar
(74) *Attorney, Agent, or Firm* — Young & Thompson

(57) ABSTRACT

Disclosed are dihydropyrene derivatives, processes for preparing the same and their uses.

17 Claims, 4 Drawing Sheets

DIHYDROPYRENE DERIVATIVES, PROCESSES FOR PREPARING THE SAME AND THEIR USES

The present invention relates to dihydropyrene derivatives, processes for preparing the same and their uses.

Singlet oxygen ("active" oxygen) has many applications in different fields ranging from biology, therapy (cancer treatments, photodynamic therapy), imaging, to materials science (lithography . . . ).

Singlet oxygen can be obtained by irradiating the triplet oxygen in the presence of a photosensitizer, for example methylene blue.

However, $^1O_2$ is produced only during the irradiation process and it is difficult to control and regulate the amount of $^1O_2$ produced in order for example to limit nonspecific photodamages.

Another possibility is to release singlet oxygen by heating an endoperoxide compound which has been previously generated by irradiation in the presence of an additional photosensitizer. However, this method requires the use of an external photosensitizer.

More rarely, singlet oxygen is released by heating an endoperoxide compound that is directly generated by irradiation, but this irradiation is performed at relatively low wavelengths, said irradiation being therefore of high energy. But only low-energy radiation can pass through living tissues in depth.

One objective of the present invention is to provide a simple and effective system to store and produce singlet oxygen.

Another aim of the present invention is to provide a system for producing singlet oxygen in high yield.

Another aim of the present invention is to provide an easily tunable system, for example in terms of solubility.

Another aim of the present invention is to provide compounds forming endoperoxides without adding an external photosensitizer.

Another aim of the present invention is to provide compounds forming endoperoxides by irradiation of said compounds at high wavelengths, that is to say at low energy.

Another aim of the present invention is to provide endoperoxides capable of producing singlet oxygen, without the need to irradiate them, by thermal treatment, for example at 37° C., with regeneration of the original species.

Thus, the present invention relates to a compound of the following formula I

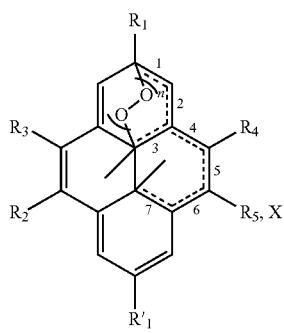

wherein:
n represents 0 or 1,
- - - - - - represents a single bond or no bond,
== represents a single or a double bond,
$R_1$ and $R'_1$ represent independently from each other:
H,
a linear or branched ($C_1$-$C_{18}$)-alkyl,
a ($C_3$-$C_8$)-cycloalkyl,

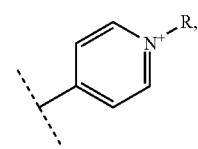

—$NR_3^+$,
R representing:
H,
a linear or branched ($C_1$-$C_{18}$)-alkyl,
a ($C_3$-$C_8$)-cycloalkyl,
$R_2$, $R_3$, $R_4$ and $R_5$ represent independently from each other:
H,
a linear or branched ($C_1$-$C_{18}$)-alkyl,
a ($C_3$-$C_8$)-cycloalkyl,

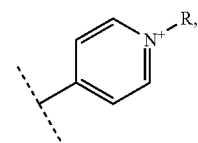

—$NR_3^+$,
R representing:
H,
a linear or branched ($C_1$-$C_{18}$)-alkyl,
a ($C_3$-$C_8$)-cycloalkyl,
X represents one or more physiologically acceptable counter anion(s),
providing that:
at least one of $R_1$, $R'_1$, $R_2$, $R_3$, $R_4$ and $R_5$ represents one of the following groups:

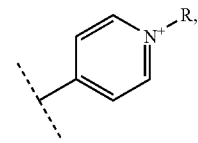

or
—$NR_3^+$,
n, - - - - - - - and the bonds 1 to 7 are such as:
n=0, - - - - - - represents a single bond, bonds 1, 4 and 6 represent a double bond, and bonds 2, 3, 5 and 7 represent a single bond, or
n=0, - - - - - - represents no bond, bonds 1, 3, 5 and 7 represent a double bond, and bonds 2, 4 and 6 represent a single bond, or
n=1, - - - - - - represents no bond, bonds 2, 5 and 7 represent a double bond, and bonds 1, 3, 4 and 6 represent a single bond,
for use in the treatment of pathologies sensitive to singlet oxygen, in particular for use in phototherapy and/or in the treatments of cancers, The term "linear or branched ($C_1$-$C_{18}$)-alkyl" denotes a straight or branched chain hydrocarbon group with 1 to 18 carbon groups, in particular with 1 to 6 carbon atoms. Examples of such groups are methyl, ethyl, propyl, isopropyl, butyl, isobutyl, sec-butyl, tert-butyl, pentyl, isopentyl, neopentyl, tert-pentyl, hexyl, isohexyl, 1,1-dimethylbutyl, 2,2-dimethylbutyl, 3,3-dimethylbul and 2-ethylbutyl. The alkyl group may optionally be substituted by a cycloalkyl group as defined below.

The term "($C_3$-$C_8$)-cycloalkyl" represents a saturated cyclic hydrocarbon such as cyclopropyl, cyclobutyl, cyclopentyl, cyclohexyl, cycloheptyl and cyclooctyl. The cycloalkyl group may optionally be substituted by an alley group as defined above.

By "counter anion(s)" is meant one or more anion(s) that form a salt, i.e. the compound of formula (I), with one or more the following cation(s):

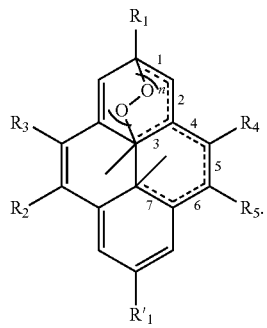

This structure is a cation, because at least one of $R_1$, $R'_1$, $R_2$, $R_3$, $R_4$ and $R_5$ represents one of the following groups:

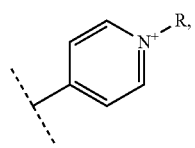

or
—$NR_3^+$.

If this structure is for example a monocation, X is in particular a monoanion, such as Cl⁻.

If this structure is for example a dication, X represents in particular two monoanions such as 2Cl⁻, or one dianion such as maleate.

By "physiologically acceptable" is meant that counter anions are suitable for ingestion by humans or animals, or for contact with the skin, mucous membranes and/or integuments, without any untoward physiological response, commensurate with a reasonable benefit/risk ratio.

Physiologically acceptable anions are in particular chosen from the group constituted by acetate $CH_3COO^-$, benzenesulfonate, benzoate, bicarbonate, bisulfate, bitartrate, borate, bromide Br⁻, camsylate, carbonate, chloride Cl⁻, clavulanate, citrate, dihydrochloride, edislyate, estolate, esylate, ethylsuccinate, fumarate, fluoride F⁻, gluceptate, gluconate, glutamate, glycollylarsanilate, hexafluorophosphate $PF_6^-$, hexylresorcinate, hydrabamine, iodide, isothionate, lactate, lactobionate, laurate, malate, maleate, mandelate, mesylate, methylsulfate, mutate, napsylate, nitrate, oleate, oxalate, pamoate (embonate), palimitate, pantothenate, phosphate, hydrogen phosphate $HPO_4^{2-}$, dihydrogen phosphate $H_2PO_4^-$, diphosphate, polygalacturonate, salicylate, stearate, subacetate, succinate, sulfate $SO_4^{2-}$, hydrogen sulfate $HSO_4^-$, tannate, tartrate, teoclate, tetrafluoroborate $BF_4^-$, tosylate, triethiodode, and valerate.

By "pathologies sensitive to singlet oxygen" is meant pathologies known to be treated by killing cells.

By phototherapy is meant a treatment that combines the use of light and of a photosensitizing product.

Examples of pathologies sensitive to singlet oxygen are cancers and other pathologies such as dysplasias, papillomas, rheumatoid arthritis, actinic keratosis, psoriasis, macular degeneration, atherosclerotic plaques, restenosis, coronary artery disease, central serous chorioretinopathy, myopic maculopathy, acne vulgaris, Barrett's esophagus, precancerous skin lesions including actinic keratosis, dysplastic nevi, dysplasia.

Examples of cancers are skin cancer, in particular melanoma or non-melanoma skin cancer, solid tumors in skin, basal cell carcinomas, cutaneous T-cell lymphoma, malignant skin and mucosa tumors, lung cancer, endobronchial lung cancer, bladder cancer, renal cell cancer, prostate cancer, liver cancer, esophagus cancer, pancreas cancer, bone carcinomas, breast cancer, brain tumor, in particular glioblastoma, head cancer, neck cancer, ocular melanoma, Kaposi's sarcoma, intraperitoneal cancer, cholangiocarcinoma, penile cancer, gliomas, colorectal cancer, gastric cancer, leucoplakia and gynecologic malignancies, such as tumors of the vagina, vulva and cervix, ovarian cancer.

In an advantageous embodiment, the present invention relates to a compound as described above, of the following formula I-1,2

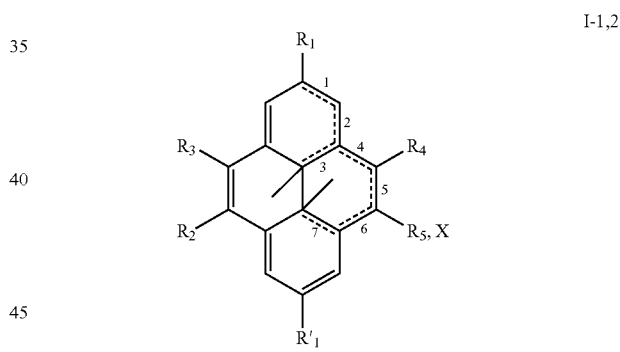

I-1,2 wherein:
- - - - - - - represents a single bond or no bond,
═ represents a single or a double bond,
$R_1$ and $R'_1$ represent independently from each other:
H,
a linear or branched ($C_1$-$C_{18}$)-alkyl,
a ($C_3$-$C_8$)-cycloalkyl,

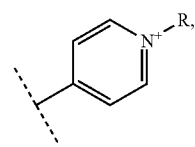

—$NR_3^+$,
R representing:
—H,
a linear or branched ($C_1$-$C_{18}$)-alkyl, a ($C_3$-$C_8$)-cycloalkyl,
$R_2$, $R_3$, $R_4$ and $R_5$ represent independently from each other:
H,
a linear or branched ($C_1$-$C_{18}$)-alkyl,
a ($C_3$-$C_8$)-cycloalkyl,

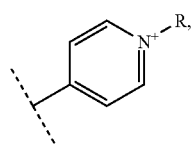

—$NR_3^+$,
R representing:
H,
a linear or branched ($C_1$-$C_{18}$)-alkyl,
a ($C_3$-$C_8$)-cycloalkyl,
X represents one or more physiologically acceptable counter anion(s),
providing that:
at least one of $R_1$, $R'_1$, $R_2$, $R_3$, $R_4$ and $R_5$ represents one of the following groups:

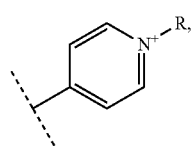

or
—$R_3^+$,
- - - - - - and the bonds 1 to 7 are such as:
- - - - - - - represents a single bond, bonds 1, 4 and 6 represent a double bond, and bonds 2, 3, 5 and 7 represent a single bond, or
- - - - - represents no bond, bonds 1, 3, 5 and 7 represent a double bond, and bonds 2, 4 and 6 represent a single bond, for use in the treatment of pathologies sensitive to singlet oxygen, in particular for use in phototherapy, more particularly in the treatments of cancers.

In an advantageous embodiment, the present invention relates to a compound as described above, of the following formula I-1

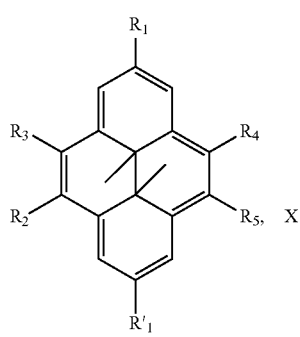

I-1 wherein:
$R_1$ and $R'_1$ represent independently from each other:
H,
a linear or branched ($C_1$-$C_{18}$)-alkyl,
a ($C_3$-$C_8$)-cycloalkyl,

—$NR_3^+$,
R representing:
H,
a linear or branched ($C_1$-$C_{18}$)-alkyl,
a ($C_3$-$C_8$)-cycloalkyl,
$R_2$, $R_3$, $R_4$ and $R_5$ represent independently from each other:
H,
a linear or branched ($C_1$-$C_{18}$)-alkyl,
a ($C_3$-$C_8$)-cycloalkyl,

—$NR_3^+$,
R representing:
H,
a linear or branched ($C_1$-$C_{18}$)-alkyl,
a ($C_3$-$C_8$)-cycloalkyl,
X represents one or more physiologically acceptable counter anion(s),
providing that:
at least one of $R_1$, $R'_1$, $R_2$, $R_3$, $R_4$ and $R_5$ represents one of the following groups:

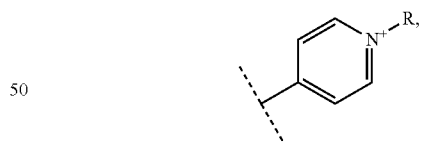

or
—$NR_3^+$,
for use in the treatment of pathologies sensitive to singlet oxygen, in particular for use in phototherapy, more particularly in the treatments of cancers.

Interestingly, the Inventors have found that compounds of formula I-1 are able to form endoperoxides without adding an external photosensitizes, by irradiation of said compounds at high wavelengths, that is to say at low energy.

Compounds of formula I-1 are non toxic,

In an advantageous embodiment, the present invention relates to a compound as described above, of the following formula I-2

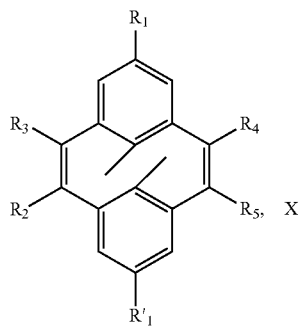

wherein:
$R_1$ and $R'_1$ represent independently from each other:
H,
a linear or branched ($C_1$-$C_{18}$-alkyl,
a ($C_3$-$C_8$)-cycloalkyl,

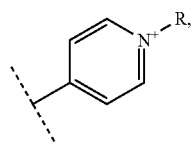

—$NR_3^+$,
R representing:
H,
a linear or branched ($C_1$-$C_{18}$)-alkyl,
a ($C_3$-$C_8$)-cycloalkyl,
$R_2$, $R_3$, $R_4$ and $R_5$ represent independently from each other:
H,
a linear or branched ($C_1$-$C_{18}$)-alkyl,
a ($C_3$-$C_8$)-cycloalkyl,

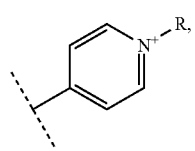

—$NR_3^+$,
R representing:
H,
a linear or branched ($C_1$-$C_{18}$)-alkyl,
a ($C_3$-$C_8$)-cycloalkyl,
X represents one or more physiologically acceptable counter anion(s),
providing that:
at least one of $R_1$, $R'_1$, $R_2$, $R_3$, $R_4$ and $R_5$ represents one of the following groups:

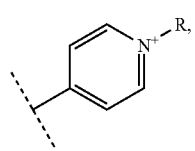

or
—$NR_3^+$,
for use in the treatment of pathologies sensitive to singlet oxygen, in particular for use in phototherapy, more particularly in the treatments of cancers.

In an advantageous embodiment, the present invention relates to a compound of the following formula I-3

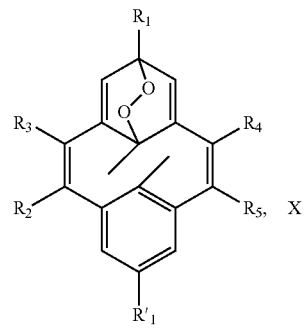

wherein:
$R_1$ and $R'_1$ represent independently from each other:
H,
a linear or branched ($C_1$-$C_{18}$)-alkyl,
a ($C_3$-$C_8$)-cycloalkyl,

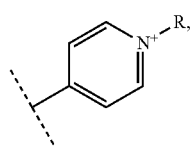

—$NR_3^+$,
R representing:
H,
a linear or branched ($C_1$-$C_{18}$)-alkyl,
a ($C_3$-$C_8$)-cycloalkyl,
$R_2$, $R_3$, $R_4$ and $R_5$ represent independently from each other:
H,
a linear or branched ($C_1$-$C_{18}$)-alkyl,
a ($C_3$-$C_8$)-cycloalkyl,

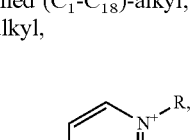

—$NR_3^+$,
R representing:
H,
a linear or branched ($C_1$-$C_{18}$)-alkyl,
a ($C_3$-$C_8$)-cycloalkyl,
X represents one or more physiologically acceptable counter anion(s),
providing that:
at least one of $R_1$, $R'_1$, $R_2$, $R_3$, $R_4$ and $R_5$ represents one of the following groups:

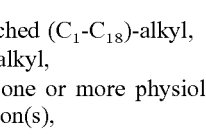

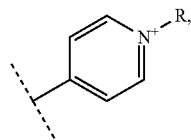

or
—$R_3^+$, for use in the treatment of pathologies sensitive to singlet oxygen, in particular for use in the treatments of cancers.

Interestingly, the Inventors have found that compounds of formula I-3 are able to produce singlet oxygen in high yield, without the need to irradiate them, by thermal treatment, for example at 37° C., and with regeneration of the compound I-1.

In an advantageous embodiment, the present invention relates to a compound for use as described above, wherein $R_1$ and $R'_1$ are identical.

In an advantageous embodiment, the present invention relates to a compound for use as described above, wherein $R_1$ and/or $R'_1$ represent(s) a linear or branched ($C_1$-$C_{18}$)-alkyl, in particular a tert-butyl.

The tert-butyl group increases the solubility of the compound. In particular the tet-butyl group avoids the precipitation of the compound during its synthesis and the insolubility of the resulting compound of the invention preventing its use. The tert-butyl group is also useful to protect the $R_1$ and/or $R'_1$ positions along the synthesis and especially during the functionalization steps of the dihydropyrene core.

In an advantageous embodiment, the present invention relates to a compound for use as described above, wherein $R_2$ and/or $R_4$ represent(s)

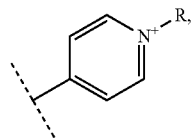

$R_3$ and $R_5$ representing in particular H.

In an advantageous embodiment, the present invention relates to a compound for use as described above, wherein $R_2$ represents

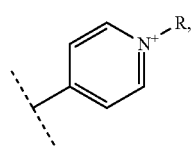

$R_3$, $R_4$ and $R_5$ representing in particular H.

In an advantageous embodiment, the present invention relates to a compound for use as described above, wherein $R_4$ represents

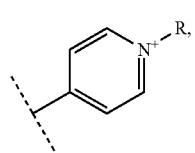

$R_2$, $R_3$ and $R_5$ representing in particular H.

In an advantageous embodiment, the present invention relates to a compound for use as described above, wherein $R_2$ and $R_4$ represent

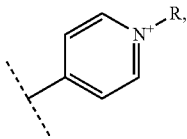

$R_3$ and $R_5$ representing in particular H.

In an advantageous embodiment, the present invention relates to a compound for use as described above, wherein $R_3$ and/or $R_5$ represent(s)

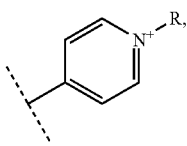

$R_2$ and $R_4$ representing in particular H.

In an advantageous embodiment, the present invention relates to a compound for use as described above, wherein $R_3$ represents

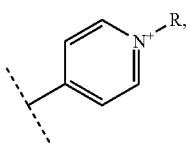

$R_2$, $R_4$ and $R_5$ representing in particular H.

In an advantageous embodiment, the present invention relates to a compound for use as described above, wherein $R_5$ represents

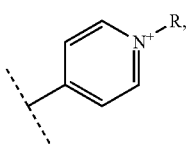

$R_2$, $R_3$ and $R_4$ representing in particular H.

In an advantageous embodiment, the present invention relates to a compound for use as described above, wherein $R_3$ and $R_5$ represent

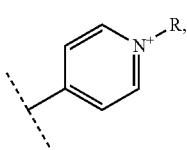

$R_2$ and $R_4$ representing in particular H.

In an advantageous embodiment, the present invention relates to a compound for use as described above, wherein X is (are) chosen from the group consisting in $Cl^-$, $PF_6^-$, $BF_4^-$, $CH_3COO^-$, $Br^-$, $F^-$, $SO_4^{2-}$, $HSO_4^-$, $HPO_4^{2-}$, $H_2PO_4^-$.

In an advantageous embodiment, the present invention relates to a compound for use as described above, wherein R represents a linear or branched ($C_1$-$C_{18}$)-alkyl, in particular —$CH_3$.

In another advantageous embodiment, the present invention relates to a compound for use as described above, wherein the compound of formula I forms a complex of formula II with a vectorization fragment R'.

By "complex" is meant an entity comprising a compound of formula I covalently bound to a vectorization fragment R'. In an advantageous embodiment, the vectorization fragment is covalently bound to the compound of formula I through the nitrogen atom bearing the R atom when the compound of formula I is not forming a complex of formula II. In any case, only one vectorization fragment is present on a complex of formula II.

By "vectorization fragment" is meant a group capable of transporting the entire compound to which it is attached into the cell. The vectorization fragment called R' is, in particular, an A-B fragment comprising an A group and a B group, the A group being a linker and the B group being chosen from a peptide or an acid residue selected from a hyaluronic acid or a folic acid. Said A group is a linker aiming at covalently linking the compound of formula I to the B group. Said B group is a targeting moiety enabling the guiding of the compound of formula I to a tumor, and the crossing of the cell membrane by said compound of formula I. The B group is specifically targeting the overexpressed receptors on tumor cells.

The A group, is a linker comprising a X-Peptide1-Y group wherein

X is any chemical group known from the man skilled in the art to bind an organic molecule to a peptide and in particular, X is a ($C_1$-$C_{18}$)-alkyl functionalized by an amino acid residue, preferably, X is a hexyl group bound to a cysteine derivative through a disulfide bridge;

Y is any chemical group known from the man skilled in the art to bind two peptides and in particular, Y is chosen from a group as described in the FR 02 11614 patent; preferably, Y is the chemical group of the following formula:

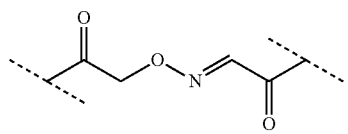

Peptide 1 is a peptide selected from a grafted homodetic cyclopeptide as described in the FR 02 11614 patent. A "homodetic cyclopeptide" refers to a cyclic peptide in which the ring consists solely of amino acid residues in eupeptide linkage. These homodetic cyclopeptides forms two faces, an upper face and a lower face, which are both grafted with molecules of interest, provided that the molecules of interest on each face are different.

Advantageously, the cyclopeptide is constituted from 5, 10 or 14 amino acid residues, preferably 10 amino acids forming a cyclodecapeptide. The cyclopeptide cyclized exhibits at least one turn, preferably two turns. Some cyclopeptides exhibit a central symmetry. According to another aspect, the cyclopeptide has 10 or 14 amino acid residues and forms two turns, each turn being constituted of an (L)Pro-(D)AA or (D)Pro-(L)AA combination, AA being an amino acid, and preferably glycine, the two turns being separated by three and/or five amino acid residues, these amino acid residues being identical or different. The presence of the proline residue at the turn is justified by the fact that because of its cyclic structure, proline has a characteristic spatial configuration as compared to other amino acids. This characteristic imposes a conformational restriction on the peptide skeleton as compared to that assumed with amino acids other than proline or its derivatives. This restriction is, in particular, the cause of the bends in the secondary and supersecondary polypeptide structures. The other amino acid residue of the turn, represented above by the symbol AA, is preferably an amino acid residue other than proline and having opposite stereochemistry, and very preferably the glycine residue. The turns are separated by amino acid residues, preferably an odd number of amino acid residues, and very preferably three and/or five amino acid residues for a cyclodecapeptide and a cyclotetradecapeptide, respectively. The two-turn cyclopeptides having an even number of amino acid residues exhibit a median plane that defines the upper face and the lower face. The three and/or five amino acid residues preferably each have a chemical function on their side chain. The chemical function of the side chains of these amino acids are directed alternately to one side and the other of the median plane of the framework, and define the lower and upper face with respect to that plane.

Advantageously, the A group is of the following formula:

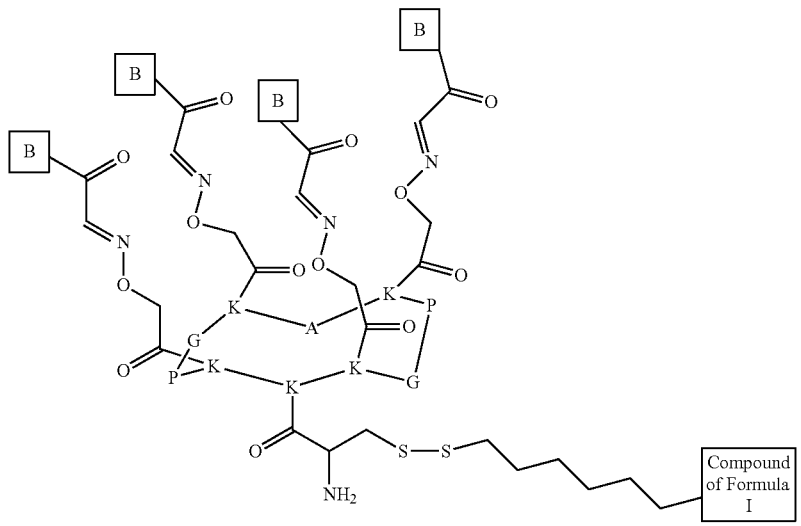

The B group is chosen from a peptide or an acid residue selected from a hyaluronic acid or a folic acid. Particularly, when B is a peptide, this peptide is called peptide2 and is selected from the peptides targeting the EGFR (Epidermal Growth Factor Receptor) and other receptors such as ATWLPPR, GE11, NGR . . . . In particular peptide2 is formed by five amino acid residues. The amino acids used are of any kind, including (D) series amino acids, (L) series amino acids, and any modified amino acid, the amino acids being natural or synthetic. Particularly, peptide2 is cyclic. Preferably peptide2 is cyclic and is formed by five amino acid residues. More preferably peptide2 is a cyclic peptide of the following formula:

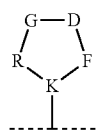

In one embodiment, the vectorization fragment is on one of the $R_1$, $R'_1$, $R_2$, $R_3$, $R_4$ and $R_5$ substituent of the complex of formula II and bound through the nitrogen of a pyridyl group. The vectorization fragment is therefore present on one position only of the complex of formula II.

In an advantageous embodiment, the present invention relates to a complex of formula II for use as described above, wherein $R_1$ or $R'_1$ represents

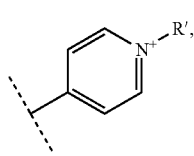

$R_2$, $R_3$, $R_4$ and $R_5$ representing in particular H.

In an advantageous embodiment, the present invention relates to a complex of formula II for use as described above, wherein $R_1$ represents

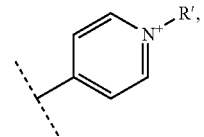

$R'_1$ representing a linear or branched $(C_1$-$C_{18})$-alkyl, in particular a tert-butyl, and $R_2$, $R_3$, $R_4$ and $R_5$ representing in particular H.

In an advantageous embodiment, the present invention relates to a complex of formula II for use as described above, wherein $R'_1$ represents

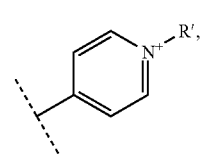

$R_1$ representing a linear or branched $(C_1$-$C_{18})$-alkyl, in particular a tert-butyl, and $R_2$, $R_3$, $R_4$ and $R_5$ representing in particular H.

In an advantageous embodiment, the present invention relates to a complex of formula II for use as described above, wherein $R_2$ or $R_4$ represent(s)

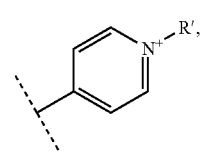

$R_3$ and $R_5$ representing in particular H.

In an advantageous embodiment, the present invention relates to a complex of formula II for use as described above, wherein $R_2$ represents

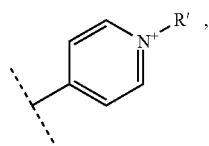

$R_3$, $R_4$ and $R_5$ representing in particular H.

In an advantageous embodiment, the present invention relates to a complex of formula II for use as described above, wherein $R_4$ represents

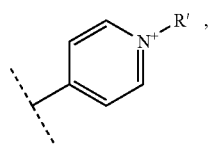

$R_2$, $R_3$ and $R_5$ representing in particular H.

In an advantageous embodiment, the present invention relates to a complex of formula II for use as described above, wherein $R_3$ or $R_5$ represent(s)

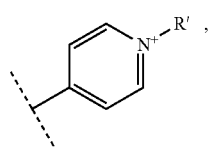

$R_2$, $R_3$ and $R_4$ representing in particular H.

In an advantageous embodiment, the present invention relates to a complex of formula II for use as described above, wherein $R_3$ represents

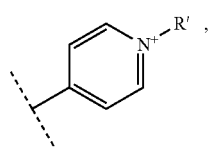

$R_2$, $R_4$ and $R_5$ representing in particular H.

In an advantageous embodiment, the present invention relates to a complex of formula II for use as described above, wherein $R_5$ represents

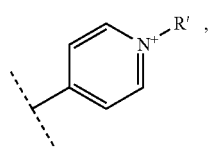

$R_2$, $R_3$ and $R_4$ representing in particular H.

In another advantageous embodiment, the present invention relates to a compound for use as described above, wherein the compound of formula I-1 forms a complex of formula II-1 with a vectorization fragment R'.

In an advantageous embodiment, the present invention relates to a complex of formula II-1 for use as described above, wherein $R_1$ or $R'_1$ represents

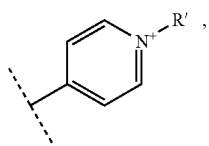

$R_2$, $R_3$, $R_4$ and $R_5$ representing in particular H.

In an advantageous embodiment, the present invention relates to a complex of formula II-1 for use as described above, wherein $R_1$ represents

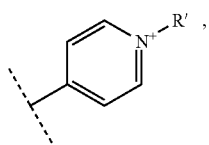

$R'_1$ representing a linear or branched $(C_1$-$C_{18})$-alkyl, in particular a tert-butyl, and $R_2$, $R_3$, $R_4$ and $R_5$ representing in particular H.

In an advantageous embodiment, the present invention relates to a complex of formula II-1 for use as described above, wherein $R'_1$ represents

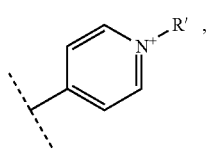

$R_1$ representing a linear or branched $(C_1$-$C_{18})$-alkyl, in particular a tert-butyl, and $R_2$, $R_3$, $R_4$ and $R_5$ representing in particular H.

In an advantageous embodiment, the present invention relates to a complex of formula II-1 for use as described above, wherein $R_2$ or $R_4$ represent(s)

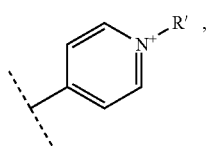

$R_3$ and $R_5$ representing in particular H.

In an advantageous embodiment, the present invention relates to a complex of formula II-1 for use as described above, wherein $R_2$ represents

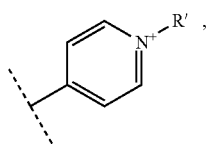

$R_3$, $R_4$ and $R_5$ representing in particular H.

In an advantageous embodiment, the present invention relates to a complex of formula II-1 for use as described above, wherein $R_4$ represents

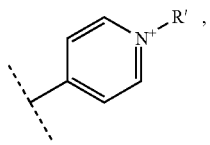

$R_2$, $R_3$ and $R_5$ representing in particular H.

In an advantageous embodiment, the present invention relates to a complex of formula II-1 for use as described above, wherein $R_3$ or $R_5$ represent(s)

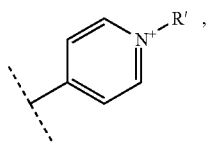

$R_2$ and $R_4$ representing in particular H.

In an advantageous embodiment, the present invention relates to a complex of formula II-4 for use as described above, wherein $R_3$ represents

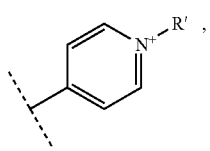

$R_2$, $R_4$ and $R_5$ representing in particular H.

In an advantageous embodiment, the present invention relates to a complex of formula II-1 for use as described above, wherein $R_5$ represents

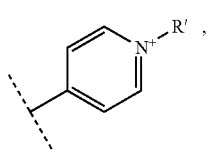

$R_2$, $R_3$ and $R_4$ representing in particular H.

In another advantageous embodiment, the present invention relates to a compound for use as described above, wherein the compound of formula I-2 forms a complex of formula II-2 with a vectorization fragment R'.

In an advantageous embodiment, the present invention relates to a complex of formula II-2 for use as described above, wherein $R_1$ or $R'_1$ represents

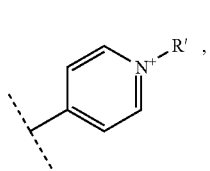

$R_2$, $R_3$, $R_4$ and $R_5$ representing in particular H.

In an advantageous embodiment, the present invention relates to a complex of formula II-2 for use as described above, wherein $R_1$ represents

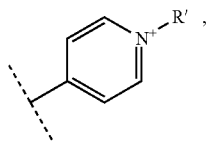

$R'_1$ representing a linear or branched $(C_1-C_{18})$-alkyl, in particular a tert-butyl, and $R_2$, $R_3$, $R_4$ and $R_5$ representing in particular H.

In an advantageous embodiment, the present invention relates to a complex of formula II-2 for use as described above, wherein $R'_1$ represents

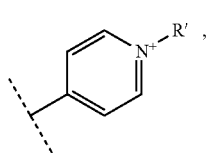

$R_1$ representing a linear or branched $(C_1-C_{18})$-alkyl, in particular a tert-butyl, and $R_2$, $R_3$, $R_4$ and $R_5$ representing in particular H.

In an advantageous embodiment, the present invention relates to a complex of formula II-2 for use as described above, wherein $R_2$ or $R_4$ represent(s)

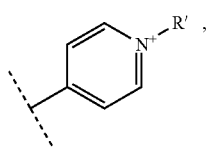

$R_3$ and $R_5$ representing in particular H.

In an advantageous embodiment, the present invention relates to a complex of formula II-2 for use as described above, wherein $R_2$ represents

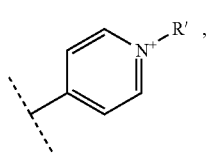

$R_3$, $R_4$ and $R_5$ representing in particular H.

In an advantageous embodiment, the present invention relates to a complex of formula II-2 for use as described above, wherein $R_4$ represents

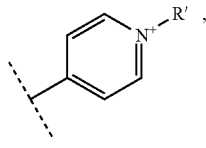

$R_2$, $R_3$ and $R_5$ representing in particular H.

In an advantageous embodiment, the present invention relates to a complex of formula II-2 for use as described above, wherein $R_3$ or $R_5$ represent(s)

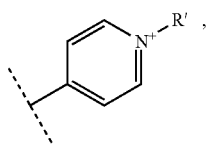

$R_2$ and $R_4$ representing in particular H.

In an advantageous embodiment, the present invention relates to a complex of formula II-2 for use as described above, wherein $R_3$ represents

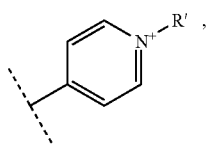

$R_2$, $R_4$ and $R_5$ representing in particular H.

In an advantageous embodiment, the present invention relates to a complex of formula II-2 for use as described above, wherein $R_5$ represents

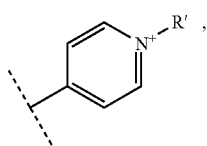

$R_2$, $R_3$ and $R_4$ representing in particular H.

In another advantageous embodiment, the present invention relates to a compound for use as described above, wherein the compound of formula I-3 forms a complex of formula II-3 with a vectorization fragment R'.

In an advantageous embodiment, the present invention relates to a complex of formula II-3 for use as described above, wherein $R_1$ or $R'_1$ represent(s)

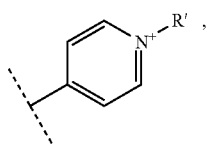

$R_2$, $R_3$, $R_4$ and $R_5$ representing in particular H.

In an advantageous embodiment, the present invention relates to a complex of formula II-3 for use as described above, wherein $R_1$ represents

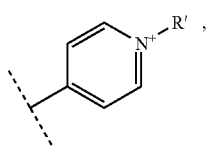

$R'_1$ representing a linear or branched $(C_1$-$C_{18})$-alkyl, in particular a tert-butyl, and $R_2$, $R_3$, $R_4$ and $R_5$ representing in particular H.

In an advantageous embodiment, the present invention relates to a complex of formula II-3 for use as described above, wherein $R'_1$ represents

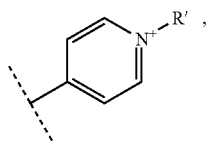

$R_1$ representing a linear or branched $(C_1$-$C_{18})$-alkyl, in particular a tert-butyl, and $R_2$, $R_3$, $R_4$ and $R_5$ representing in particular H.

In an advantageous embodiment, the present invention relates to a complex of formula II-3 for use as described above, wherein $R_2$ or $R_4$ represent(s)

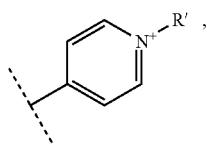

$R_3$ and $R_5$ representing in particular H.

In an advantageous embodiment, the present invention relates to a complex of formula II-3 for use as described above, wherein $R_2$ represents

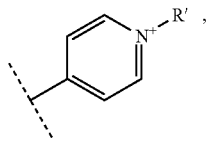

$R_3$, $R_4$ and $R_5$ representing in particular H.

In an advantageous embodiment, the present invention relates to a complex of formula II-3 for use as described above, wherein $R_4$ represents

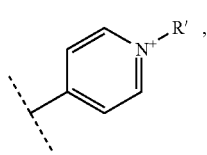

$R_2$, $R_3$ and $R_5$ representing in particular H.

In an advantageous embodiment, the present invention relates to a complex of formula II-3 for use as described above, wherein $R_3$ or $R_5$ represent(s)

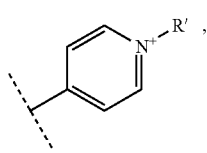

$R_2$ and $R_4$ representing in particular H.

In an advantageous embodiment, the present invention relates to a complex of formula II-3 for use as described above, wherein $R_3$ represents

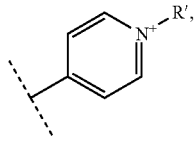

$R_2$, $R_4$ and $R_5$ representing in particular H.

In an advantageous embodiment, the present invention relates to a complex of formula II-3 for use as described above, wherein $R_5$ represents

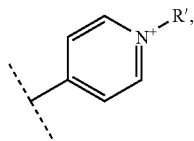

$R_2$, $R_3$ and $R_4$ representing in particular H.

In an advantageous embodiment, the present invention relates to a compound for use as described above, wherein the compound of formula I forms a complex of formula II with a vectorization fragment R', wherein R' is a A-B fragment, said A comprising a homodetic cyclopeptide and said B being a peptide.

The A-B fragment is on one of the $R_1$, $R'_1$, $R_2$, $R_3$, $R_4$ and $R_5$ substituent of the complex of formula II and bound through the nitrogen of a pyridyl group. The A-B fragment is therefore present on one position only of the complex of formula II.

In a preferred embodiment, the present invention relates to a compound for use as described above, wherein the compound of formula I forms a complex of formula II with a vectorization fragment R', wherein R' is a A-B fragment of the following formula:

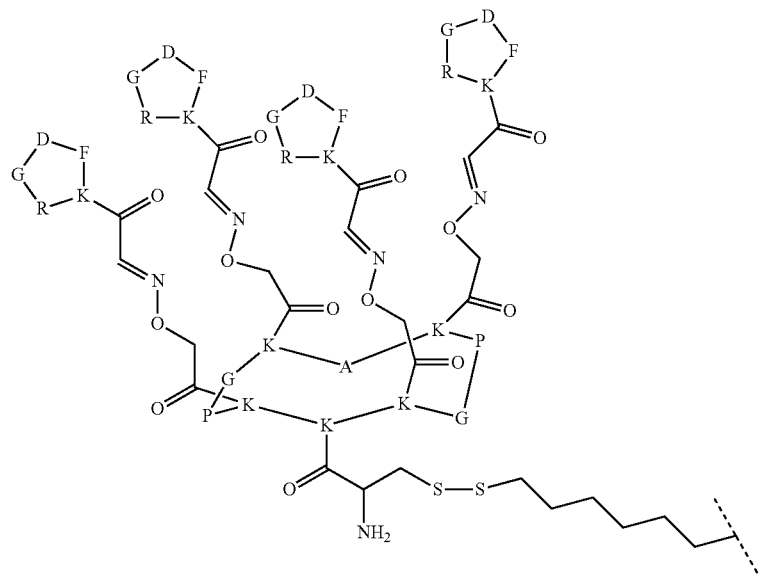

In an advantageous embodiment, the present invention relates to a compound for use as described above, wherein the compound of formula I forms a complex of formula II with a vectorization fragment R';

in particular said vectorization fragment R' being covalently bound to the compound of formula I through the nitrogen atom bearing the R atom when the compound of formula I is not forming a complex of formula II;

said vectorization fragment R' being, in particular, an A-B fragment comprising an A group and a B group;

said A group being more particularly comprising a X-Peptide1-Y, said A group being preferably of the following formula:

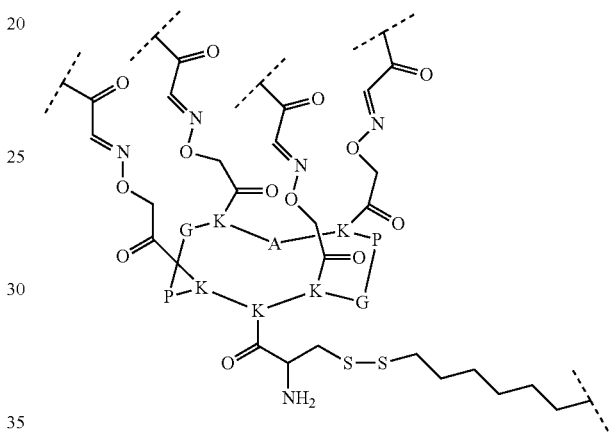

said B group being more particularly chosen from a peptide or an acid residue selected from a hyaluronic acid or a folic acid, said B group being preferably a peptide of the following formula:

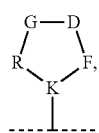
In an advantageous embodiment, the present invention relates to a compound for use as described above, of one of the following formulae:
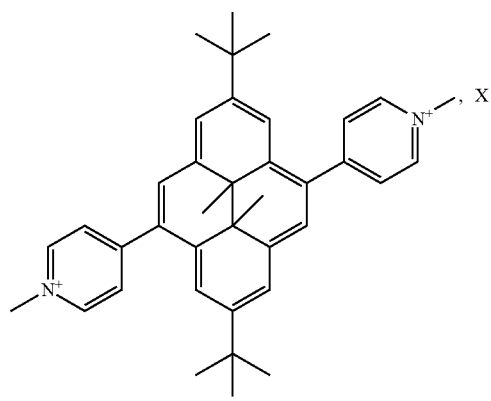
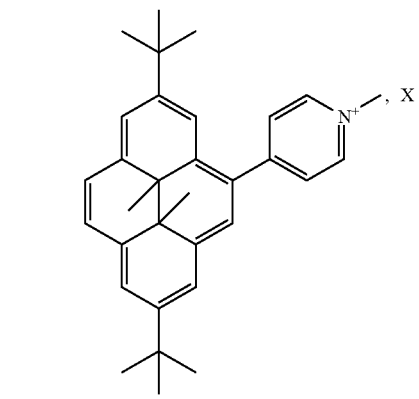
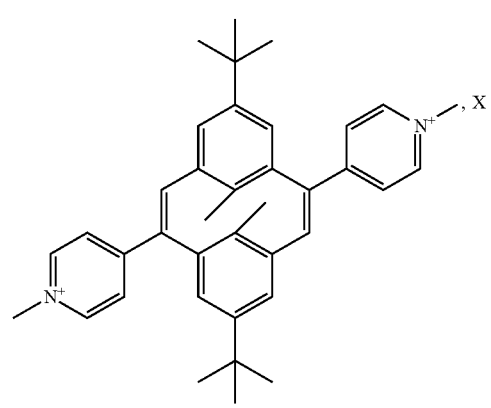
-continued
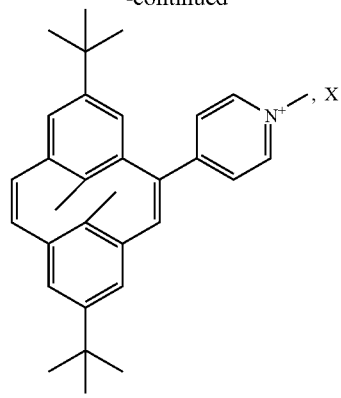
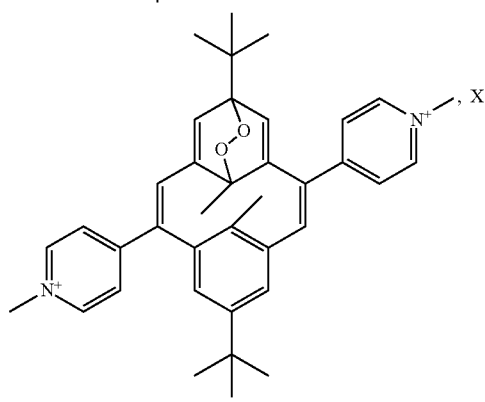
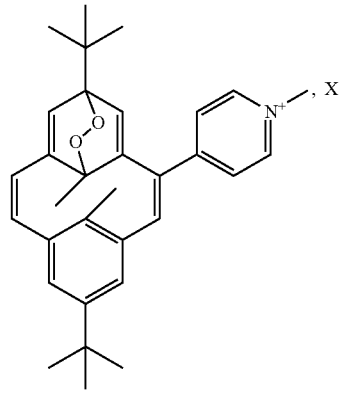
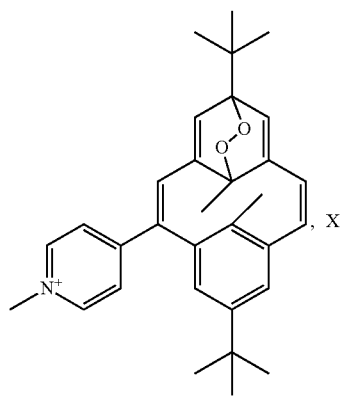
In an advantageous embodiment, the present invention relates to a compound for use as described above, forming a complex of one of the following formulae:

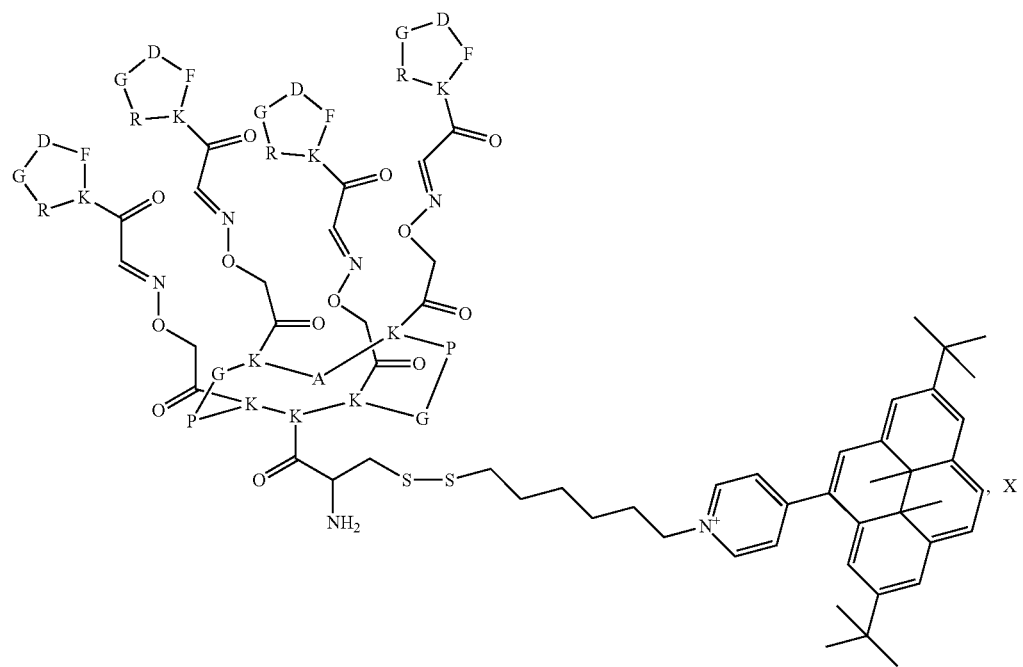
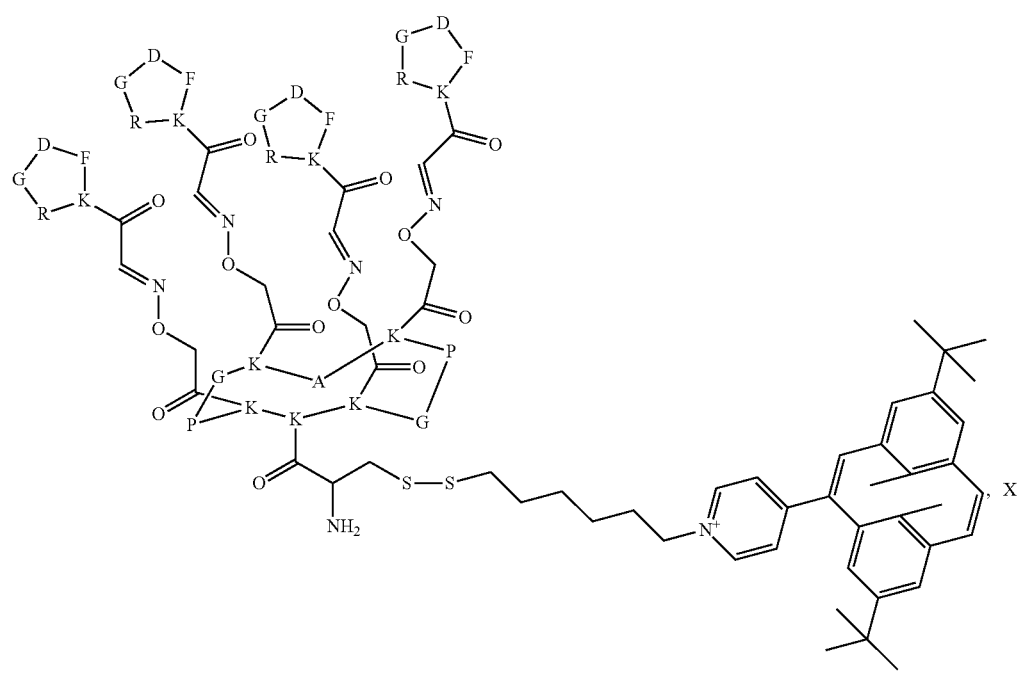

-continued

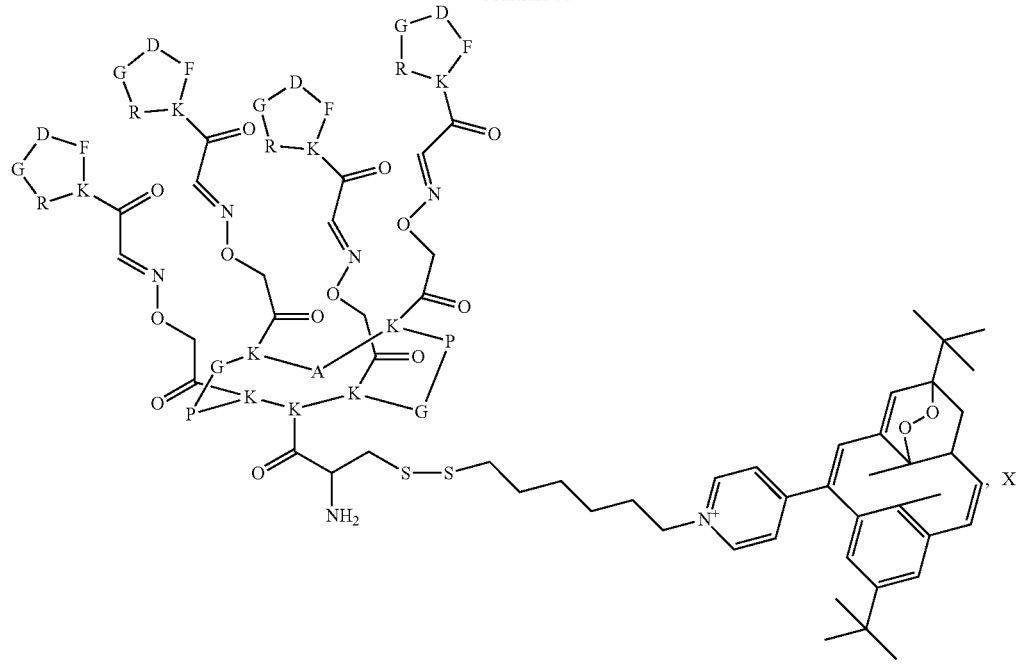

In another aspect, the present invention relates to a compound as defined above, for use in medical imaging.

In another aspect, the present invention relates to a complex as defined above, for use in medical imaging.

Compounds or complexes of the invention are bright fluorophores. Closed forms (compounds of formula I-1 or complexes of formula II-1) are fluorescent. Upon excitation, they emit visible light and can be observed in biologic media. The open and oxygenated forms are not luminescent.

Said compounds or complexes tend to emit in the 700-800 nm region, portion of the spectra that is useful for in vivo imaging. Such compounds are beneficial for aiding in defining and adjusting parameters prior to or during treatment of a patient, in particular photodynamic therapy. If the tissue, in particular the malignant tissue, retains the compounds or the complexes of the invention, the target site will light up to provide visible guidelines for therapy.

In another aspect, the present invention relates to a pharmaceutical composition comprising a compound of formula I as described above as active agent and a pharmaceutically acceptable vehicle.

In another aspect, the present invention relates to a pharmaceutical composition comprising a complex of formula II as described above as active agent and a pharmaceutically acceptable vehicle.

In another aspect, the present invention relates to a diagnostic composition comprising a compound of formula I as described above as active agent and a pharmaceutically acceptable vehicle.

In another aspect, the present invention relates to a diagnostic composition comprising a complex of formula II as described above as active agent and a pharmaceutically acceptable vehicle.

The expression "pharmaceutically acceptable vehicle" denotes in particular cellulose, starch, benzyl alcohol, polyethylene glycol, gelatin, lactose, polysorbate, magnesium or calcium stearate, xanthan gum, guar, alginate, colloidal silica.

The compositions according to the invention can be used by oral, parenteral, topic, or rectal route or in aerosols.

As solid compositions for oral administration, tablets, pills, gelatin capsules, powders or granules can be used. In these compositions, the active ingredient according to the invention is mixed with one or more inert diluents or adjuvants, such as saccharose, lactose or starch. These compositions can comprise substances other than the diluents, for example a lubricant such as magnesium stearate or a coating intended for controlled release.

As liquid compositions for oral administration, pharmaceutically acceptable solutions, suspensions, emulsions, syrups and elixirs containing inert diluents such as water or paraffin oil can be used. These compositions can also comprise substances other than the diluents, for example wetting products, sweeteners or flavourings.

The compositions for parenteral administration can be sterile solutions or emulsions. As solvent or vehicle, water, propylene glycol, a polyethylene glycol, vegetable oils, in particular olive oil, injectable organic esters, for example ethyl oleate can be used. These compositions can also contain adjuvants, in particular wetting agents, isotoning agents, emulsifiers, dispersants and stabilizers.

The sterilization can be carried out in several ways, for example using a bacteriological filter, by irradiation or by heating. They can also be prepared in the form of sterile solid compositions which can be dissolved at the moment of use in sterile water or any other injectable sterile medium.

The compositions for topical administration can be for example creams, ointments, lotions or aerosols.

The compositions for rectal administration are suppositories or rectal capsules, which, in addition to the active ingredient, contain excipients such as cocoa butter, semisynthetic glycerides or polyethylene glycols.

The compositions can also be aerosols.

For use in the form of liquid aerosols, the compositions can be stable sterile solutions or solid compositions dissolved at the moment of use in pyrogen-free sterile water, in serum or any other pharmaceutically acceptable vehicle. For use in the form of dry aerosols intended to be directly inhaled, the active ingredient is finely divided and combined with a diluent or hydrosoluble solid vehicle, for example dextran, mannitol or lactose.

In an advantageous embodiment, the present invention relates to a pharmaceutical or diagnostic composition defined above, administrable at a dose comprised from about 5 µg/kg to about 50 mg/kg.

In an advantageous embodiment, the present invention relates to a pharmaceutical or diagnostic composition defined above, administrable at an unitary dose comprised from 0.1 mg to 1000 mg, in particular from 10 mg to 1,000 mg, in particular from 10 to 500 mg, in particular from 10 to 100 mg.

In an advantageous embodiment, the present invention relates to a pharmaceutical or diagnostic composition as defined above, wherein said compound is of formula I-1,2, I-1, I-2 or I-3.

In an advantageous embodiment, the present invention relates to a pharmaceutical or diagnostic composition as defined above, wherein said complex is of formula II, II-1, II-2 or II-3.

In an advantageous embodiment, the present invention relates to a pharmaceutical or diagnostic composition comprising a compound of formula I-3 as described above as active agent and a pharmaceutically acceptable vehicle.

In an advantageous embodiment, the present invention relates to a pharmaceutical or diagnostic composition comprising a complex of formula II-3 as described above as active agent and a pharmaceutically acceptable vehicle.

In an advantageous embodiment, the present invention relates to a pharmaceutical or diagnostic composition as defined above, wherein $R_1$ and $R'_1$ are identical.

In an advantageous embodiment, the present invention relates to a pharmaceutical or diagnostic composition as defined above, wherein $R_1$ and/or $R'_1$ represent(s) a linear or branched ($C_1$-$C_{18}$)-alkyl, in particular a tert-butyl.

In an advantageous embodiment, the present invention relates to a pharmaceutical or diagnostic composition as defined above, wherein $R_2$ and/or $R_4$ represent(s)

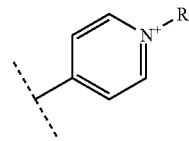

$R_3$ and $R_5$ representing in particular H.

In an advantageous embodiment, the present invention relates to a pharmaceutical or diagnostic composition as defined above, wherein $R_2$ represents

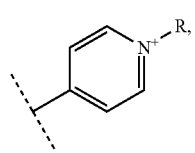

$R_3$, $R_4$ and $R_5$ representing in particular H.

In an advantageous embodiment, the present invention relates to a pharmaceutical or diagnostic composition as defined above, wherein $R_4$ represents

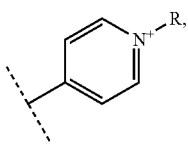

$R_2$, $R_3$ and $R_5$ representing in particular H.

In an advantageous embodiment, the present invention relates to a pharmaceutical or diagnostic composition as defined above, wherein $R_2$ and $R_4$ represent

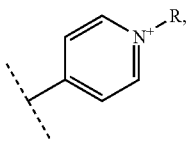

$R_3$ and $R_5$ representing in particular H.

In an advantageous embodiment, the present invention relates to a pharmaceutical or diagnostic composition as defined above, wherein $R_3$ and/or $R_5$ represent(s)

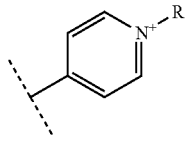

$R_2$ and $R_4$ representing in particular H.

In an advantageous embodiment, the present invention relates to a pharmaceutical or diagnostic composition as defined above, wherein $R_3$ represents

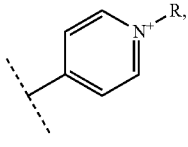

$R_2$, $R_4$ and $R_5$ representing in particular H.

In an advantageous embodiment, the present invention relates to a pharmaceutical or diagnostic composition as defined above, wherein $R_5$ represents

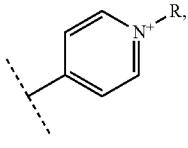

$R_2$, $R_3$ and $R_4$ representing in particular H.

In an advantageous embodiment, the present invention relates to a pharmaceutical or diagnostic composition as defined above, wherein $R_3$ and $R_5$ represent(s)

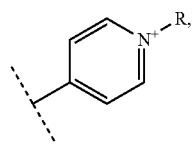

$R_2$ and $R_4$ representing in particular H.

In an advantageous embodiment, the present invention relates to a pharmaceutical or diagnostic composition as defined above.

In an advantageous embodiment, the present invention relates to a pharmaceutical or diagnostic composition as defined above, wherein X is (are) chosen from the group consisting in $Cl^-$, $PF_6^-$, $BF_4^-$, $CH_3COO^-$, $Br^-$, $F^-$, $SO_4^{2-}$, $HSO_4^-$, $HPO_4^{2-}$, $H_2PO_4^-$.

In an advantageous embodiment, the present invention relates to a pharmaceutical or diagnostic composition as defined above, wherein R represents a linear or branched $(C_1-C_{18})$-alkyl, in particular —$CH_3$.

In another advantageous embodiment, the present invention relates to a pharmaceutical or diagnostic composition as defined above, wherein the compound of formula I forms a complex of formula II with a vectorization fragment R'.

The vectorization fragment is on one of the $R_1$, $R'_1$, $R_2$, $R_3$, $R_4$ and $R_5$ substituent of the complex of formula II and bound through the nitrogen of a pyridyl group. The vectorization fragment is therefore present on one position only of the complex of formula II.

In an advantageous embodiment, the present invention relates to a pharmaceutical or diagnostic composition as defined above, wherein $R_1$ or $R'_1$ represent(s)

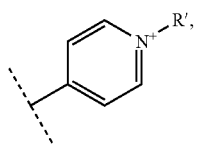

$R_2$, $R_3$, $R_4$ and $R_5$ representing in particular H.

In an advantageous embodiment, the present invention relates to a pharmaceutical or diagnostic composition as defined above, wherein $R_1$ represents

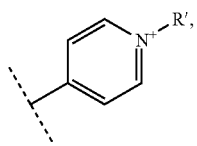

$R'_1$ representing a linear or branched $(C_1-C_{18})$-alkyl, in particular a tert-butyl, and $R_2$, $R_3$, $R_4$ and $R_5$ representing in particular H.

In an advantageous embodiment, the present invention relates to a pharmaceutical or diagnostic composition as defined above, wherein $R'_1$ represents

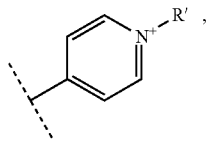

$R_1$ representing a linear or branched $(C_1-C_{18})$-alkyl, in particular a tert-butyl, and $R_2$, $R_3$, $R_4$ and $R_5$ representing in particular H.

In an advantageous embodiment, the present invention relates to a pharmaceutical or diagnostic composition as defined above, wherein $R_2$ or R represent(s)

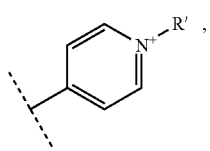

$R_3$ and $R_5$ representing in particular H.

In an advantageous embodiment, the present invention relates to a pharmaceutical or diagnostic composition as defined above, wherein $R_2$ represents

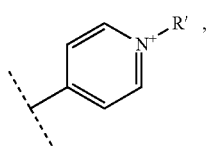

$R_3$, $R_4$ and $R_5$ representing in particular H.

In an advantageous embodiment, the present invention relates to a pharmaceutical or diagnostic composition as defined above, wherein $R_4$ represents

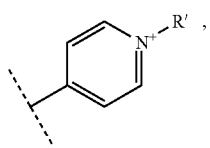

$R_2$, $R_3$ and $R_5$ representing in particular H.

In an advantageous embodiment, the present invention relates to a pharmaceutical or diagnostic composition as defined above, wherein $R_3$ or $R_5$ represent(s)

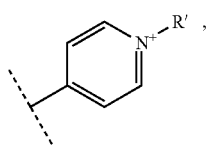

$R_2$ and $R_4$ representing in particular H.

In an advantageous embodiment, the present invention relates to a pharmaceutical or diagnostic composition as defined above, wherein $R_3$ represents

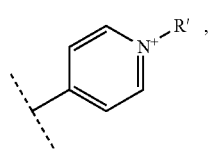

$R_2$, $R_4$ and $R_5$ representing in particular H.

In an advantageous embodiment, the present invention relates to a pharmaceutical or diagnostic composition as defined above, wherein $R_5$ represents

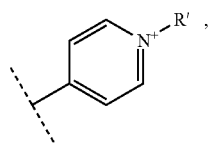

$R_2$, $R_3$ and $R_4$ representing in particular H.

In an advantageous embodiment, the present invention relates to a pharmaceutical or diagnostic composition as described above, wherein the compound of formula I forms a complex of formula II with a vectorization fragment R', wherein R' is a A-B fragment, said A comprising a homodetic cyclopeptide and said B being a peptide.

The A-B fragment is on one of the $R_1$, $R'_1$, $R_2$, $R_3$, $R_4$ and $R_5$ substituent of the complex of formula II and bound through the nitrogen of a pyridyl group. The A-B fragment is therefore present on one position only of the complex of formula II.

In a preferred embodiment, the present invention relates to a pharmaceutical or diagnostic composition as described above, wherein the compound of formula I forms a complex of formula II with a vectorization fragment R', wherein R' is a A-B fragment of the following formula:

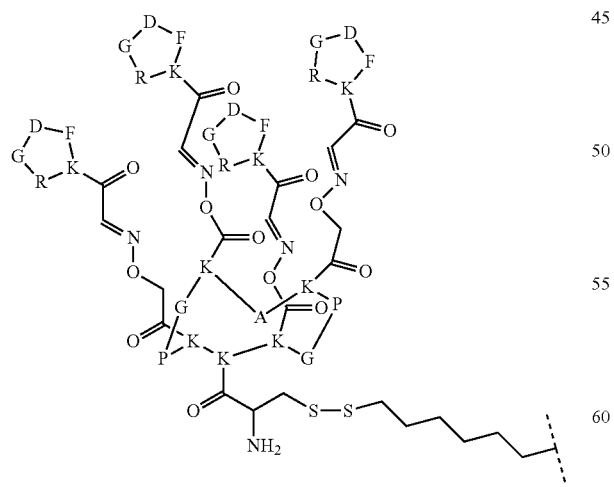

In an advantageous embodiment, the present invention relates to a pharmaceutical or diagnostic composition as defined above, of one of the following formulae:

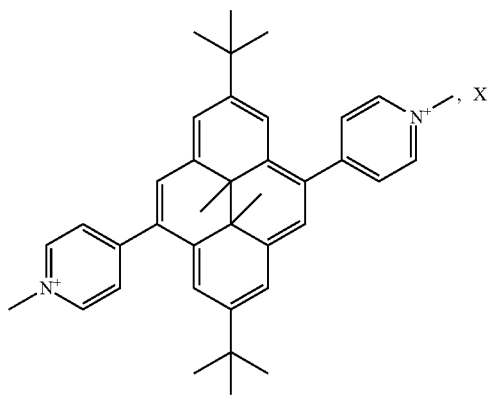

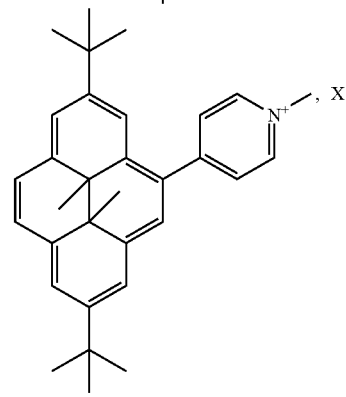

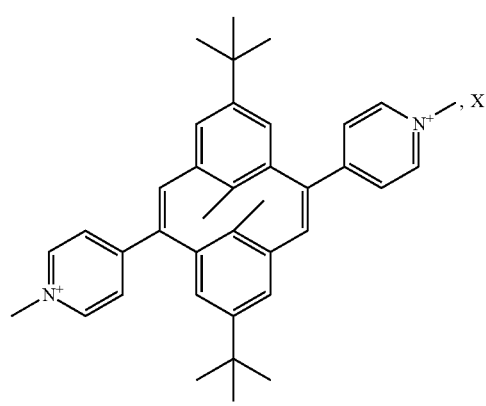

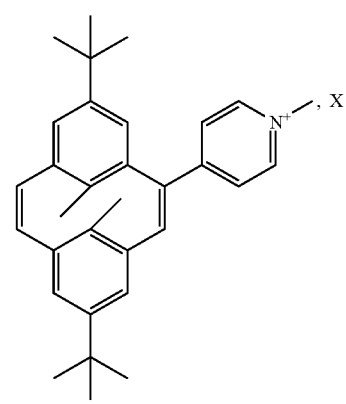

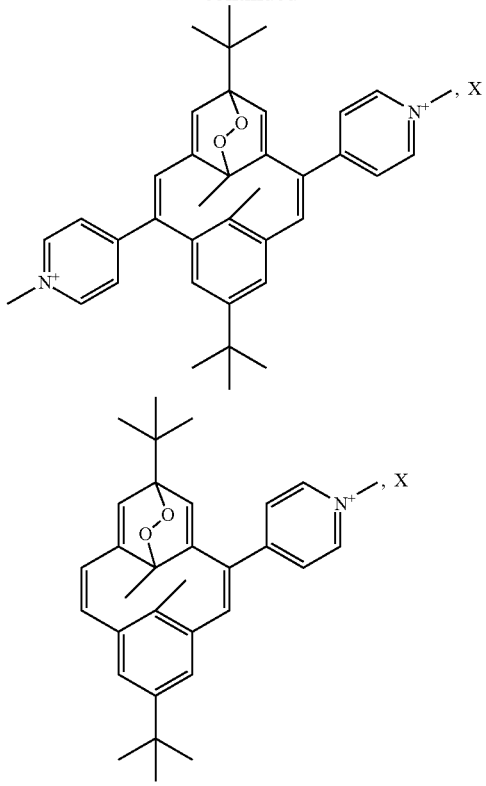
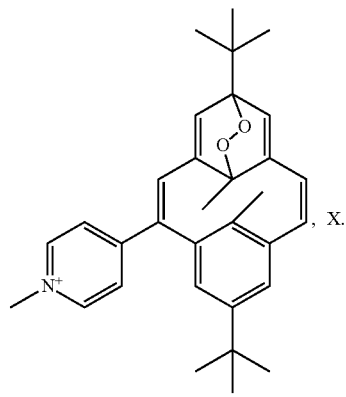
In an advantageous embodiment, the present invention relates to a pharmaceutical or diagnostic composition as defined above, wherein the compound of formula I forms a complex of formula II of one of the following formulae:
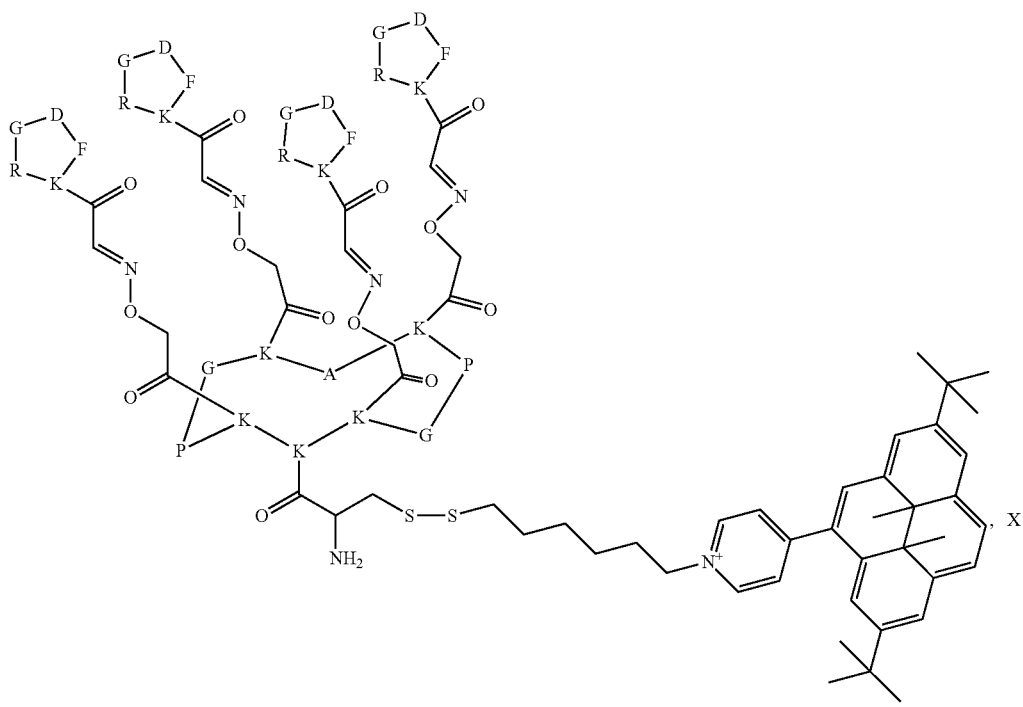

-continued
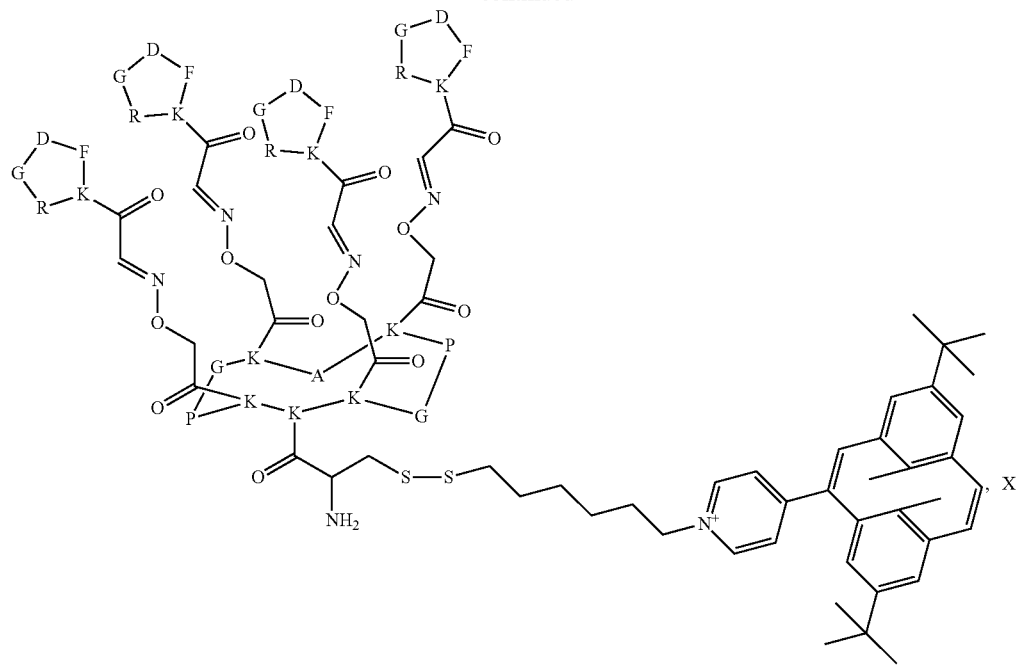
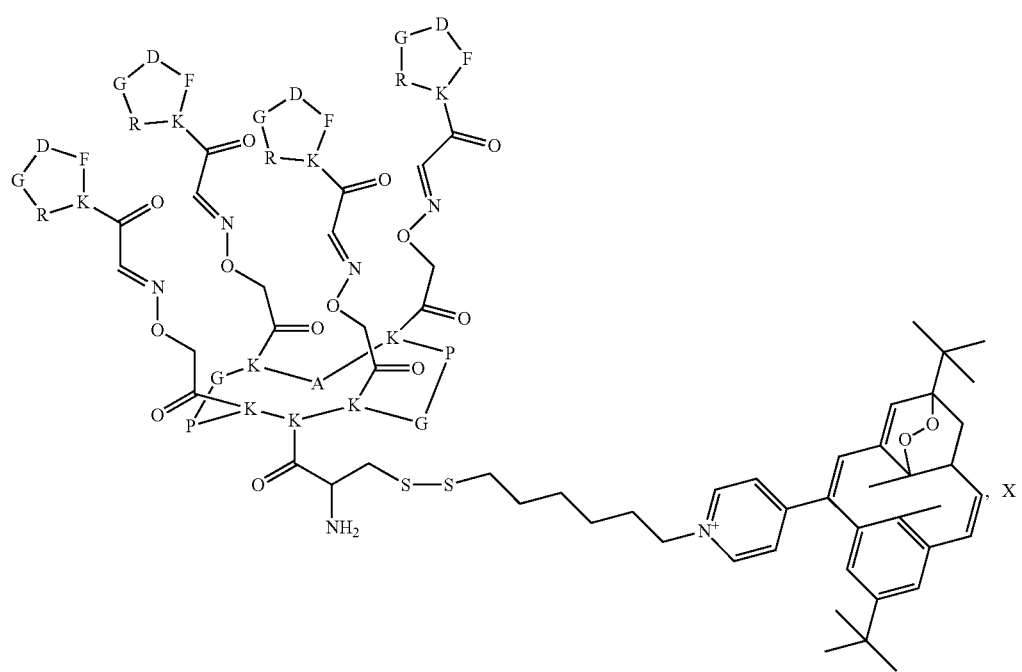

In another aspect, the present invention relates to a compound of the following formula I

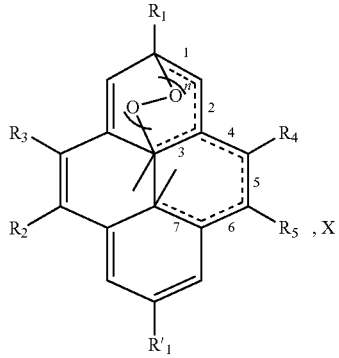

wherein:
n represents 0 or 1,
- - - - - - represents a single bond or no bond,
== represents a single or a double bond,
$R_1$ and $R'_1$ represent independently from each other:
H,
a linear or branched ($C_1$-$C_{18}$)-alkyl,
a ($C_3$-$C_8$)-cycloalkyl,

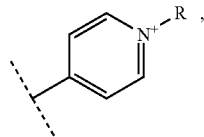

—$NR_3^+$,
R representing:
H,
a linear or branched ($C_1$-$C_{18}$)-alkyl,
a ($C_3$-$C_8$)-cycloalkyl,
$R_2$, $R_3$, $R_4$ and $R_5$ represent independently from each other:
H,
a linear or branched ($C_1$-$C_{18}$)-alkyl,
a ($C_3$-$C_8$)-cycloalkyl,

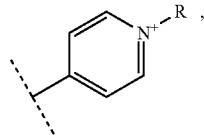

—$NR_3^+$,
R representing:
H,
a linear or branched ($C_1$-$C_{18}$)-alkyl,
a ($C_3$-$C_8$)-cycloalkyl,
X represents one or more counter anion(s), in particular one or more physiologically acceptable counter anion(s),
providing that:
at least one of $R_1$, $R'_1$, $R_2$, $R_3$, $R_4$ and $R_5$ represents one of the following groups:

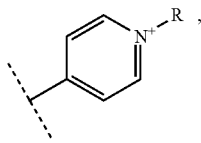

or
—$NR_3^+$,
n, - - - - - - - and the bonds 1 to 7 are such as:
  n=0, - - - - - - - represents a single bond, bonds 1, 4 and 6 represent a double bond, and bonds 2, 3, 5 and 7 represent a single bond, or
  n=0, - - - - - - - represents no bond, bonds 1, 3, 5 and 7 represent a double bond, and bonds 2, 4 and 6 represent a single bond, or
  n=1, - - - - - - - represents no bond, bonds 2, 5 and 7 represent a double bond, and bonds 1, 3, 4 and 6 represent a single bond.

In another aspect, the present invention relates to a compound of the following formula I(bis)

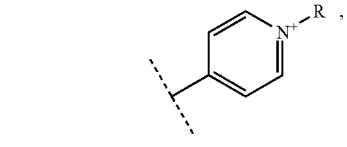

wherein:
n represents 0 or 1,
- - - - - - represents a single bond or no bond,
== represents a single or a double bond,
$R_1$ and $R'_1$ represent independently from each other:
H,
a linear or branched ($C_1$-$C_{18}$)-alkyl,
a ($C_3$-$C_8$)-cycloalkyl,

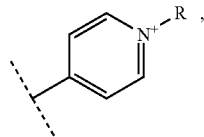

—$NR_3^+$,
R representing:
H,
a linear or branched ($C_1$-$C_{18}$)-alkyl,
a ($C_3$-$C_8$)-cycloalkyl,
$R_2$, $R_3$, $R_4$ and $R_5$ represent independently from each other:

H,
a linear or branched ($C_1$-$C_{18}$)-alkyl,
a ($C_3$-$C_8$)-cycloalkyl,

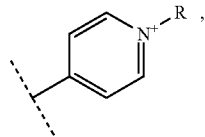

—$NR_3^+$,
R representing:
H,
a linear or branched ($C_1$-$C_{18}$)-alkyl,
a ($C_3$-$C_8$)-cycloalkyl,
   X represents one or more counter anion(s), in particular one or more physiologically acceptable counter anion(s),
providing that:
   at least one of $R_1$, $R'_1$, $R_2$, $R_3$, $R_4$ and $R_5$ represents one of the following groups:

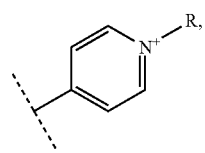

or
—$NR_3^+$,
n, - - - - - - and the bonds 1 to 7 are such as:
   n=0, - - - - - - represents a single bond, bonds 1, 4 and 6 represent a double bond, and bonds 2, 3, 5 and 7 represent a single bond, or
   n=0, - - - - - - represents no bond, bonds 1, 3, 5 and 7 represent a double bond, and bonds 2, 4 and 6 represent a single bond, or
   n=1, - - - - - - represents no bond, bonds 2, 5 and 7 represent a double bond, and bonds 1, 3, 4 and 6 represent a single bond,
when n=0, $R_1$ and/or $R'_1$ are different from one of the following groups:

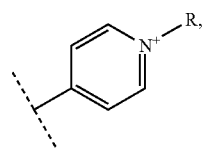

or
—$NR_3^+$.

In an advantageous embodiment, the present invention relates to a compound as defined above, of the following formula I-1,2

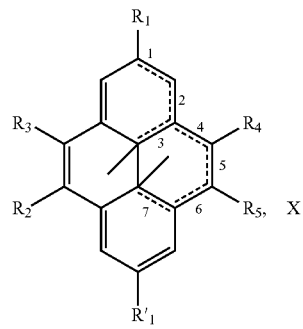

I-1,2 wherein:
   - - - - - - represents a single bond or no bond,
   = represents a single or a double bond,
   $R_1$ and $R'_1$ represent independently from each other:
   H,
   a linear or branched ($C_1$-$C_{18}$)-alkyl,
   a ($C_3$-$C_8$)-cycloalkyl,

—$NR_3^+$,
R representing:
   H,
   a linear or branched ($C_1$-$C_{18}$)-alkyl,
   a ($C_3$-$C_8$)-cycloalkyl,
   $R_2$, $R_3$, $R_4$ and $R_5$ represent independently from each other:
   H,
   a linear or branched ($C_1$-$C_{18}$)-alkyl,
   a ($C_3$-$C_8$)-cycloalkyl,

—$NR_3^+$,
R representing:
   H,
   a linear or branched ($C_1$-$C_{18}$)-alkyl,
   a ($C_3$-$C_8$)-cycloalkyl,
   X represents one or more physiologically acceptable counter anion(s), providing that:
at least one of $R_1$, $R'_1$, $R_2$, $R_3$, $R_4$ and $R_5$ represents one of the following groups:

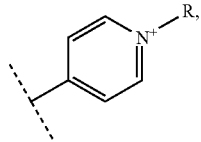

or
—$NR_3^+$,
 and the bonds 1 to 7 are such as:
- - - - - - represents a single bond, bonds 1, 4 and 6 represent a double bond, and bonds 2, 3, 5 and 7 represent a single bond, or
- - - - - - represents no bond, bonds 1, 3, 5 and 7 represent a double bond, and bonds 2, 4 and 6 represent a single bond.

In an advantageous embodiment, the present invention relates to a compound as defined above, of the following formula I(bis)-1,2

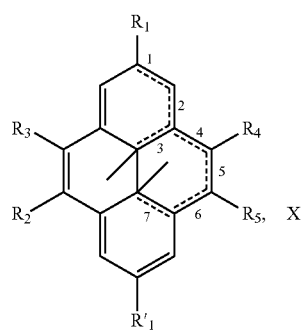

I(bis)-1,2 wherein:
- - - - - - represents a single bond or no bond,
═ represents a single or a double bond,
$R_1$ and $R'_1$ represent independently from each other:
H,
a linear or branched ($C_1$-$C_{18}$)-alkyl,
a ($C_3$-$C_5$)-cycloalkyl,
$R_2$, $R_3$, $R_4$ and $R_5$ represent independently from each other:
H,
a linear or branched ($C_1$-$C_{18}$)-alkyl,
a ($C_3$-$C_8$)-cycloalkyl,

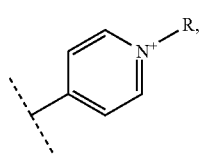

—$NR_3^+$,
R representing:
H,
a linear or branched ($C_1$-$C_{18}$)-alkyl,
a ($C_3$-$C_8$)-cycloalkyl, X represents one or more physiologically acceptable counter anion(s),
providing that:
at least one of $R_2$, $R_3$, $R_4$ and $R_5$ represents one of the following groups:

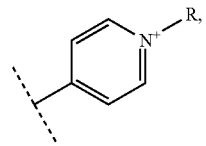

or
—$R_3^+$,
 and the bonds 1 to 7 are such as:
- - - - - - represents a single bond, bonds 1, 4 and 6 represent a double bond, and bonds 2, 3, 5 and 7 represent a single bond, or
- - - - - - represents no bond, bonds 1, 3, 5 and 7 represent a double bond, and bonds 2, 4 and 6 represent a single bond.

In an advantageous embodiment, the present invention relates to a compound as defined above, of the following formula I-1

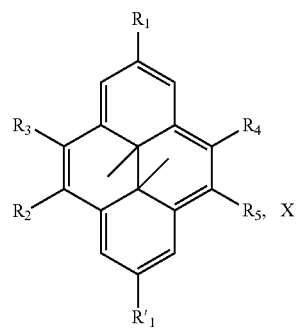

I-1 wherein:
$R_1$ and $R'_1$ represent independently from each other:
H,
a linear or branched ($C_1$-$C_{18}$)-alkyl,
a ($C_3$-$C_8$)-cycloalkyl,

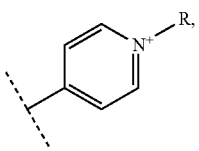

—$NR_3^+$,
R representing:
H,
a linear or branched ($C_1$-$C_{18}$)-alkyl,
a ($C_3$-$C_8$)-cycloalkyl,
$R_2$, $R_3$, $R_4$ and $R_5$ represent independently from each other:
H,
a linear or branched ($C_1$-$C_{18}$)-alkyl,
a ($C_3$-$C_8$)-cycloalkyl,

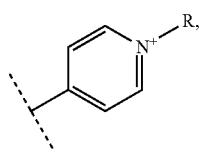

—NR$_3^+$,

R representing:
  H,
  a linear or branched (C$_1$-C$_{18}$)-alkyl,
  a (C$_3$-C$_8$)-cycloalkyl,
    X represents one or more counter anion(s), in particular one or more physiologically acceptable counter anion(s),
providing that:
  at least one of R$_1$, R'$_1$, R$_2$, R$_3$, R$_4$ and R$_5$ represents one of the following groups:

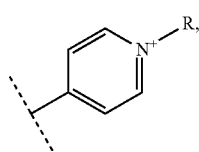

or
  —NR$_3^+$.

In an advantageous embodiment, the present invention relates to a compound as defined above, of the following formula I(bis)-1

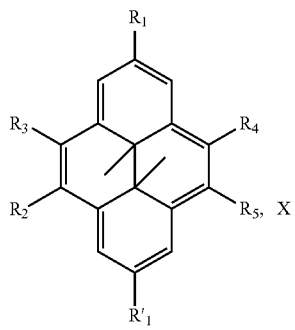

I(bis)-1 wherein:
  R$_1$ and R'$_1$ represent independently from each other:
  H,
  a linear or branched (C$_1$-C$_{18}$)-alkyl,
  a (C$_3$-C$_8$)-cycloalkyl,
    R$_2$, R$_3$, R$_4$ and R$_5$ represent independently from each other:
  H,
  a linear or branched (C$_1$-C$_{18}$)-alkyl,
  a (C$_3$-C$_8$)-cycloalkyl,

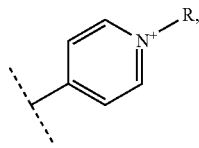

—NR$_3$,

R representing:
  H,
  a linear or branched (C$_1$-C$_{18}$)-alkyl,
  a (C$_3$-C$_8$)-cycloalkyl,
    X represents one or more counter anion(s), in particular one or more physiologically acceptable counter anion(s),
providing that:
  at least one of R$_2$, R$_3$, R$_4$ and R$_5$ represents one of the following groups:

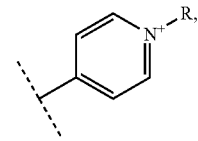

or
  —NR$_3^+$.

In an advantageous embodiment, the present invention relates to a compound as defined above, of the following formula I-2

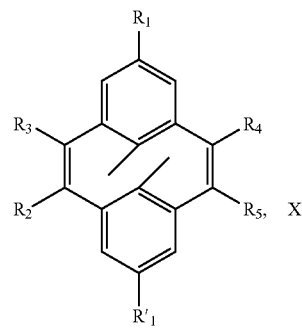

I-2 wherein:
  R$_1$ and R'$_1$ represent independently from each other:
  H,
  a linear or branched (C$_1$-C$_{18}$)-alkyl,
  a (C$_3$-C$_8$)-cycloalkyl,

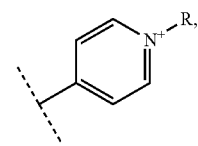

—NR$_3^+$,

R representing:
  H,
  a linear or branched (C$_1$-C$_{18}$)-alkyl,
  a (C$_3$-C$_8$)-cycloalkyl,
    R$_2$, R$_3$, R$_4$ and R$_5$ represent independently from each other:
  H,
  a linear or branched (C$_1$-C$_{18}$)-alkyl,
  a (C$_3$-C$_8$)-cycloalkyl,

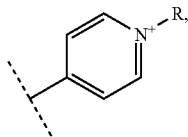

—NR$_3^+$,
R representing:
H,
a linear or branched (C$_1$-C$_{18}$)-alkyl,
a (C$_3$-C$_8$)-cycloalkyl,
X represents one or more counter anion(s), in particular one or more physiologically acceptable counter anion(s),
providing that:
at least one of R$_1$, R'$_1$, R$_2$, R$_3$, R$_4$ and R$_5$ represents one of the following groups:

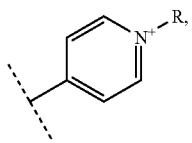

or
—NR$_3^+$,

In an advantageous embodiment, the present invention relates to a compound as defined above, of the following formula I(bis)-2

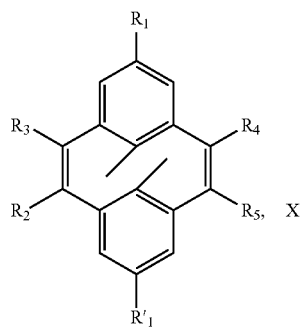

I(bis)-2 wherein:
R$_1$ and R'$_1$ represent independently from each other:
H,
a linear or branched (C$_1$-C$_{18}$)-alkyl,
a (C$_3$-C$_8$)-cycloalkyl,
R$_2$, R$_3$, R$_4$ and R$_5$ represent independently from each other:
H,
a linear or branched (C$_1$-C$_{18}$)-alkyl,
a (C$_3$-C$_8$)-cycloalkyl,

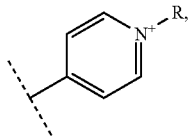

—NR$_3^+$,
R representing:
H,
a linear or branched (C$_1$-C$_{18}$)-alkyl,
a (C$_3$-C$_8$)-cycloalkyl,
X represents one or more counter anion(s), in particular one or more physiologically acceptable counter anion(s),
providing that:
at least one of R$_2$, R$_3$, R$_4$ and R$_5$ represents one of the following groups:

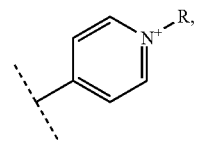

or
—NR$_3^+$.

In an advantageous embodiment, the present invention relates to a compound of the following formula I-3

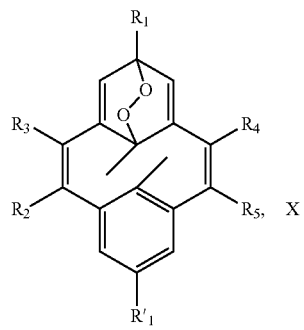

I-3 wherein:
R$_1$ and R'$_1$ represent independently from each other:
H,
a linear or branched (C$_1$-C$_{18}$)-alkyl,
a (C$_3$-C$_8$)-cycloalkyl,

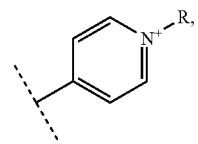

—NR$_3^+$,
R representing:
H,
a linear or branched (C$_1$-C$_{18}$)-alkyl,
a (C$_3$-C$_8$)-cycloalkyl,
R$_2$, R$_3$, R$_4$ and R$_5$ represent independently from each other:
H,
a linear or branched (C$_1$-C$_{18}$)-alkyl,
a (C$_3$-C$_8$)-cycloalkyl,

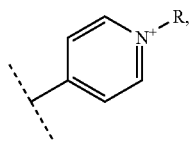

—NR$_3^+$,

R representing:
  H,
  a linear or branched (C$_1$-C$_{18}$)-alkyl,
  a (C$_3$-C$_8$)-cycloalkyl,
    X represents one or more counter anion(s), in particular one or more physiologically acceptable counter anion(s),
providing that:
  at least one of R$_1$, R'$_1$, R$_2$, R$_3$, R$_4$ and R$_5$ represents one of the following groups:

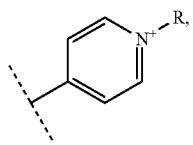

or
  —NR$_3^+$.

In an advantageous embodiment, the present invention relates to a compound as defined above, wherein R$_1$ and R'$_1$ are identical.

In an advantageous embodiment, the present invention relates to a compound as defined above, wherein R$_1$ and/or R'$_1$ represent(s) a linear or branched (C$_1$-C$_{18}$)-alkyl, in particular a tert-butyl.

In an advantageous embodiment, the present invention relates to a compound as defined above, wherein R$_2$ and/or R$_4$ represent(s)

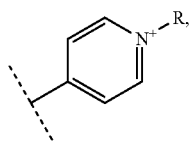

R$_3$ and R$_5$ representing in particular H.

In an advantageous embodiment, the present invention relates to a compound as defined above, wherein R$_3$ and/or R$_5$ represent(s)

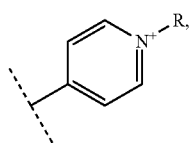

R$_2$ and R$_4$ representing in particular H.

In an advantageous embodiment, the present invention relates to a compound as defined above, wherein X is (are) chosen from the group consisting in Cl$^-$, PF$_6^-$, BF$_4^-$, CH$_3$COO$^-$, Br$^-$, F$^-$, SO$_4^{2-}$, HSO$_4^-$, HPO$_4^{2-}$, H$_2$PO$_4^-$.

In an advantageous embodiment, the present invention relates to a compound as defined above, wherein R represents a linear or branched (C$_1$-C$_{18}$)-alkyl, in particular —CH$_3$.

In another advantageous embodiment, the present invention relates to a compound as described above, wherein the compound of formula I forms a complex of formula II with a vectorization fragment R'.

In another advantageous embodiment, the present invention relates to a compound as described above, wherein the compound of formula I(bis) forms a complex of formula II with a vectorization fragment R'.

The vectorization fragment is on one of the R$_1$, R'$_1$, R$_2$, R$_3$, R$_4$ and R$_5$ substituent of the complex of formula II and bounded through the nitrogen of a pyridyl group. The vectorization fragment is therefore present on one position only of the complex of formula II.

In an advantageous embodiment, the present invention relates to a complex of formula II as defined above, wherein R$_1$ or R'$_1$ represent(s)

R$_2$, R$_3$, R$_4$ and R$_5$ representing in particular H.

In an advantageous embodiment, the present invention relates to a complex of formula II as defined above, wherein R$_1$ represents

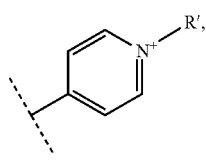

R'$_1$ representing a linear or branched (C$_1$-C$_{18}$)-alkyl, in particular a tert-butyl, and R$_2$, R$_3$, R$_4$ and R$_5$ representing in particular H.

In an advantageous embodiment, the present invention relates to a complex of formula II as defined above, wherein R'$_1$ represents

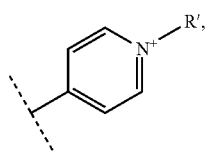

R$_1$ representing a linear or branched (C$_1$-C$_{18}$)-alkyl, in particular a tert-butyl, and R$_2$, R$_3$, R$_4$ and R$_5$ representing in particular H.

In an advantageous embodiment, the present invention relates to a complex of formula II as defined above, wherein R$_2$ or R$_4$ represent(s)

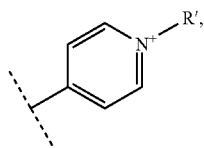

$R_3$ and $R_5$ representing in particular H.

In an advantageous embodiment, the present invention relates to a complex of formula II as defined above, wherein $R_2$ represents

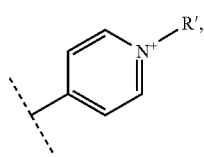

$R_3$, $R_4$ and $R_5$ representing in particular H.

In an advantageous embodiment, the present invention relates to a complex of formula II as defined above, wherein $R_4$ represents

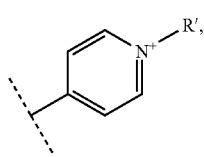

$R_2$, $R_3$ and $R_5$ representing in particular H.

In an advantageous embodiment, the present invention relates to a complex of formula II as defined above, wherein $R_3$ or $R_5$ represent(s)

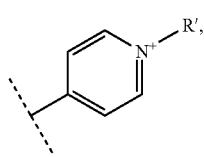

$R_2$ and $R_4$ representing in particular H.

In an advantageous embodiment, the present invention relates to a complex of formula II as defined above, wherein $R_3$ represents

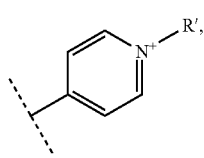

$R_2$, $R_4$ and $R_5$ representing in particular H.

In an advantageous embodiment, the present invention relates to a complex of formula II as defined above, wherein $R_5$ represents

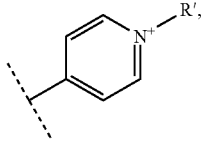

$R_2$, $R_3$ and $R_4$ representing in particular H.

In an advantageous embodiment, the present invention relates to a complex of formula II-1 as defined above, wherein $R_1$ or $R'_1$ represent(s)

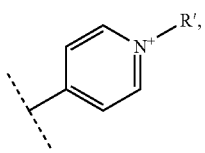

$R_2$, $R_3$, $R_4$ and $R_5$ representing in particular H.

In an advantageous embodiment, the present invention relates to a complex of formula II-1 as defined above, wherein $R_1$ represents

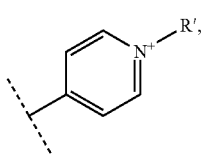

$R'_1$ representing a linear or branched $(C_1-C_{18})$-alkyl, in particular a tert-butyl, and $R_2$, $R_3$, $R_4$ and $R_5$ representing in particular H.

In an advantageous embodiment, the present invention relates to a complex of formula II-1 as defined above, wherein $R'_1$ represents

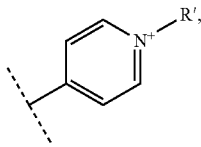

$R_1$ representing a linear or branched $(C_1-C_{18})$-alkyl, in particular a tert-butyl, and $R_2$, $R_3$, $R_4$ and $R_5$ representing in particular H.

In an advantageous embodiment, the present invention relates to a complex of formula II-1 as defined above, wherein $R_2$ or $R_4$ represent(s)

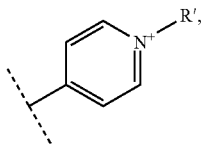

$R_3$ and $R_5$ representing in particular H.

In an advantageous embodiment, the present invention relates to a complex of formula II-1 as defined above, wherein $R_2$ represents

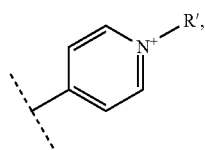

$R_3$, $R_4$ and $R_5$ representing in particular H.

In an advantageous embodiment, the present invention relates to a complex of formula II-1 as defined above, wherein $R_4$ represents

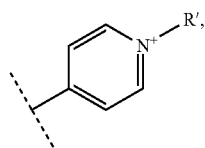

$R_2$, $R_3$ and $R_5$ representing in particular H.

In an advantageous embodiment, the present invention relates to a complex of formula II-1 as defined above, wherein $R_3$ or $R_5$ represent(s)

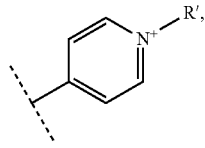

$R_2$ and $R_4$ representing in particular H.

In an advantageous embodiment, the present invention relates to a complex of formula II-1 as defined above, wherein $R_3$ represents

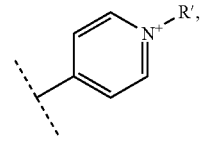

$R_2$, $R_4$ and $R_5$ representing in particular H.

In an advantageous embodiment, the present invention relates to a complex of formula II-1 as defined above, wherein $R_5$ represents

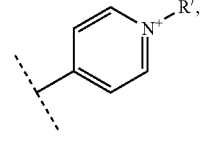

$R_2$, $R_3$ and $R_4$ representing in particular H.

In an advantageous embodiment, the present invention relates to a complex of formula II-2 as defined above, wherein $R_1$ or $R'_1$ represent(s)

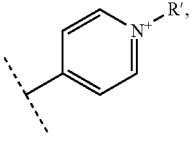

$R_2$, $R_3$, $R_4$ and $R_5$ representing in particular H.

In an advantageous embodiment, the present invention relates to a complex of formula II-2 as defined above, wherein $R_1$ represents

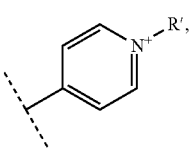

$R'_1$ representing a linear or branched $(C_1\text{-}C_{18})$-alkyl, in particular a tert-butyl, and $R_2$, $R_3$, $R_4$ and $R_5$ representing in particular H.

In an advantageous embodiment, the present invention relates to a complex of formula II-2 as defined above, wherein represents

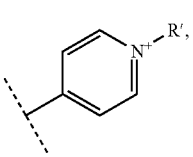

$R_1$ representing a linear or branched $(C_1\text{-}C_{18})$-alkyl, in particular a tert-butyl, and $R_2$, $R_3$, $R_4$ and $R_5$ representing in particular H.

In an advantageous embodiment, the present invention relates to a complex of formula II-2 as defined above, wherein $R_2$ or $R_4$ represent(s)

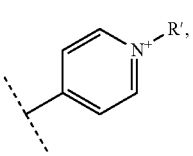

$R_3$ and $R_5$ representing in particular H.

In an advantageous embodiment, the present invention relates to a complex of formula II-2 as defined above, wherein $R_2$ represents

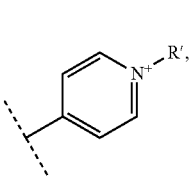

$R_3$, $R_4$ and $R_5$ representing in particular H.

In an advantageous embodiment, the present invention relates to a complex of formula II-2 as defined above, wherein $R_4$ represents

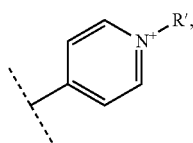

$R_2$, $R_3$ and $R_5$ representing in particular H.

In an advantageous embodiment, the present invention relates to a complex of formula II-2 as defined above, wherein $R_3$ or $R_5$ represent(s)

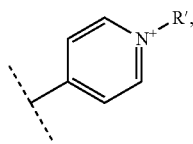

$R_2$ and $R_4$ representing in particular H.

In an advantageous embodiment, the present invention relates to a complex of formula II-2 as defined above, wherein $R_3$ represents

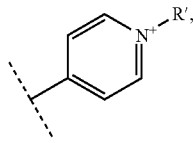

$R_2$, $R_4$ and $R_5$ representing in particular H.

In an advantageous embodiment, the present invention relates to a complex of formula II-2 as defined above, wherein $R_5$ represents

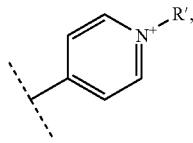

$R_2$, $R_3$ and $R_4$ representing in particular H.

In an advantageous embodiment, the present invention relates to a complex of formula II-3 as defined above, wherein $R_1$ or $R'_1$ represent(s)

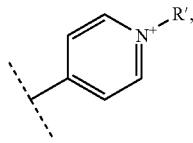

$R_2$, $R_3$, $R_4$ and $R_5$ representing in particular H.

In an advantageous embodiment, the present invention relates to a complex of formula II-3 as defined above, wherein $R_1$ represents

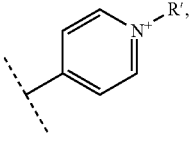

$R'_1$ representing a linear or branched $(C_1\text{-}C_{18})$-alkyl, in particular a tert-butyl, and $R_2$, $R_3$, $R_4$ and $R_5$ representing in particular H.

In an advantageous embodiment, the present invention relates to a complex of formula II-3 as defined above, wherein $R'_1$ represents

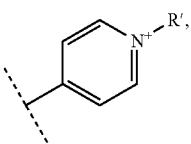

$R_1$ representing a linear or branched $(C_1\text{-}C_{18})$-alkyl, in particular a tert-butyl, and $R_2$, $R_3$, $R_4$ and $R_5$ representing in particular H.

In an advantageous embodiment, the present invention relates to a complex of formula II-3 as defined above, wherein $R_2$ or $R_4$ represent(s)

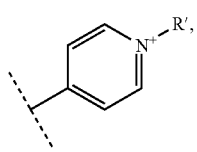

$R_3$ and $R_5$ representing in particular H.

In an advantageous embodiment, the present invention relates to a complex of formula II-3 as defined above, wherein $R_2$ represents

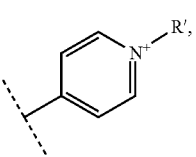

$R_3$, $R_4$ and $R_5$ representing in particular H.

In an advantageous embodiment, the present invention relates to a complex of formula II-3 as defined above, wherein $R_4$ represents

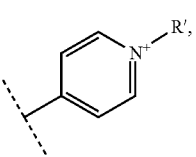

$R_2$, $R_3$ and $R_5$ representing in particular H.

In an advantageous embodiment, the present invention relates to a complex of formula II-3 as defined above, wherein $R_3$ or $R_5$ represent(s)

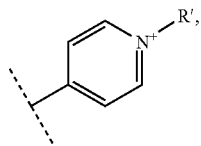

$R_2$ and $R_4$ representing in particular H.

In an advantageous embodiment, the present invention relates to a complex of formula II-3 as defined above, wherein $R_3$ represents

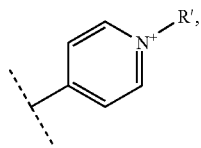

$R_2$, $R_4$ and $R_5$ representing in particular H.

In an advantageous embodiment, the present invention relates to a complex of formula II-3 as defined above, wherein $R_5$ represents

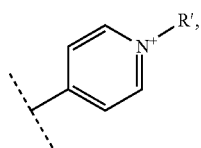

$R_2$, $R_3$ and $R_4$ representing in particular H.

In an advantageous embodiment, the present invention relates to a compound as described above, wherein the compound of formula I forms a complex of formula II with a vectorization fragment R', wherein R' is a A-B fragment, said A comprising a homodetic cyclopeptide and said B being a peptide.

In another advantageous embodiment, the present invention relates to a compound as described above, wherein the compound of formula I(bis) forms a complex of formula II with a vectorization fragment R', wherein R' is a A-B fragment, said A comprising a homodetic cyclopeptide and said B being a peptide.

The A-B fragment is on one of the $R_1$, $R'_1$, $R_2$, $R_3$, $R_4$ and $R_5$ substituent of the complex of formula II and bound through the nitrogen of a pyridyl group. The A-B fragment is therefore present on one position only of the complex of formula II.

In a preferred embodiment, the present invention relates to a compound as described above, wherein the compound of formula I forms a complex of formula II with a vectorization fragment R', wherein R' is a A-B fragment of the following formula:

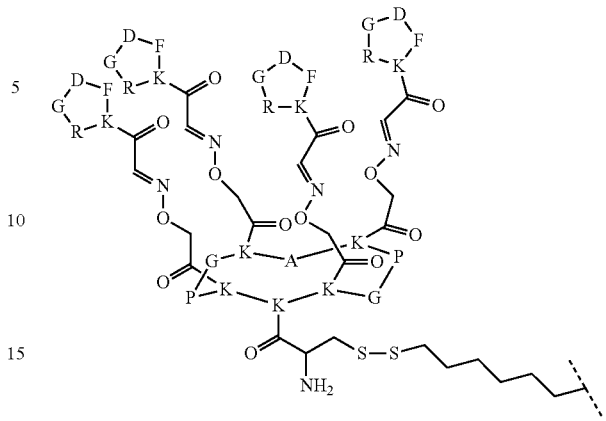

In another preferred embodiment, the present invention relates to a compound as described above, wherein the compound of formula I(bis) forms a complex of formula II with a vectorization fragment R', wherein R' is a A-B fragment of the following formula:

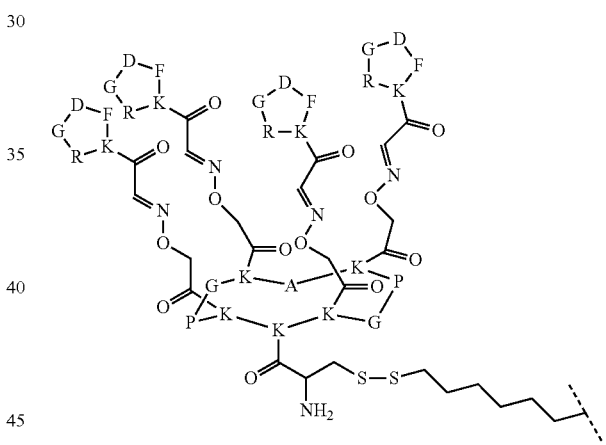

In an advantageous embodiment, the present invention relates to a compound of formula I(bis), wherein said compound of formula I(bis) forms a complex of formula II with a vectorization fragment R';

in particular said vectorization fragment R' being covalently bound to the compound of formula I through the nitrogen atom bearing the R atom when the compound of formula I is not forming a complex of formula II;

said vectorization fragment R' being, in particular, an A-B fragment comprising an A group and a B group;

said A group being more particularly comprising a X-Peptide1-Y, said A group being preferably of the following formula:

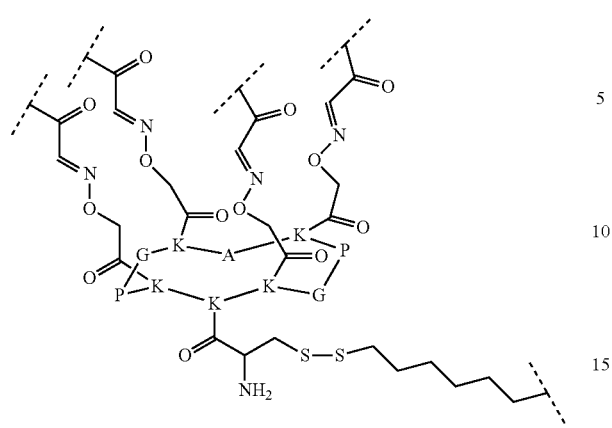
said B group being more particularly chosen from a peptide or an acid residue selected from a hyaluronic acid or a folic acid, said B group being preferably a peptide of the following formula:
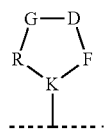
In an advantageous embodiment, the present invention relates to a compound as defined above, of one of the following formulae:
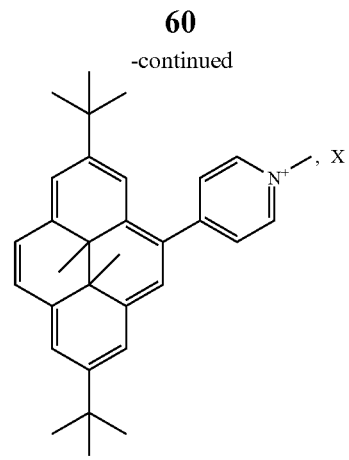
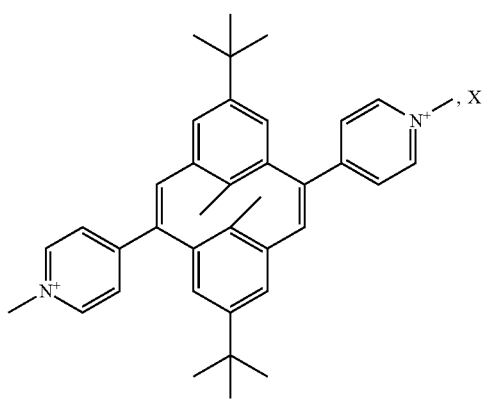
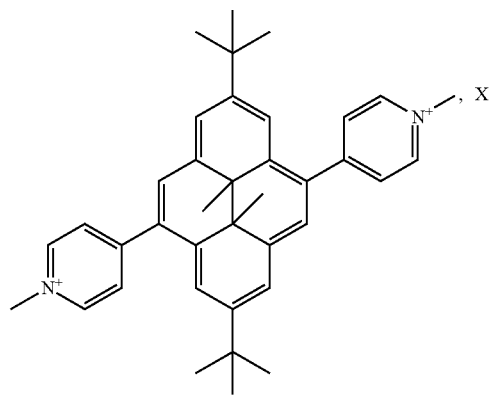
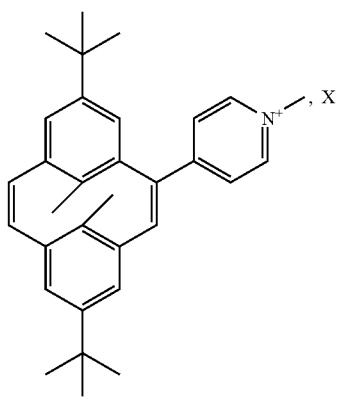

In an advantageous embodiment, the present invention relates to a complex as defined above, of one of the following formulae:
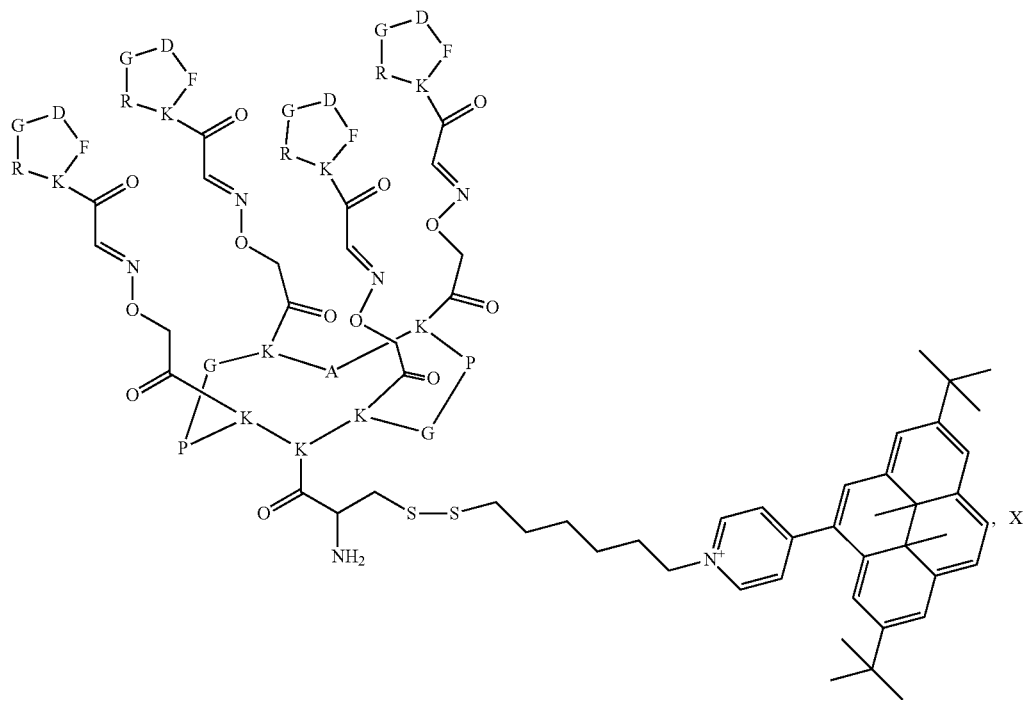

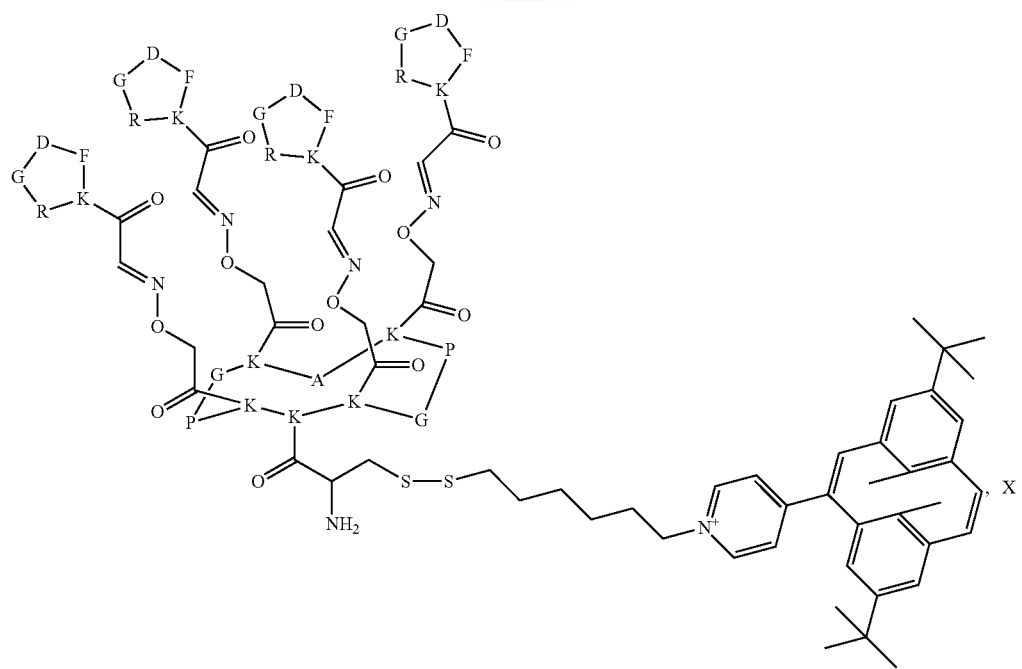
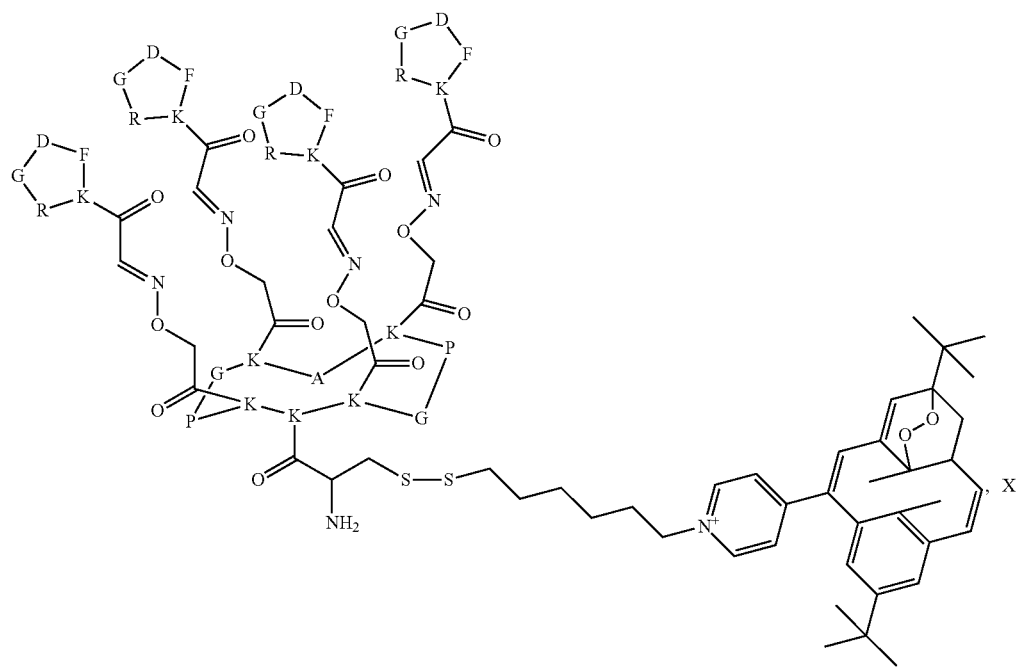

In an advantageous embodiment, the present invention relates to a compound or a complex as defined above, of one of the following formulae:

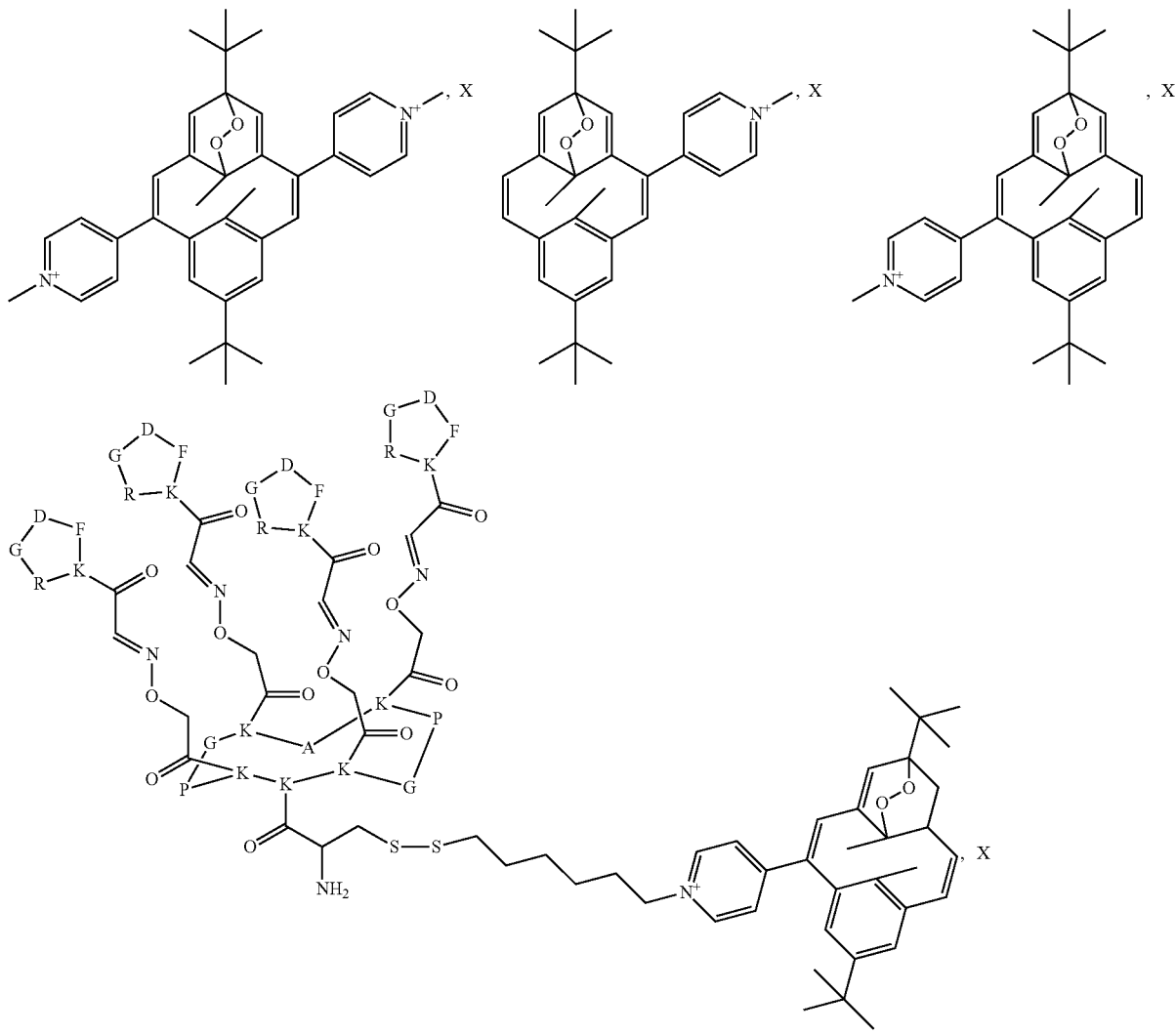

In another aspect, the present invention relates to the use of a compound or a complex as defined above, to produce singlet oxygen.

In another aspect, the present invention relates to the use of a compound or a complex as defined above, in lithography.

In another aspect, the present invention relates to the use of a compound or a complex as defined above, for oxidation in organic synthesis.

In another aspect, the present invention relates to the use of a compound or a complex as defined above, in wastewater treatment.

In particular, treatment of wastewater can be performed as follows: a compound of formula I-1 as defined above is immobilized onto a solid substrate, for example silica or organic resin, and then irradiated by visible light to produce singlet oxygen that is known to destroy organic pollutants such as phenols.

Wastewater can also be treated by adding a compound of formula I-3 as defined above into the water to treat. Singlet oxygen is then generated by thermal treatment, for example at 37° C.

In another aspect, the present invention relates to the use of a compound or a complex as defined above, in blood sterilization.

This treatment of blood is for example performed prior to or during storage in a blood bank.

In particular, irradiation of blood by visible light in the presence of a compound of formula I-1 as defined above produces singlet oxygen that is known to kill viruses.

Blood can also be sterilized by adding a compound of formula I-3 as defined above into the blood to sterilize. Singlet oxygen is then generated by thermal treatment, for example at 37° C.

In another aspect, the present invention relates to the use of a compound or a complex as defined above, as insecticides.

In another aspect, the present invention relates to the use of a compound or a complex as defined above, as herbicides.

In another aspect, the present invention relates to a process of preparation of a compound of following formula I-3

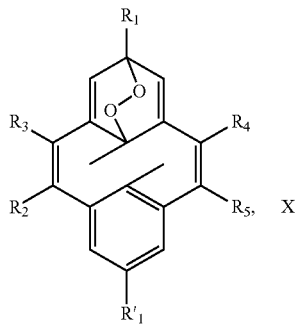

wherein:
$R_1$ and $R'_1$ represent independently from each other:
H,
a linear or branched ($C_1$-$C_{18}$)-alkyl,
a ($C_3$-$C_8$)-cycloalkyl,

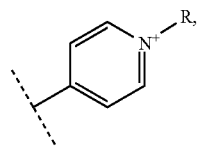

—$NR_3^+$,
R representing:
H,
a linear or branched ($C_1$-$C_{18}$)-alkyl,
a ($C_3$-$C_8$)-cycloalkyl,
$R_2$, $R_3$, $R_4$ and $R_5$ represent independently from each other:
H,
a linear or branched ($C_1$-$C_{18}$)-alkyl,
a ($C_3$-$C_8$)-cycloalkyl,

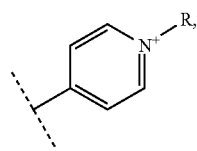

—$NR_3^+$,
R representing:
H,
a linear or branched ($C_1$-$C_{18}$)-alkyl,
a ($C_3$-$C_8$)-cycloalkyl,
X represents one or more physiologically acceptable counter anion(s),
providing that:
at least one of $R_1$, $R'_1$, $R_2$, $R_3$, $R_4$ and $R_5$ represents one of the following groups:

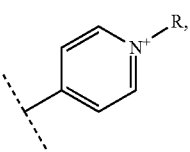

or
—$NR_3^+$,
comprising a step of irradiating at $\lambda \geq 630$ nm in presence of oxygen a compound of following formula I-1

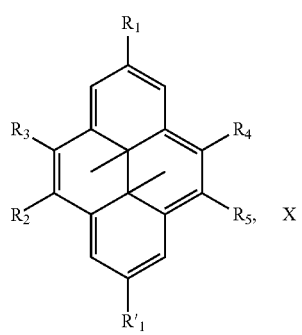

wherein $R_1$, $R'_1$, $R_2$, $R_3$, $R_4$, $R_5$ and X are as defined above.

In another aspect, the present invention relates to a process of preparation of a complex of following formula II-3

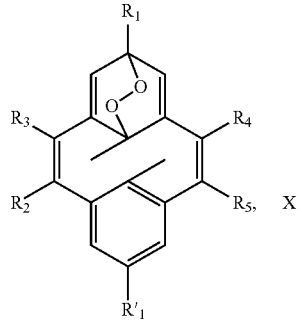

wherein:
$R_1$ and $R'_1$ represent independently from each other:
H,
a linear or branched ($C_1$-$C_{18}$)-alkyl,
a ($C_3$-$C_8$)-cycloalkyl,

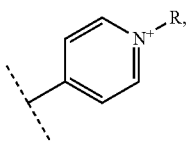

—$NR_3^+$,
R representing:
H,
a linear or branched ($C_1$-$C_{18}$)-alkyl,
a ($C_3$-$C_8$)-cycloalkyl, $R_2$, $R_3$, $R_4$ and $R_5$ represent independently from each other:
H,
a linear or branched ($C_1$-$C_{18}$)-alkyl,
a ($C_3$-$C_8$)-cycloalkyl,

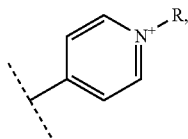

—$NR_3^+$,
R representing:
H,
a linear or branched ($C_1$-$C_{18}$)-alkyl,
a ($C_3$-$C_8$)-cycloalkyl,
X represents one or more physiologically acceptable counter anion(s),
providing that:
at least one of $R_1$, $R'_1$, $R_2$, $R_3$, $R_4$ and $R_5$ represents one of the following groups:

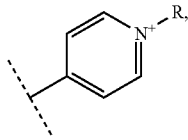

or
—$NR_3^+$,
comprising a step of irradiating at $\lambda \geq 630$ nm in presence of oxygen a complex of following formula II-1

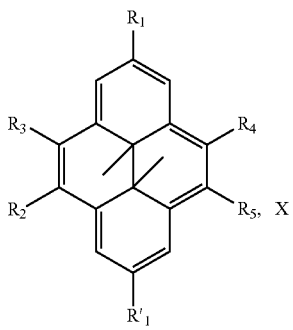

II-1 wherein $R_1$, $R'_1$, $R_2$, $R_3$, $R_4$, $R_5$ and X are as defined above.

In an advantageous embodiment, the present invention relates to a process as defined above, wherein said step of irradiating is performed in presence of oxygen, or oxygen containing gases, such as air, in particular at 1 atm.

In an advantageous embodiment, the present invention relates to a process as defined above, wherein said step of irradiating is performed at a temperature comprised from 0° C. to 50° C., in particular from 10° C. to 40° C., more particularly at 25° C.

In another aspect, the present invention relates to a process of preparation of a compound of following formula I-3

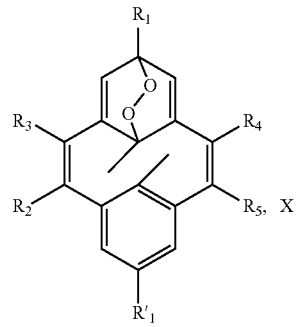

I-3 wherein:
$R_1$ and $R'_1$ represent independently from each other:
H,
a linear or branched ($C_1$-$C_{18}$)-alkyl,
a ($C_3$-$C_5$)-cycloalkyl,

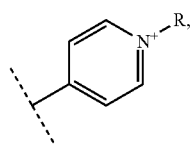

—$NR_3^+$,
R representing:
H,
a linear or branched ($C_1$-$C_{18}$)-alkyl,
a ($C_3$-$C_8$)-cycloalkyl,
$R_2$, $R_3$, $R_4$ and $R_5$ represent independently from each other:
H,
a linear or branched ($C_1$-$C_{18}$)-alkyl,
a ($C_3$-$C_8$)-cycloalkyl,

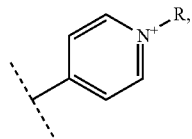

—$NR_3^+$,
R representing:
H,
a linear or branched ($C_1$-$C_{18}$)-alkyl,
a ($C_3$-$C_5$)-cycloalkyl,
X represents one or more physiologically acceptable counter anion(s),
providing that:
at least one of $R_1$, $R'_1$, $R_2$, $R_3$, $R_4$ and $R_5$ represents one of the following groups:

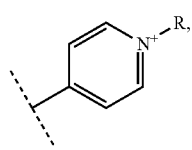

or
—NR$_3^+$,
comprising a step of contacting a compound of following formula I-2

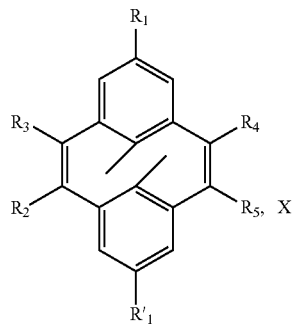

I-2 wherein R$_1$, R'$_1$, R$_2$, R$_3$, R$_4$, R$_5$ and X are as defined above, with:
  singlet oxygen, or
  dioxygen and a photosensitizer.

In another aspect, the present invention relates to a process of preparation of a complex of following formula II-3

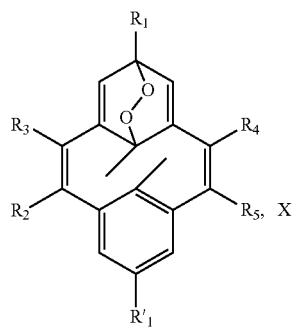

I-3 wherein:
  R$_1$ and R'$_1$ represent independently from each other:
  H,
  a linear or branched (C$_1$-C$_{18}$)-alkyl,
  a (C$_3$-C$_8$)-cycloalkyl,

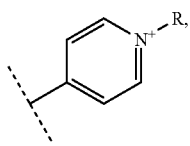

—NR$_3^+$,
R representing:
  H,
  a linear or branched (C$_1$-C$_{18}$)-alkyl,
  a (C$_3$-C$_8$)-cycloalkyl,
  R$_2$, R$_3$, R$_4$ and R$_5$ represent independently from each other:

H,
a linear or branched (C$_1$-C$_{18}$)-alkyl,
a (C$_3$-C$_8$)-cycloalkyl,

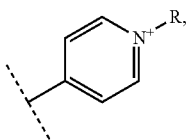

—NR$_3^+$,
R representing:
  H,
  a linear or branched (C$_1$-C$_{18}$)-alkyl,
  a (C$_3$-C$_8$)-cycloalkyl,
  X represents one or more physiologically acceptable counter anion(s),
providing that:
  at least one of R$_1$, R'$_1$, R$_2$, R$_3$, R$_4$ and R$_5$ represents one of the following groups:

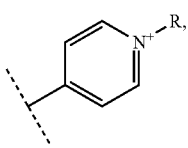

or
—NR$_3^+$,
comprising a step of contacting a complex of following formula II-2

I-2 wherein R$_1$, R'$_1$, R$_2$, R$_3$, R$_4$, R$_5$ and X are as defined above, with:
  singlet oxygen, or
  dioxygen and a photosensitizer.

Thus, compounds of formula I-2, or complexes of formula II-2, can form compounds of formula I-3, or complexes of formula II-2 respectively, in contact with singlet oxygen, which is generated beforehand or in situ, in presence of an external photosensitizer and oxygen or an oxygen containing gas.

In another aspect, the present invention relates to a process of preparation of oxygen singlet and a compound of following formula I-1

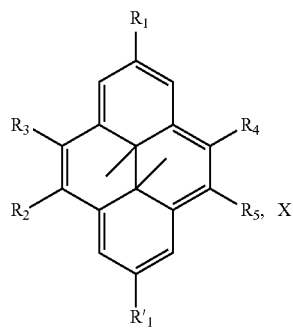

I-1 wherein:
R$_1$ and R'$_1$ represent independently from each other:
H,
a linear or branched (C$_1$-C$_{18}$)-alkyl,
a (C$_3$-C$_8$)-cycloalkyl,

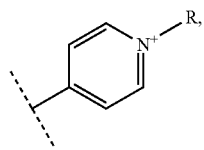

—NR$_3^+$,
R representing:
H,
a linear or branched (C$_1$-C$_{18}$)-alkyl,
a (C$_3$-C$_8$)-cycloalkyl,
R$_2$, R$_3$, R$_4$ and R$_5$ represent independently from each other:
H,
a linear or branched (C$_1$-C$_{18}$)-alkyl,
a (C$_3$-C$_8$)-cycloalkyl,

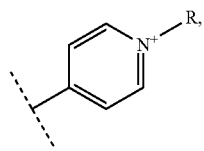

—NR$_3^+$,
R representing:
H,
a linear or branched (C$_1$-C$_{18}$)-alkyl,
a (C$_3$-C$_8$)-cycloalkyl,
X represents one or more physiologically acceptable counter anion(s),
providing that:
at least one of R$_1$, R'$_1$, R$_2$, R$_3$, R$_4$ and R$_5$ represents one of the following groups:

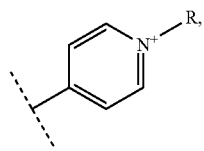

or
—NR$_3^+$,
comprising a step of thermal treatment, in particular without any light irradiation, at a temperature comprised from 25 to 100° C., in particular at 37° C., of a compound of following formula I-3

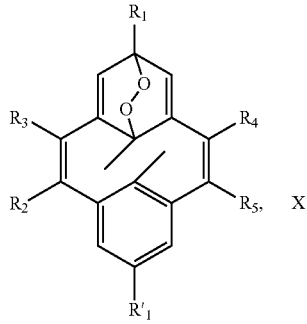

I-3 wherein R$_1$, R'$_1$, R$_2$, R$_3$, R$_4$, R$_5$ and X are as defined above.

In another aspect, the present invention relates to a process of preparation of oxygen singlet and a complex of following formula II-1

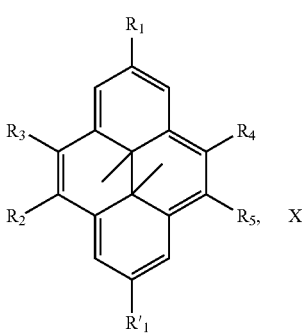

II-1 wherein:
R$_1$ and R'$_1$ represent independently from each other:
H,
a linear or branched (C$_1$-C$_{18}$)-alkyl,
a (C$_3$-C$_8$)-cycloalkyl,

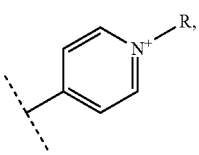

—NR$_3^+$,
R representing:
H,
a linear or branched (C$_1$-C$_{18}$)-alkyl,
a (C$_3$-C$_8$)-cycloalkyl,
R$_2$, R$_3$, R$_4$ and R$_5$ represent independently from each other:
H,
a linear or branched (C$_1$-C$_{18}$)-alkyl,
a (C$_3$-C$_8$)-cycloalkyl,

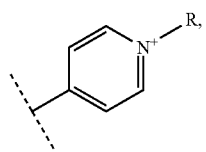

—NR$_3^+$,
R representing:
H,
a linear or branched (C$_1$-C$_{18}$)-alkyl,
a (C$_3$-C$_8$)-cycloalkyl,
X represents one or more physiologically acceptable counter anion(s),
providing that:
at least one of R$_1$, R'$_1$, R$_2$, R$_3$, R$_4$ and R$_5$ represents one of the following groups:

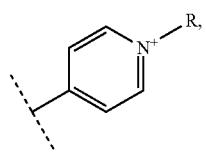

or
—NR$_3^+$,
comprising a step of thermal treatment, in particular without any light irradiation, at a temperature comprised from 25 to 100° C., in particular at 37° C., of a complex of following formula II-3

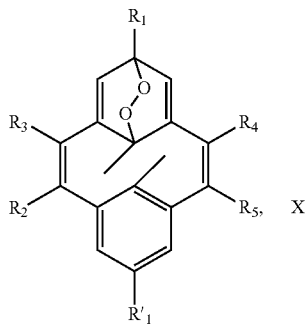

wherein R$_1$, R'$_1$, R$_2$, R$_3$, R$_4$, R$_5$ and X are as defined above.

In another aspect, the present invention relates to a method of treating pathologies sensitive to singlet oxygen, in particular cancers, comprising administrating to a patient in need thereof an effective amount of a compound of formula I-3, or of a complex of formula II-3, as defined above.

In an advantageous embodiment, the present invention relates to a method as defined above, wherein said compound of formula I-3 releases singlet oxygen without the need to irradiate said compound of formula I-3, by thermal treatment, for example at 37° C.

In an advantageous embodiment, the present invention relates to a method as defined above, wherein said complex of formula II-3 releases singlet oxygen without the need to irradiate said complex of formula II-3, by thermal treatment, for example at 37° C.

Compounds of formula I-3 release singlet oxygen with regeneration of the compound I-1.

Complexes of formula II-3 release singlet oxygen with regeneration of the complex II-1.

In another aspect, the present invention relates to a method of treating pathologies sensitive to singlet oxygen, in particular by phototherapy and/or in the treatments of cancers, comprising administrating to a patient in need thereof an effective amount of a compound of formula I-1, or of a complex of formula II-1, as defined above, and subsequent irradiating at λ≥630 nm in presence of oxygen, without adding an external photo sensitizer, to obtain compound of formula I-3, or a complex of formula II-3, respectively.

In an advantageous embodiment, the present invention relates to a method as defined above, wherein said compound of formula I-3, or complex of formula II-3, releases singlet oxygen without the need to irradiate said compound of formula I-3, or said complex of formula II-3, respectively, by thermal treatment, for example at 37° C.

In another aspect, the present invention relates to a method of treating pathologies sensitive to singlet oxygen, in particular by phototherapy and/or in the treatments of cancers, comprising administrating to a patient in need thereof an effective amount of a compound of formula I-2, or of a complex of formula II-2, as defined above, and contacting said compound with singlet oxygen, said singlet oxygen being generated beforehand or in situ, in presence of an external photosensitizer and oxygen or an oxygen containing gas, to obtain a compound of formula I-3, or a complex of formula II-3, respectively.

In an advantageous embodiment, the present invention relates to a method as defined above, wherein said compound of formula I-3 releases singlet oxygen without the need to irradiate said compound of formula I-3, by thermal treatment, for example at 37° C.

In another advantageous embodiment, the present invention relates to a method as defined above, wherein said complex of formula II-3 releases singlet oxygen without the need to irradiate said complex of formula II-3, by thermal treatment, for example at 37° C.

FIGURES

Figure 1:
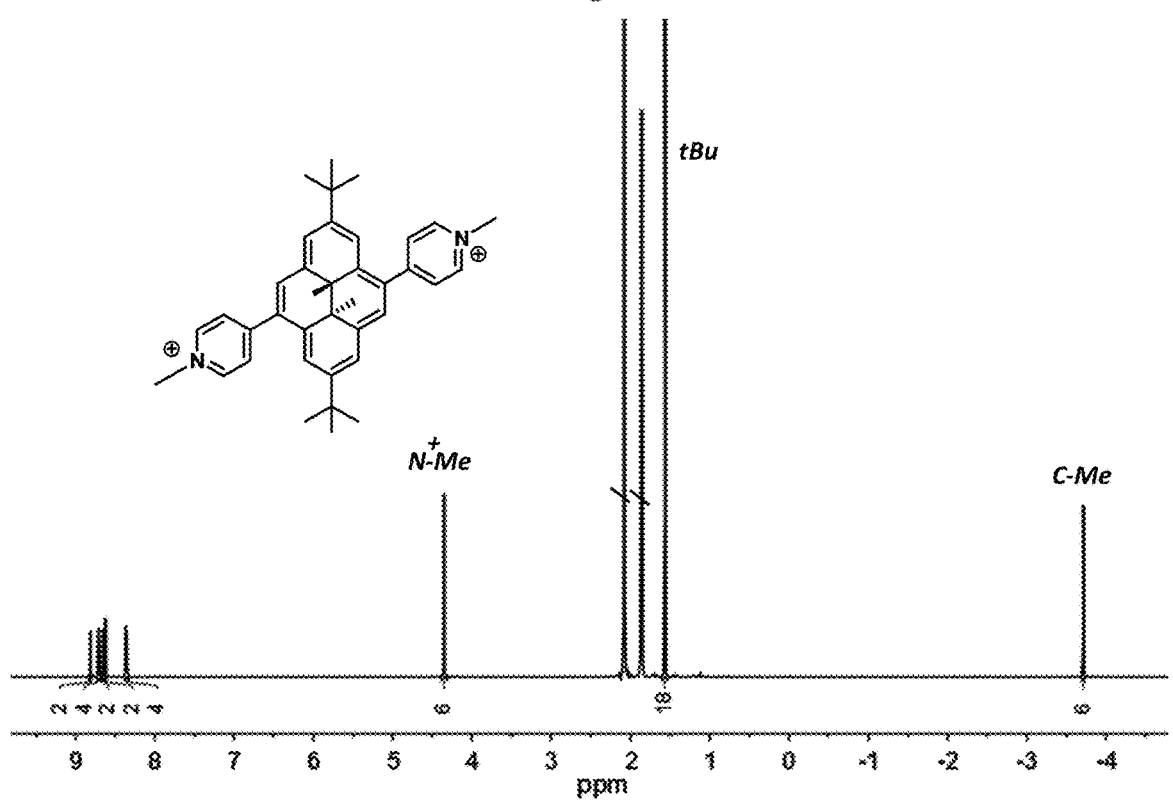
FIG. 1 represents the $^1$H-NMR spectra of compound 1 in CD$_3$CN.
Figure 2:
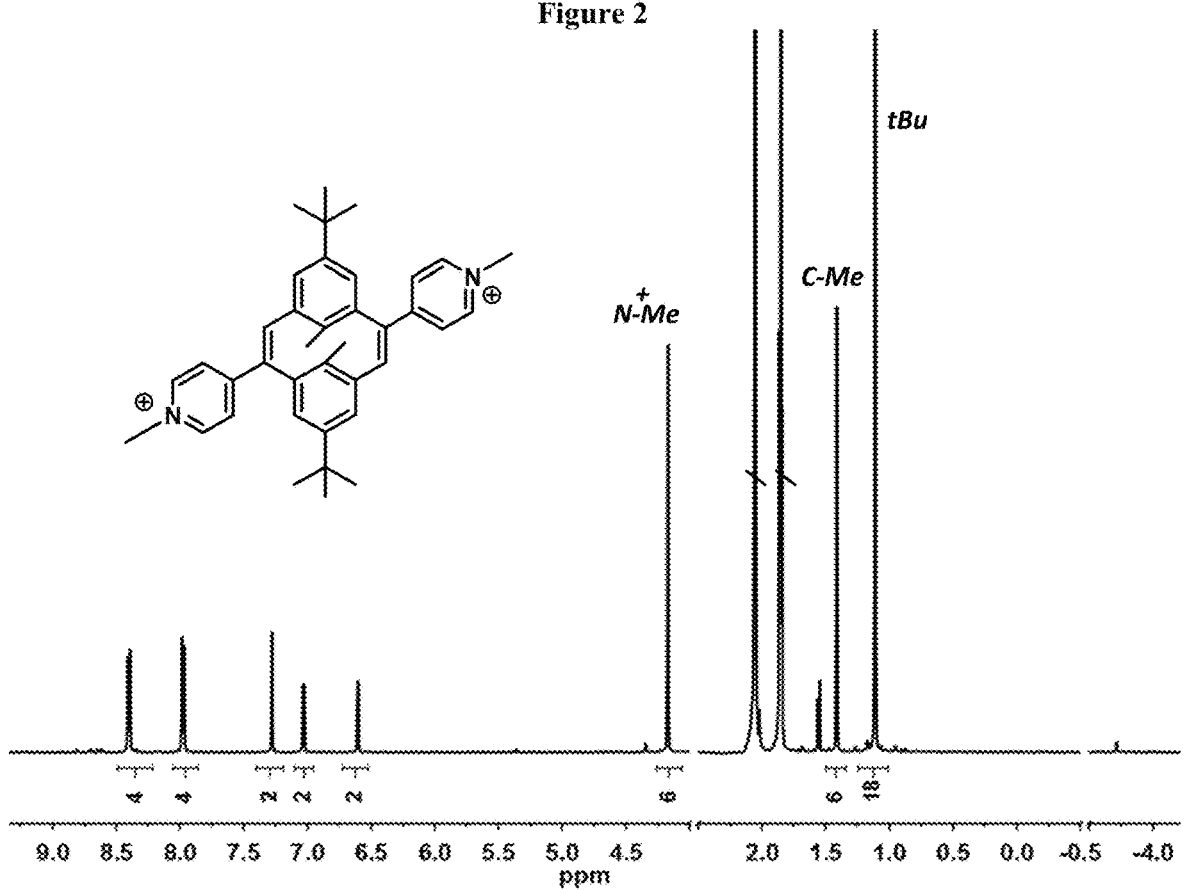
FIG. 2 represents the $^1$H-NMR spectra of compound 2 in CD$_3$CN.
Figure 3:
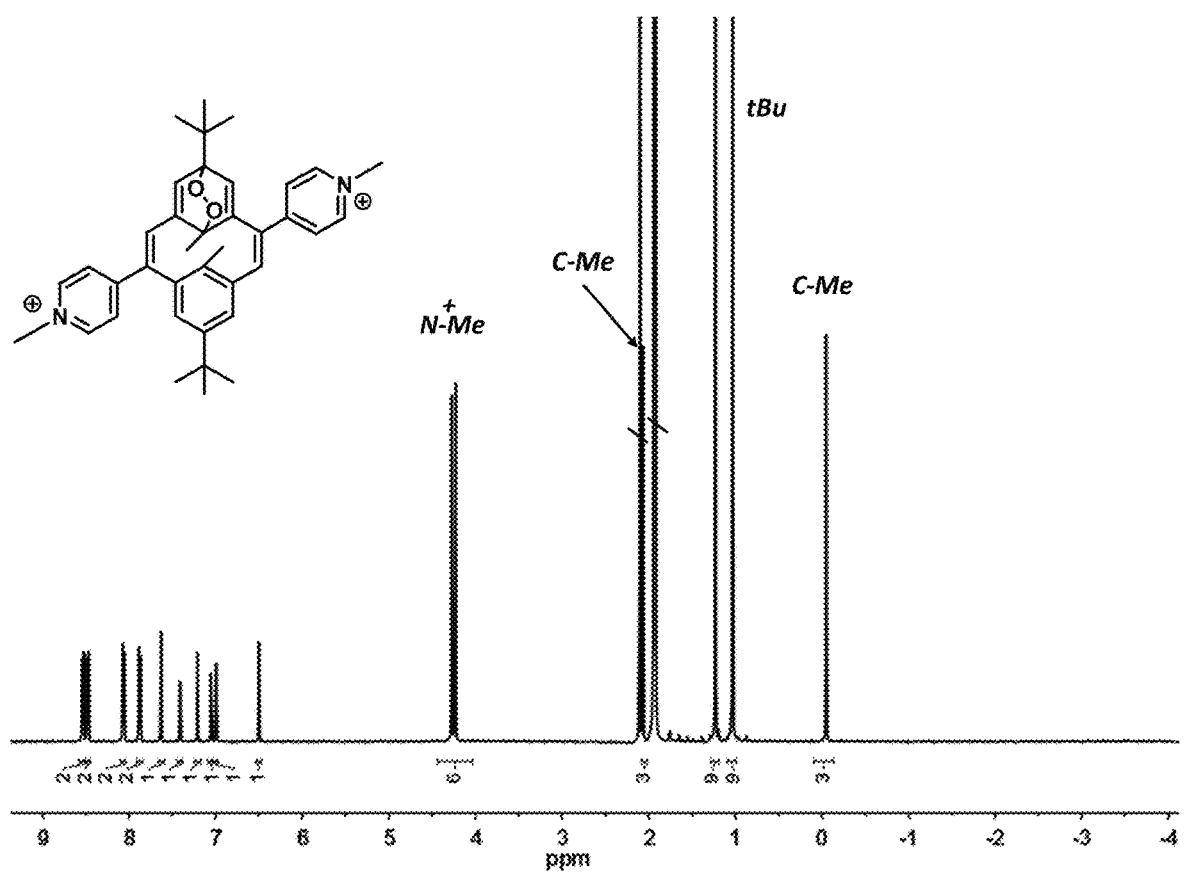
FIG. 3 represents the $^1$H-NMR spectra of compound 3 in CD$_3$CN.
Figure 4:
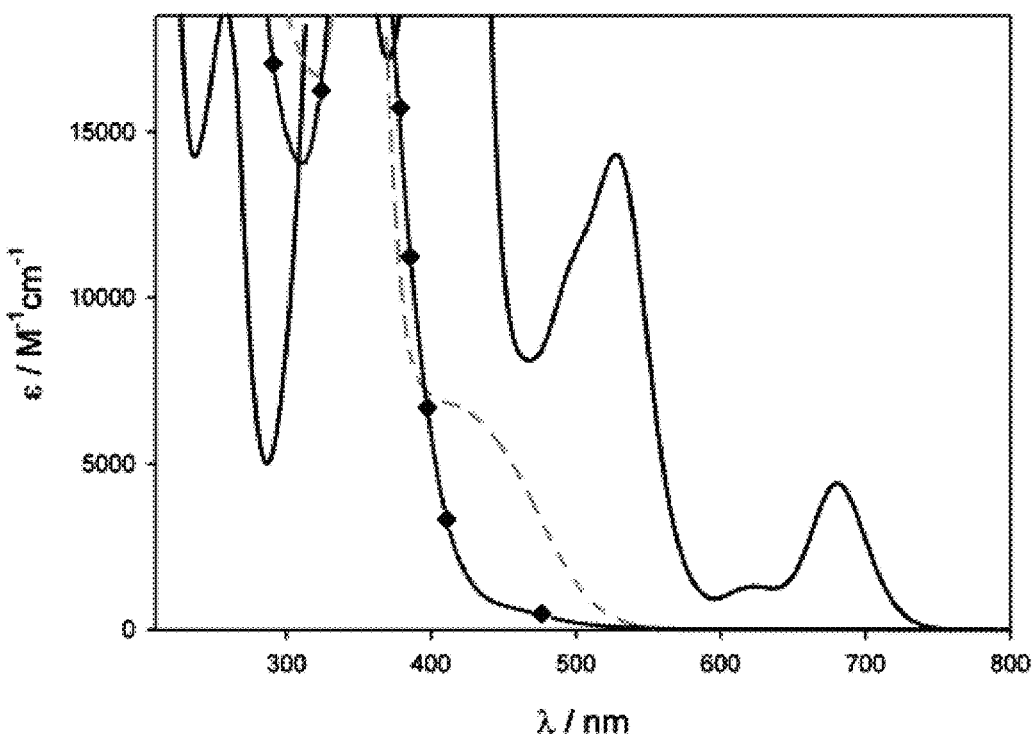
FIG. 4 represents the UV-visible absorption spectra of 1 (solid line), 2 (dotted line) and 3 (diamond line) in CH$_3$CN.
Figure 5:
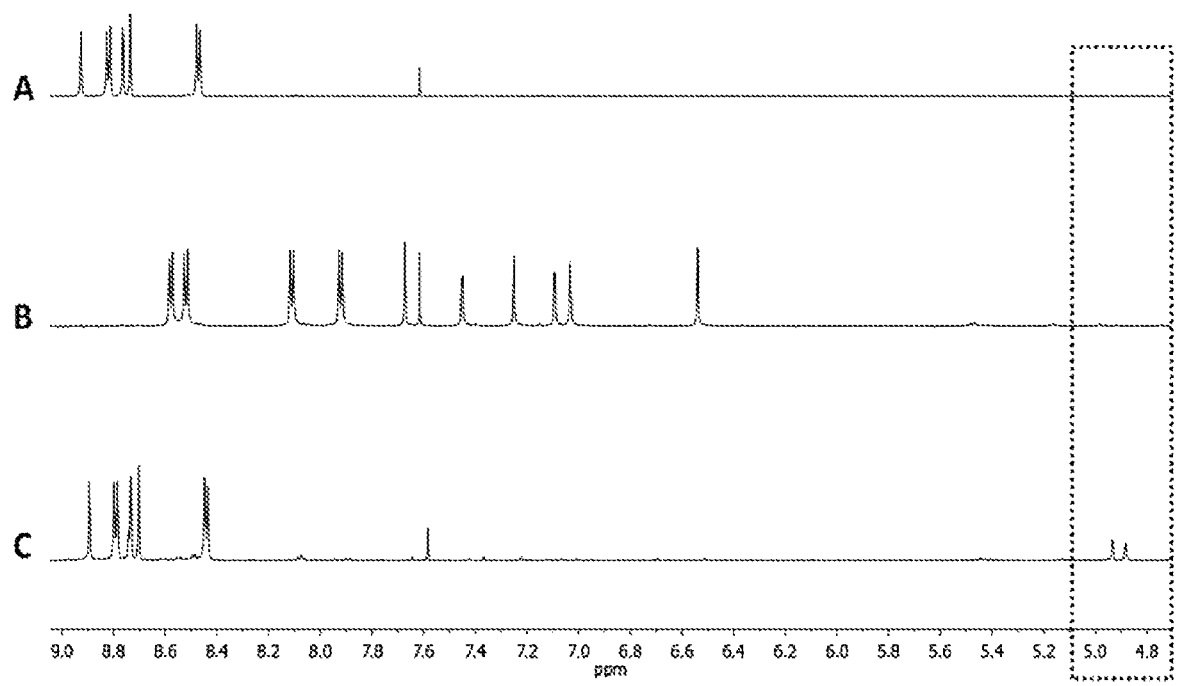

FIG. 5 presents the $^1$H NMR spectra of: (A) 1, (B) Photogenerated 3, and (C) reaction mixture in CD$_3$CN after cyeloreversion of 3 back to 1 in the presence of 30-fold excess 2,3-dimethyl-2-butene. Signals at 4.88 and 4.93 ppm in C correspond to the two olefin protons for trapped product.

Figure 6:
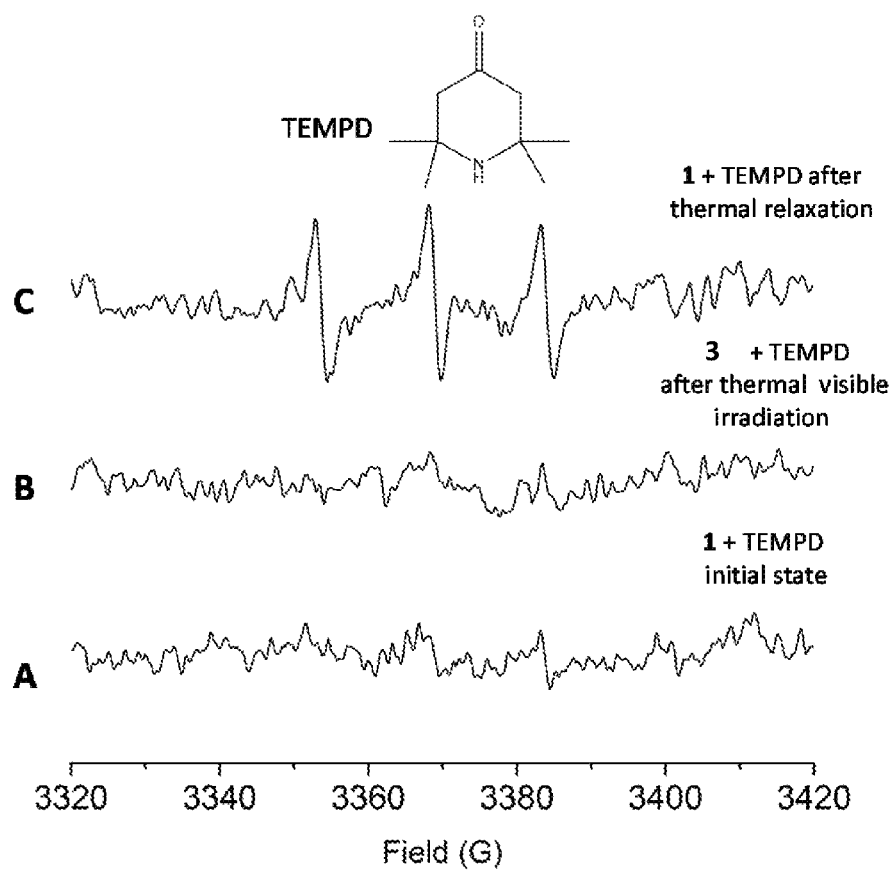

FIG. 6 presents the EPR spectra of nitroxide radical generated from TEMPD. 1M solution of TEMPD was mixed with 44 μM of 1. A: initial state. B: upon irradiation with red light (λ>630 nm). C: upon thermal relaxation and recovery of 1.

Figure 7:
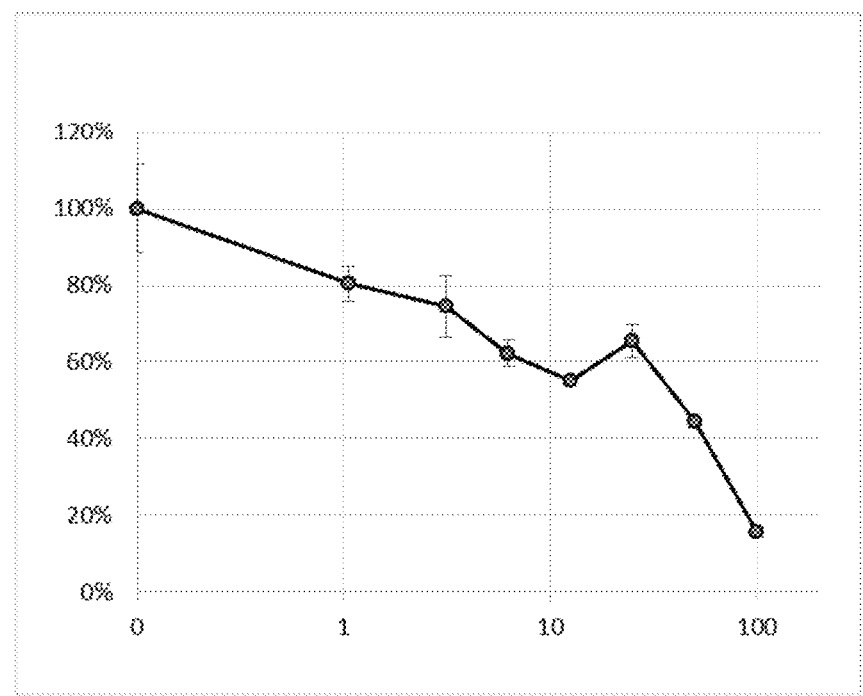

FIG. 7 presents the evaluation of the cytotoxicity of compound 5 under irradiation on IGROV1 cells. The graph corresponds to the viability of the cells, in percent, in function of the concentration of compound 5 in μM.

Figure 8:
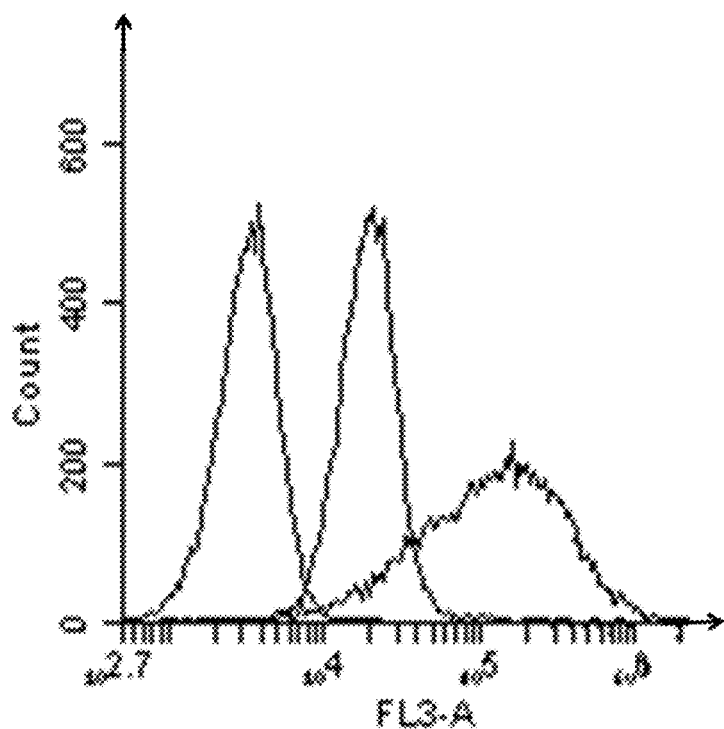

FIG. 8 represents the flow cytometer analysis of compound 5. The dark grey line corresponds to the IGROV1 cells without addition of a compound of the Invention, the Mack line corresponds to the IGROV1 cells incubated with compound 4 and the grey line corresponds to the IGROV1 cells incubated with complex 5.

EXAMPLES

General Procedures and Methods

All purchased chemicals and solvents were used as received except THF and diethyl ether that were distilled over sodium/benzophenone under argon. NMR spectra were recorded on a Bruker Avance-500 MHz or 400 MHz spectrometer in $CD_3CN$. Chemical shifts (ppm) are referenced to residual solvent peaks. Mass spectrometry analyses (ESI positive mode) were carried out at the DCM mass spectrometry facility with an Esquirre 3000 Plus (Bruker Daltonics). Absorption spectra were recorded using either a Varian Cary 50 Scan or a Varian Cary 300 UV-visible spectrophotometer equipped with a temperature controller unit. Luminescence spectra in the NIR were recorded on an Edinburgh Instruments FLS-920 spectrometer equipped with a Ge detector cooled at 77K.

Irradiation experiments have been conducted either under inert atmosphere using a Jaram glove box with carefully degassed solvents or under air (1 atm). Visible irradiations experiments have been carried out with a Xe—Hg lamp, using a 630 nm cut-off filter unless otherwise stated and the samples have been placed in a water bath (room temperature or 8° C.). Samples have been placed at a distance of 15 cm of the visible lamp. The reactions have been investigated from UV-visible and NMR experiments. Intermediate spectra have been recorded at different times depending on the isomerization process rates. The ratio between the different forms has been determined by $^1$H-NMR from the relative integration of the characteristic resonance peaks of the $N^+$-Me methyl groups of the different forms.

Example 1: Preparation of compound 1: 2,7-di-tert-butyl-4,9-di-(N-methylpyridin-4-yl)-trans-10b,10c-dimethyl-10b,10c-dihydropyrene hexafluorophosphate 1 was prepared as represented in Scheme S1.

Scheme S1. Preparation of 1.

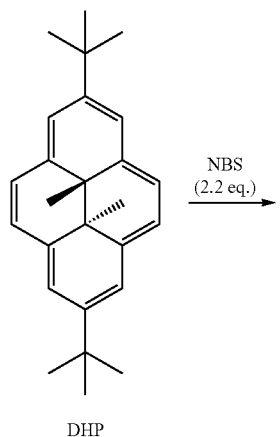

DHP

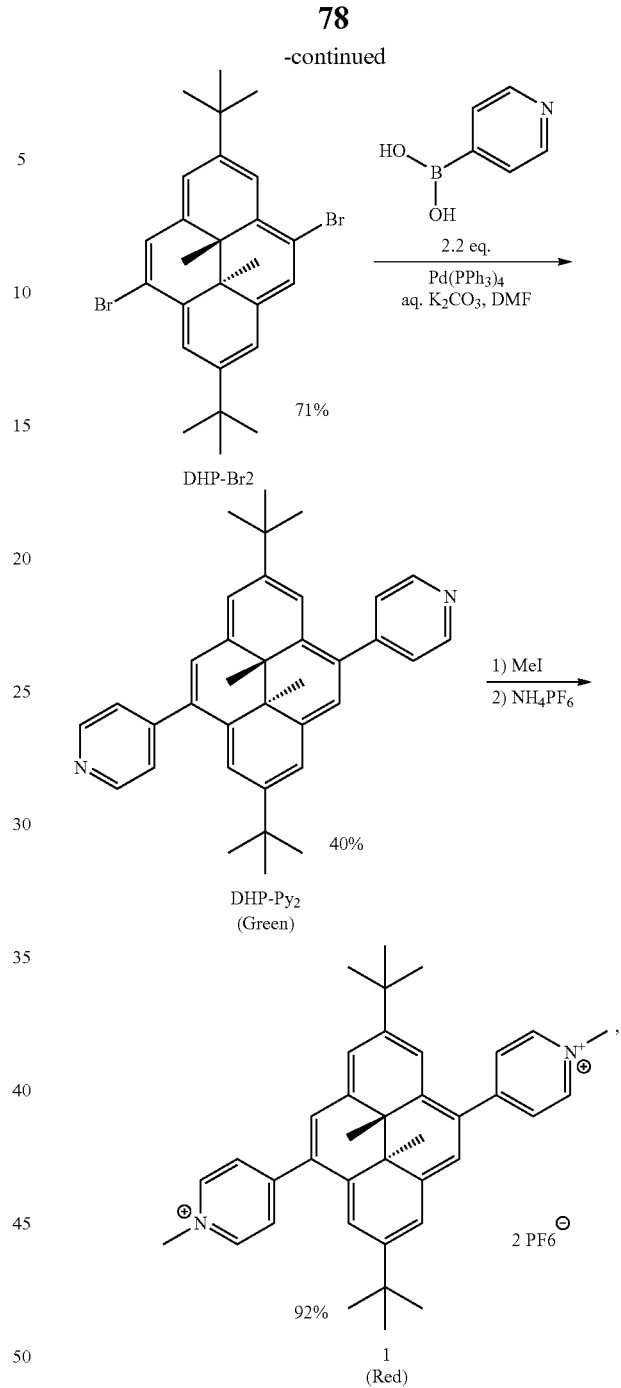

2,7-Di-tert-butyl-trans-10b,10c-dimethyl-10b,10c-dihydropyrene (DHP), and 4,9-dibromo-2,7-di-tert-butyl-trans-10b,10c-dimethyl-10b-10c dihydropyrene (DRP-Br$_2$) were synthesized following the procedures described in Mitchell et al. (*J. Am. Chem. Soc.* 2003, 125, 2974-2988) and Vila et al. (*Inorg. Chem.* 2011, 50, 10581-10591).

2,7-di-tert-butyl-4,9-di-(4-pyridyl)-trans-10b,10c-dimethyl-10b,10c-dibydropyrene (DHP-Py$_2$)

A round bottom flask was filled under an argon atmosphere with 4,9-dibromo-2,7-di-tert-butyl-trans-10b,10c-dimethyl-10b,10c-dihydropyrene (0.100 g, 0.2 mmol), 4-pyridinylboronic acid (52 mg, 0.42 mmol) and freshly distilled THF (6 mL). A degassed aqueous solution (2 mL)

of sodium carbonate (0.1 g, 0.95 mmol) and Pd(PPh$_3$)$_4$ (35 mg, 0.03 mmol) was then added into the flask and the resulting mixture was heated under stirring for 48 h. After cooling the mixture to room temperature, the solvent was evaporated under reduced pressure and the residue was then dissolved in water and extracted with dichloromethane. The solution was dried over anhydrous MgSO$_4$, filtered and the solvent was evaporated under reduced pressure. Around 5 mL of diethyl ether were added to the crude product and the insoluble DHP-Py$_2$ was then filtered and dried under vacuum. DHP-Py$_2$ was isolated as a dark brown solid (40 mg, 40% yield). DHP-Py$_2$: $^1$H NMR (400 MHz, 298 K, CDCl$_3$) δ (ppm): −3.68 (s, 6H), 1.61 (s, 18H), 7.78 (m, 4H), 8.48 (s, 2H), 8.60 (s, 2H), 8.64 (s, 2H), 8.85 (m, 4H). ESIMS: m/z: calcd for C$_{36}$H$_{38}$N$_2$+H$^+$: 499.7 [M+H$^+$] found: 499.4. Exact mass (M$^+$) calc.: 499.3107, found: 499.3105. Anal. Calc. for C$_{36}$H$_{38}$N$_2$.0.5H$_2$O: C, 85.16; H, 7.74; N, 5.52. found: C, 85.16; H, 7.96; N, 5.10. 5o: RMN 1H (400 MHz, 298 K, CDCl$_3$) δ (ppm): 1.18 (s, 18H), 1.54 (s, 6H), 6.57 (d, J=2 Hz, 2H), 6.84 (s, 2H), 6.86 (d, J=2 Hz, 2H), 7.48 (m, 4H), 8.61 (m, 4H).

2,7-di-tert-butyl-4,9-di-(N-methylpyridin-4-yl)-trans-10b,10c-dimethyl-10b,10c-dihydropyrene hexafluorophosphate (1, 2 PF$_6^-$)

35 mg of DHP-Py$_2$ (0.070 mmol) were dissolved in 20 mL CH$_2$Cl$_2$. 1 mL of CH$_3$I was then rapidly added and the solution was refluxed for two hours. Upon cooling down to room temperature, the precipitate formed (iodide salt) was filtered off, washed with cold CH$_2$Cl$_2$ and dissolved in 40 mL CH$_3$OH. Addition of a saturated aqueous solution of NH$_4$PF$_6$ precipitated the hexafluorophosphate salt of 1 as a red-brown solid that was collected by filtration, washed with cold water and CH$_3$OH and dried under vacuum. Crystals could be obtained by slow diffusion of diethyl ether into a CH$_3$CN solution of 1 (yield 92%, 45 mg, 64.4 μmol). 1: $^1$H NMR (500 MHz, 298 K, CD$_3$CN) δ (ppm): −3.63 (s, 6H), 1.65 (s, 18H), 4.43 (s, 6H), 8.45 (m, 4H), 8.70 (s, 2H), 8.73 (s, 2H), 8.79 (m, 4H), 8.89 (s, 2H). Exact mass: m/z: calcd for C$_{38}$H$_{44}$N$_2^{2+}$: 264.1747 [M-2PF$_6^-$], found: 264.1750.

Example 2: Preparation of compound 4: 2,7-di-tert-butyl-4-(N-methylpyridin-4-yl)-trans-10b,10c-dimethyl-10,10c-dihydropyrene hexafluorophosphate

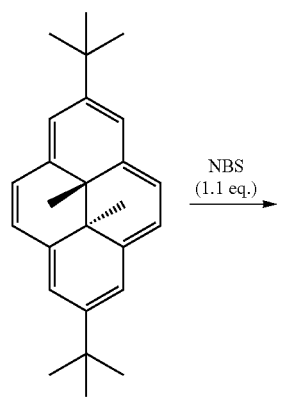

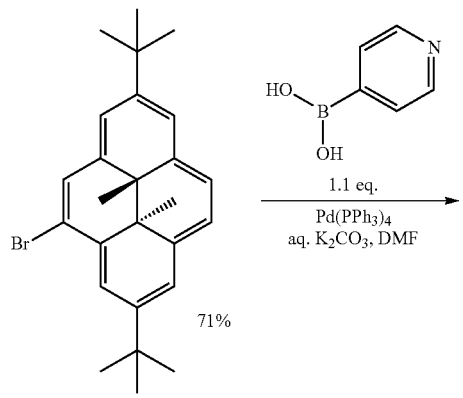

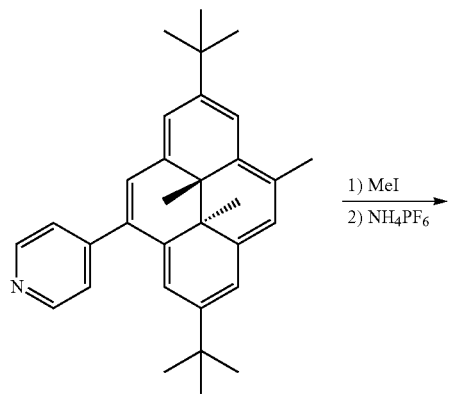

4

4-bromo-2,7-di-tert-butyl-trans-10b,10c-dimethyl-10b-10c-dihydropyrene

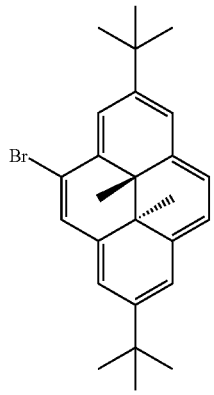

To a solution containing 2,7-di-tert-butyl-trans-10b,10c-dimethyl-10b,10c-dihydropyrene (350 mg, 1.02 mmol) in 190 mL of dry $CH_2Cl_2$ at −40° C. was slowly added (1 hour) with stirring under an argon atmosphere a solution containing N-bromosuccinimide (181 mg, 1.02 mmol) in dry DMF (35 mL) at −40° C. After addition, the solution was kept under stirring 1 hour at room temperature. Cyclohexane (80 mL) and water were then added. The organic phase was collected, washed with brine, dried over anhydrous $Na_2SO_4$ and evaporated under reduced pressure. The crude product was purified by column chromatography on silica gel using cyclohexane:$CH_2Cl_2$ (6:1, vol:vol) as eluent to afford 4-bromo-2,7-di-tert-butyl-trans-10b,10c-dimethyl-10b-10c-dihydropyrene as dark green crystals. (411 mg, yield 90%) $^1$H NMR (400 MHz, $CDCl_3$) δ/ppm: 8.81 (d, 1H), 8.64 (s, 1H), 8.54 (d, 2H, J=1.7 Hz), 8.48 (bs, 1H), 8.47 (s, 2H), 1.71 (s, 9H, t-Bu), 1.68 (s, 9H, t-Bu), −3.91 (s, 3H, —$CH_3$), −3.92 (s, 3H, —$CH_3$).

2,7-di-tert-butyl-4-(4-pyridyl)-trans-10b,10c-dimethyl-10b,10c-dihydropyrene

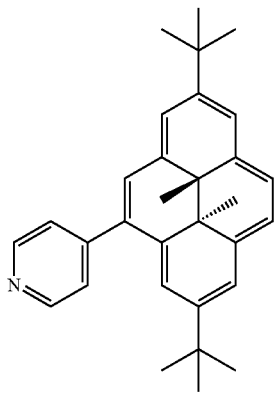

4-bromo-2,7-di-tert-butyl-trans-10b,10c-dimethyl-10b,10c-dihydropyrene (0.100 g, 0.236 mmol) and 4-pyridinylboronic acid (32 mg, 0.26 mmol) were dissolved in degassed and freshly distilled THF (6 mL). A solution of sodium carbonate (100 mg, 0.95 mmol) in water (2 mL) and tetrakis(triphenylphosphine)palladium(0) (35 mg, 0.03 mmol) were then introduced under an inert atmosphere. The mixture was refluxed for 48 h. The suspension was then cooled down to room temperature. The solvent was evaporated to dryness under reduced pressure. The solid residue was washed with water and extracted with $CH_2Cl_2$ (3×20 mL). The organic phases were collected and combined, dried over anhydrous $MgSO_4$ and evaporated under reduced pressure. The crude product was purified by column chromatography on silica gel using cyclohexane as eluent. After having eluted the first fraction which was the unreacted monobromide derivatives, the polarity of the eluent was gradually increased up to cyclohexane:ethyl acetate 50:50 (vol:vol) allowing to afford 50 mg of compound as a dark brown solid (yield 80%, 0.21 mmol). $3_c$: $^1$H NMR (400 MHz, 298 K, $CDCl_3$) δ (ppm): (400 MHz, 298 K, CDCl3) d (ppm): −3.84 (s, 3H), −3.83 (s, 3H), 1.72 (s, 9H), 1.64 (s, 9H), 7.77 (dd, 2H), 8.46 (s, 1H), 8.48 (s, 2H), 8.56 (m, 2H), 8.58 (s, 1H), 8.62 (s, 1H), 8.83 (dd, 2H). Exact mass: m/z: calcd for $C_{31}H_{35}N$ +H$^+$: 422.2841 [M+H$^+$], found: 422.2841. $3_o$: $^1$H NMR (400 MHz, 298 K, $CDCl_3$) δ (ppm): 1.19 (s, 9H), 1.25 (s, 9H), 1.47 (s, 3H), 1.50 (s, 3H), 6.40 (dd, 2H), 6.52 (d, 2H), 6.73 (br, 1H), 6.78 (br, 4H), 7.45 (dd, 2H).

2,7-di-tert-butyl-4-(N-methylpyridin-4-A-trans-10b,10c-dimethyl-10b,10c-dihydropyrene hexafluorophosphate

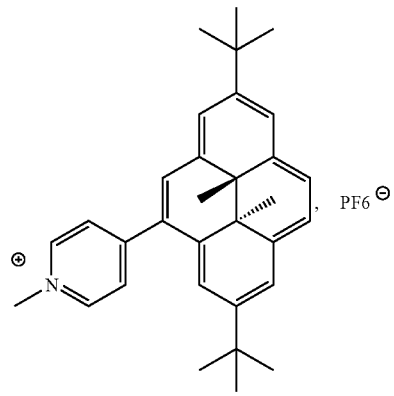

20 mg of 2,7-di-tert-butyl-4-(4-pyridyl)-trans-10b,10c-dimethyl-10b,10c-dihydropyrene (0.047 mmol) were dissolved in 20 mL diethyl ether. 1 mL of $CH_3I$ was then rapidly added and the solution was refluxed for 4 hours. Upon cooling down to room temperature, the precipitate formed (iodide salt) was filtered off, washed with diethyl ether and dissolved in 20 mL $CH_3OH$. The hexafluorophosphate salt was then precipitated upon addition of a saturated aqueous solution of $NH_4PF_6$. The orange powder was then collected by filtration, washed with cold water and dried under vacuum (yield 89%, 22 mg, 42 μmol). $^1$H NMR (500 MHz, 298 K, $CD_3CN$) δ (ppm): −3.88 (s, 3H), −3.84 (s, 3H), 1.65 (s, 9H), 1.70 (s, 9H), 4.39 (s, 3H), 8.43 (d, 2H), 8.61 (d, 1H), 8.63 (s, 1H), 8.65 (d, 1H), 8.71 (s, 1H), 8.73 (d, 2H), 8.77 (s, 1H), 8.78 (s, 1H), 8.80 (s, 1H). Exact mass: m/z: calcd for $C_{32}H_{38}N^+$: 436.2999 [M-PF$_6^-$], found: 436.2998. $^1$H NMR (500 MHz, 298 K, $CD_3CN$) δ (ppm): 1.20 (s, 9H), 1.25 (s, 9H), 1.41 (s, 3H), 1.48 (s, 3H), 4.23 (s, 3H), 6.45 (d, 1H), 6.49 (d, 1H), 6.56 (s, 1H), 6.90 (s, 1H), 6.94 (s, 1H), 6.94 (s, 1H), 7.29 (s, 1H), 8.03 (d, 2H), 8.44 (d, 2H).

Irradiation Procedures

Samples for experiments under inert atmosphere were prepared in a Jaram glove box with carefully degassed solvents, or were thoroughly purged with argon. Solutions for experiments in the presence of oxygen were prepared under air (1 atm). The solutions were irradiated in UV-visible quartz cells or NMR tubes. The concentration used for UV-visible spectroscopy and NMR experiments were comprised between $2\times10^{-5}$ M and $3\times10^{-3}$ M. The visible irradiations for making the isomerization of the "closed" 1 isomer to its corresponding "open" 2 were carried out with a Xe—Hg lamp, using a 630 nm cut-off filter and the samples were placed at 8° C. bath in order to limit the reverse thermal reaction. Samples were placed at a distance of 15 cm of the visible lamp. Alternatively, irradiation was performed at room temperature with a 150 W tungsten-halogen lamp equipped with a 590 nm cut-off filter. The conversions between the different species were investigated from UV-visible and NMR experiments. Intermediate spectra were recorded at different times depending on the isomerization processes rates. The ratio between the different species was determined by $^1$H-NMR from the relative integration of the characteristic resonance peaks of the $N^+$—$CH_3$ groups of the different forms.

4.28 (s, 3H), 6.51 (s, 1H), 7.00 (s, 1H), 7.06 (d, J=2.1 Hz, 1H), 7.22 (d, J=2.1 Hz, 1H), 7.42 (d, J=2.1 Hz, 1H) 7.64 (s, 1H) 7.88 (d, J=7.0 Hz, 2H), 8.07 (d, J=7.0 Hz, 2H), 8.49 (d, J=7.0 Hz, 2H), 8.54 (3=7.0 Hz, 2H). Mass (m/z): calcd: 705.3 [M-$PF_6^-$], found: 705.3.

Example 5: Phosphorescence Measurements

Luminescence measurements in the near infrared (NIR) region were performed with an Edinburgh Instruments FLS-920 spectrometer equipped with a germanium detector cooled with liquid nitrogen. The luminescence was recorded on air-equilibrated $CD_3CN$ solutions contained in 3-mL quartz cells with 1-cm path length. Deuterated acetonitrile was used as the solvent to increase the sensitivity of the measurement, owing to the significantly higher emission quantum yield of singlet oxygen in comparison with $CH_3CN$. Compound 3 was generated in situ by exhaustive irradiation of 1 in the visible region (ca. 60 min irradiation under the conditions employed) at room temperature. The solution was then warmed up at 60° C. and its luminescence properties (spectral dispersion and time dependence of the intensity) were monitored in the absence of photoexcitation (the excitation source of the spectrometer was turned off).

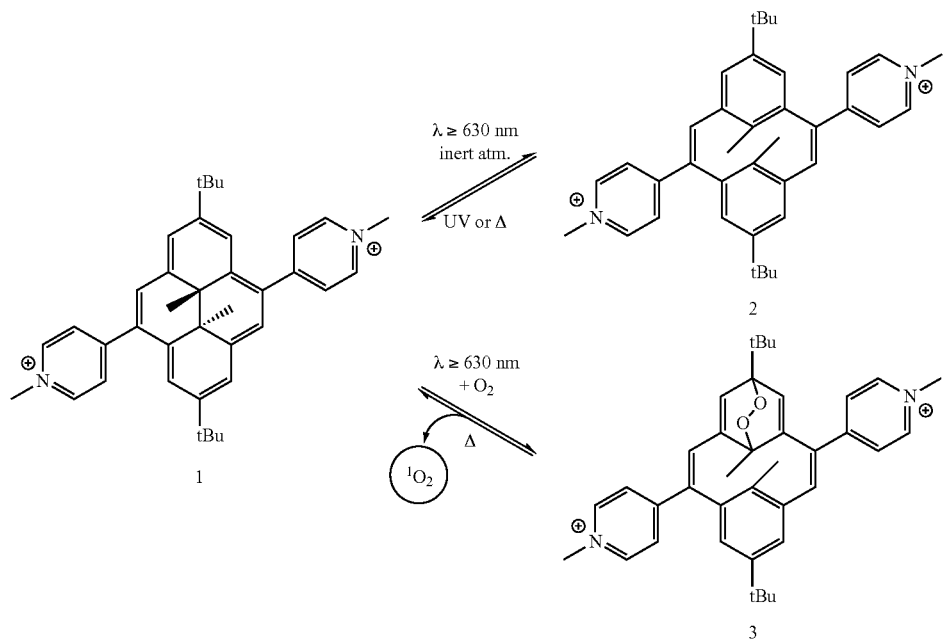

Example 3: Synthesis of Compound 2

2 was generated by visible irradiation of a solution of 1 under inert following the procedure described above.

2: $^1$H NMR (500 MHz, 298 K, $CD_3CN$) δ (ppm): 1.20 (s, 18H), 1.50 (s, 6H), 4.26 (s, 6H), 6.69 (s, 4H), 7.12 (s, 2H), 7.37 (s, 2H), 8.06 (m, 4H), 8.49 (m, 4H). Mass (m/z): calcd: 673.3 [M-$PF_6^-$], found: 673.3.

Example 4: Synthesis of Compound 3

3 was generated by visible irradiation of a solution of 1 under air following the procedure described above.

3: $^1$H NMR (500 MHz, 298 K, $CD_3CN$) δ (ppm): −0.05 (s, 3H), 1.04 (s, 9H), 1.24 (s, 9H), 2.07 (s, 3H), 4.24 (s, 3H), Example 6: $^1$H NMR Analysis of Singlet Oxygen Trapping Singlet oxygen trapping experiments were carried out by NMR using 2,3-dimethyl-2-butene.

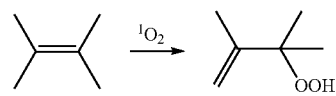

A solution of 1 (3 mM) in $CD_3CN$ was irradiated (λ>630 nm) and converted into 3. A 30 fold excess (90 mM) of 2,3-dimethyl-2-butene was added to the solution and the sample was maintained at 35° C. in the dark. After 48 h, a ¹H NMR spectra was acquired with simultaneous saturation of the large signal at 1.8 ppm due to unreacted 2,3-dimethyl-2-butene. The two olefin proton signals for trapped hydroperoxide appear in the open window of 4.88-4.93 ppm. Comparison of the average peak integrals with signals of regenerated 1 showed that 85±10% of the released singlet oxygen was trapped (FIG. 5).

Example 7: Evidence of Singlet Oxygen Production by Trapping ESR Experiments

Singlet oxygen trapping experiments were carried out by ESR using 2,2,6,6-tetramethyl-4-piperidone, TEMPD (Hideg et al. *Biochim. Biophys. Acta* 2011, 1807, 1658-1661).

A solution of 1 (44 µM) with TEMPD (1M) in CH₃CN was irradiated (λ>630 nm) and converted into 3. ESR spectra were recorded before and after irradiation process (FIG. 6). The sample was then heated in the dark to release singlet oxygen.

Example 8: In Vitro Experiments

Compounds of formula I-3 are incubated in the presence of cells and cell viability is observed by microscopy after heating 48 h at 37° C.

Compounds of formula I-1 are incubated in the presence of cells and cell viability is observed:
  after heating 48 h at 37° C. (control); or
  after irradiation at λ≥630 nm in presence of oxygen, and then heating 48 h at 37° C.

Compounds of formula I-2 are incubated in the presence of cells and cell viability is observed:
  after heating 48 h at 37° C. (control); or
  after contacting said compounds of formula I-2 with singlet oxygen, said singlet oxygen being generated beforehand or in situ, in presence of an external photosensitizer and oxygen or an oxygen containing gas, and then heating 48 h at 37° C.

Example 9: Preparation of Complex 5

The homodetic cyclopeptide Raft(4GRD)CysNPys was synthesized according to the FR 02 11614 patent.

Synthesis of the DHP-SH

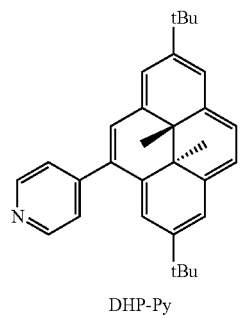

DHP-Py

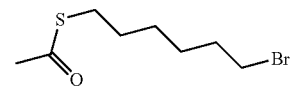

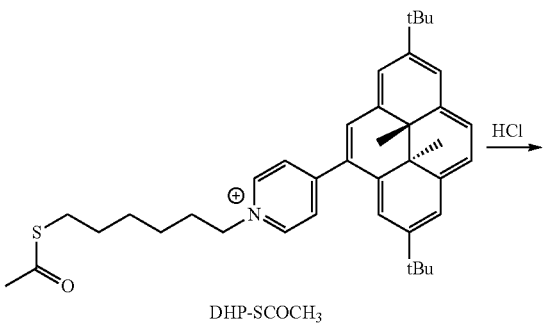

DHP-SCOCH₃

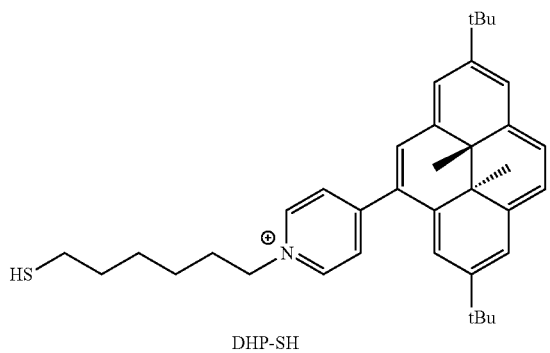

DHP-SH

Synthesis of DHP-SCOCH₃

DHP-Py (45 mg/0.1 mmol) and 3 equivalents of bromothioacetatealkyl A (85 mg/0.3 mmol) are dissolved in 20 mL of CH₃CN. The solution is then refluxed during one week under inert atmosphere. Upon cooling, the solution is then concentrated under vacuum and the product (DHP-SCOCH₃) is precipitated by addition of diethyl ether. The red-brown solid is filtered, washed with diethyl ether and dried under vacuum. Yield: 76%.

Synthesis of DHP-SH

The protected compound DHP-SCOCH₃ (20 mg/0.03 mmol) is dissolved in MeOH (2 mL) and conc. HCl (0.5 mL) under inert atmosphere and the mixture is then refluxed for 3 hours. Upon cooling, solvents are removed under vacuum to afford the deprotected compound DHP-SH in quantitative yield. This product can be used without further purifications.

Vectorization

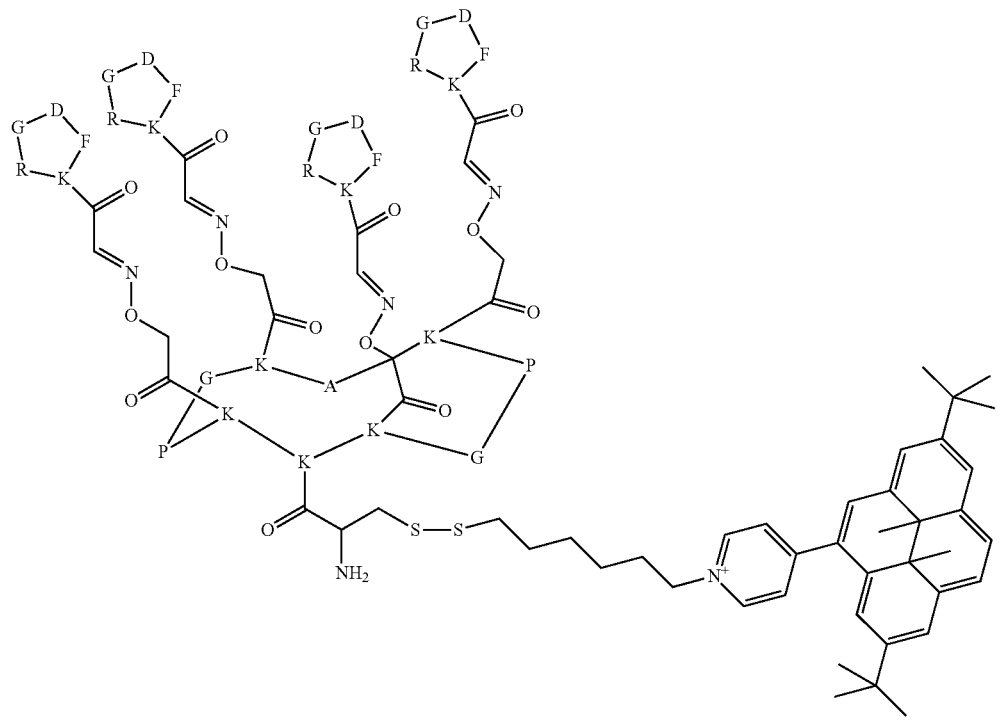

10 mg of Raft(4RGD)CysNPyS (2.41 μmol, 1 eq.) in 600 μL of DMF/H$_2$O/CH$_3$CN (1/1/1) are submitted to three empty/Argon cycles. The DHP-SH (3 mg, 4.82 μmol, 2 eq.) is dissolved in 600 μL of CH$_3$CN/Acetate buffer (pH=5.2, 100 mM) (2/1). This solution is protected from light and submitted to 3 empty/Argon cycles. The Raft(4RGD)Cys-NPyS and DHP-SH solutions are mixed and protected from light. After three empty/Argon cycles, the reaction mixture is stirred 2 h at room temperature. The crude is purified by RP-HPLC to afford the final product 5 as a brown powder (1.5 mg, 332 nmol) Yield: 14%; RP-HPLC: RT=17 min (gradient 10% to 85% CH$_3$CN in 20 min; column 100-7 C18, 214 nm). MS: calcd for $C_{211}H_{304}N_{57}O_{51}S_2$ MW 4519.25 g.mol$^{-1}$. Found MW=4518.4 g.mol$^{-1}$.

Irradiation (According to the General Procedure):

The visible irradiation induces the isomerization of the "closed" 5 isomer to its corresponding "open" form 6 when performed in the absence of oxygen. In the presence of oxygen, the visible irradiation of the "closed" isomer 5 produces the corresponding endoperoxide "open" form 7.

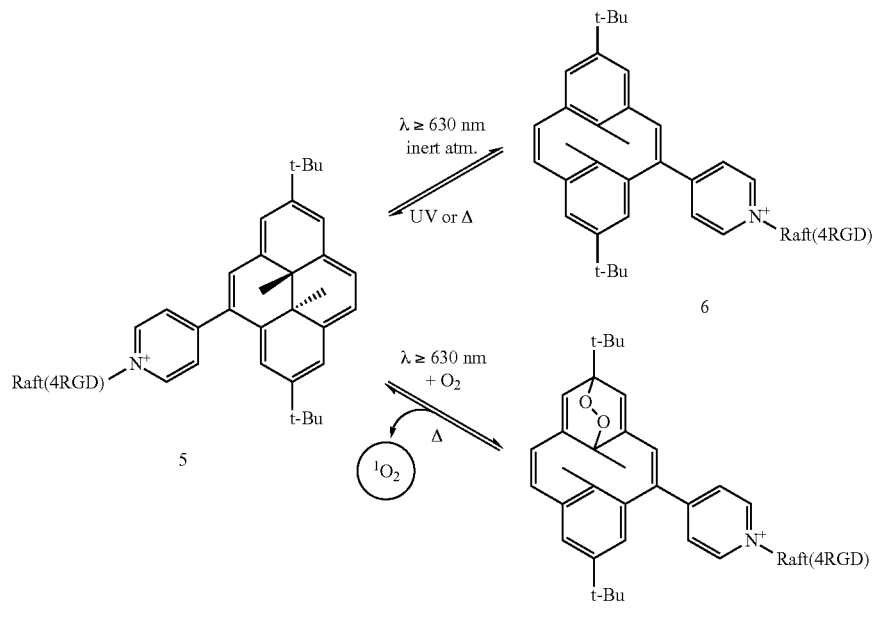

Example 10: Evaluation of the Cytotoxicity of Complex 5

The ability of complex 5 to induce the death of cancerous cells under near infrared irradiation has been evaluated on human ovarian adenocarcinoma IGROV1, using the MTT test. IGROV1 cells were cultivated in a 10% SVF supplemented RPMI-1640 medium and incubated at 37° C. under a 5% $CO_2$ atmosphere.

The cells were seeded on a 96-well plate with a density of 5000 cells per well. Twenty four hours later, the culture medium was removed and replaced by a fresh medium containing different concentrations of complex 5 comprised from 1 to 100 μm (n=3 wells per conditions). The culture plates were irradiated with a 2.4 $mW/cm^2$ 680 nm laser for 85 minutes at 37° C. 48 hours later, the cytotoxicity is determined using a MTT test provided by Sigma-Aldrich (3-(4,5-di-methylthiazol-2-yl)-2,5-diphenyltetrazolium bromide). The MTT solution (0.2 mg/mL in PBS) is added to the wells (100 μL/well) and the plates were incubated 2 hours at 37° C. Formazan crystals that Mimed were then dissolved with 100 μL/well propanol and the absorbance at 570 nm was read on an absorbance reader (AD 340, Beckman counter). The results are expressed in percentage of the mean value obtained with the untreated wells (FIG. 7).

This cellular culture experiment highlights the capacity of complex 5 to induce the death of cancerous cells under a near infrared irradiation. At a 50 μM concentration, the death of 50% of the cells is observed.

Example 11: Ability to Target the Cancerous Cells

The ability of compounds 4 and 5 to cross the ovarian adenocarcinoma cell (IGROV1) membrane or to fix the cell membrane of these cells were evaluated by flow cytometry. The cells were seeded in Petri dishes at a $10^6$ density of cells per dish. Twenty four hours later, the culture medium was removed and replaced by a fresh medium containing compound 4 or compound 5 at a 50 μM concentration. After 2 hours of incubation at 37° C., the cells were rinsed with PBS, trypsinized, centrifuged and then suspended with a concentration of $10^6$ cells per mL of PBS. The fluorescence of the cells was observed with a flow cytometer (Accuri C6, BD) at a 488 nm excitation wavelength and with a 680 nm high-pass emission filter.

FIG. 8 presents the results of the flow cytometry analysis, showing the significative enhancement of the ability of complex 5 to cross or to fix the cell membrane compared to its "unvectorized" analog compound 4.

Example 12: In Vitro Experiments with Complex of Formula II

Experiments according to example 8 are conducted on other cancer cell lines and especially cancers in which the targeting of the avJ33 integrin is relevant such as melanoma, glioblastoma and other human ovarian cancer cell lines, particularly solid tumors.

Example 13: In Vivo Experiments with Compounds of Formula I and Complexes of Formula II In vivo therapeutic potential is evaluated by pre-clinical studies on cancer of mouse models and, in particular, cancers for which the RAFT(4RGD) group is a specific targeting moiety such as ovarian cancer, breast cancer, brain cancer, upper airways tract cancer, lung cancer, liver cancer, colon cancer, prostate cancer, bone cancer and their respective metastases.

A/ In Vivo Biodistribution Study of Compounds of Formula I-1 and Complexes of Formula II-1.

Compounds of formula I-1 and II-1 are administered intravenously or intraperitoneally to tumor-bearing animals (the above mentioned mouse models) and their biodistribution and pharmacokinetics are studied by non-invasive fluorescence imaging in the near infrared region using a Fluobeam700 apparatus (Fluoptics).

From this study, the post-injection time at which the best signal-to-noise ratio is obtained is evaluated, corresponding to the photodynamic activation optimum of the compounds of formula I-1 and II-1 for a therapeutic use.

B/ In Vivo Therapeutic Efficiency of the Compounds of Formula I-1 and II-1

Compounds of formula I-1 and II-1 are administered intravenously or intraperitoneally to tumor-bearing animals (the above mentioned mouse models). At the post-injection time previously determined, the animals are submitted to fluorescence imaging (Fluobeam700; Fluoptics) to identify the tumors, non-invasively in the case of superficial tumors or intraoperatively for deeper tumors. The identified tumors are then irradiated by a near infrared laser (100-300 $mW/cm^2$).

In the non-invasive approach, the laser activation is optionally reproduced several times, and optionally preceded by a new injection of the compound.

The therapeutic efficiency is evaluated by non-invasive diagnostic imaging measuring the tumor regression (bioluminescence, microCT, MRI, PET) and by the study of the survival curves of the animal models compared to untreated animals (control).

In another attempt, the photodynamic treatment is done after a surgical tumor excision to get rid of the invisible tumor residues or tumor residues placed in a region where the surgical resection is impossible because of their close proximity to vital organs.

The invention claimed is:
1. A method for treating pathologies sensitive to singlet oxygen, in particular for phototherapy and/or for treating cancers comprising administering to a subject in need thereof a compound of the following formula I

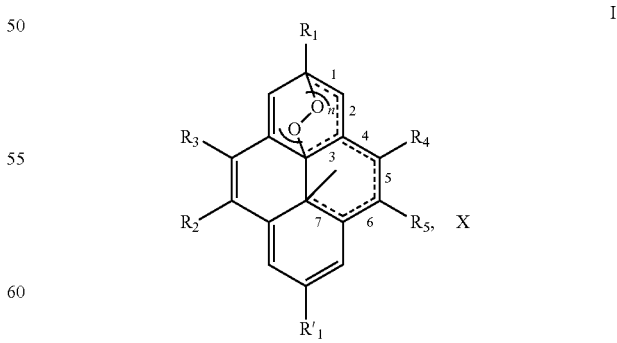

wherein:
n represents 0 or 1,
---- represents a single bond or no bond,
═ represents a single or a double bond, $R_1$ and $R'_1$ represent independently from each other:

H, a linear or branched $(C_1\text{-}C_{18})$-alkyl, a $(C_3\text{-}C_8)$-cycloalkyl,

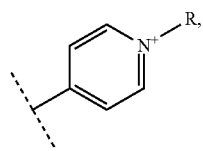

—$N(R)_3^+$,

R representing:

H, a linear or branched $(C_1\text{-}C_{18})$-alkyl, a $(C_3\text{-}C_8)$-cycloalkyl, $R_2$, $R_3$, $R_4$ and $R_5$ represent independently from each other:

H, a linear or branched $(C_1\text{-}C_{18})$-alkyl, a $(C_3\text{-}C_8)$-cycloalkyl,

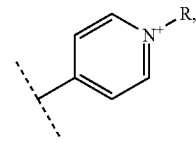

—$N(R)_3^+$,

R representing:

H, a linear or branched $(C_1\text{-}C_{18})$-alkyl, a $(C_3\text{-}C_8)$-cycloalkyl, X represents one or more physiologically acceptable counter anion(s), providing that:

at least one of $R_1$, $R'_1$, $R_2$, $R_3$, $R_4$ and $R_5$ represents one of the following groups:

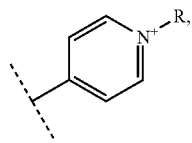

or

—$N(R)_3^+$, n, ---- and the bonds 1 to 7 are such as:

n=0, ---- represents a single bond, bonds 1, 4 and 6 represent a double bond, and bonds 2, 3, 5 and 7 represent a single bond, or n=0, ---- represents no bond, bonds 1, 3, 5 and 7 represent a double bond, and bonds 2, 4 and 6 represent a single bond, or n=1, ---- represents no bond, bonds 2, 5 and 7 represent a double bond, and bonds 1, 3, 4 and 6 represent a single bond.

2. The method according to claim 1 wherein:

$R_1$ and $R'_1$ are identical;

$R_1$ and/or $R'_1$ represent(s) a linear or branched $(C_1\text{-}C_{18})$-alkyl, in particular a tert-butyl;

$R_2$ and/or $R_4$ represent(s)

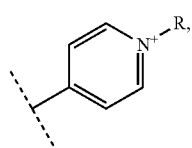

$R_3$ and $R_5$ representing in particular H;

$R_3$ and/or $R_5$ represent(s)

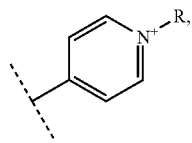

$R_2$ and $R_4$ representing in particular H; or

X is (are) chosen from the group consisting in Cl$^-$, PF$_6^-$, BF$_4^-$, CH$_3$COO$^-$, Br$^-$, F$^-$, SO$_4^{2-}$, HSO$_4^-$, HPO$_4^{2-}$, H$_2$PO$_4^-$; or R represents a linear or branched $(C_1\text{-}C_{18})$-alkyl, in particular —CH$_3$.

3. The method according to claim 1 wherein the compound is one of the compound of the following formulae:

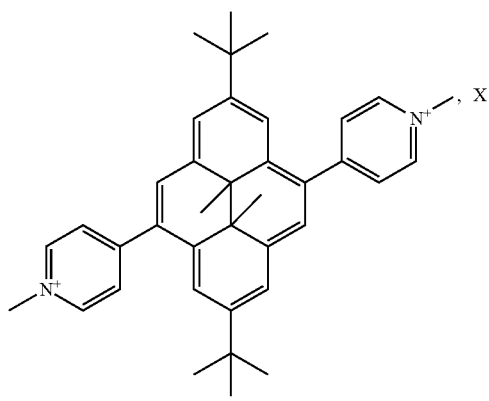

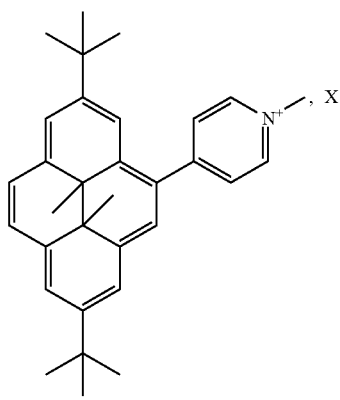
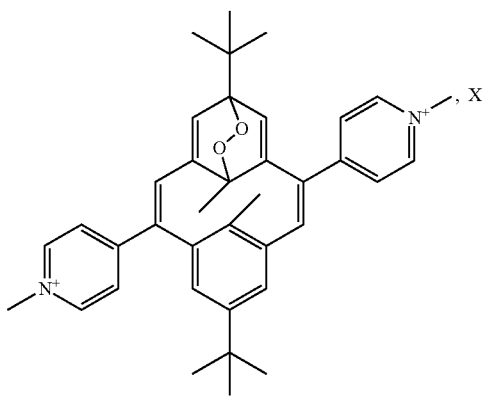
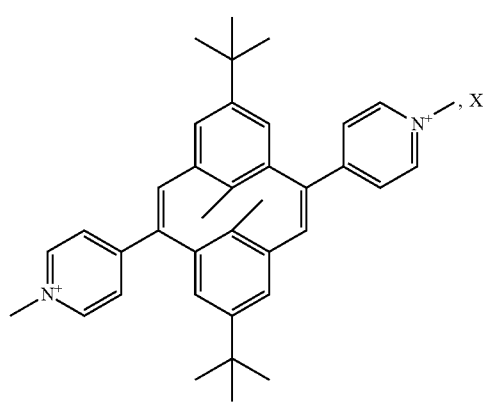
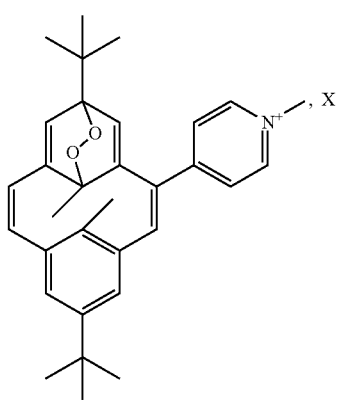
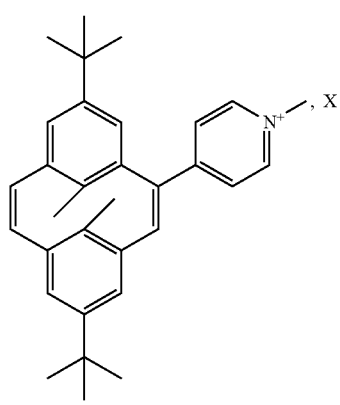
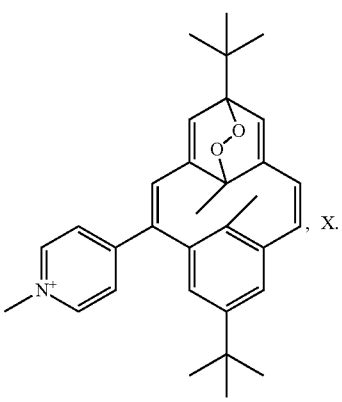
4. The method according to claim 1, wherein the compound of formula I forms a complex of the following formula II

II

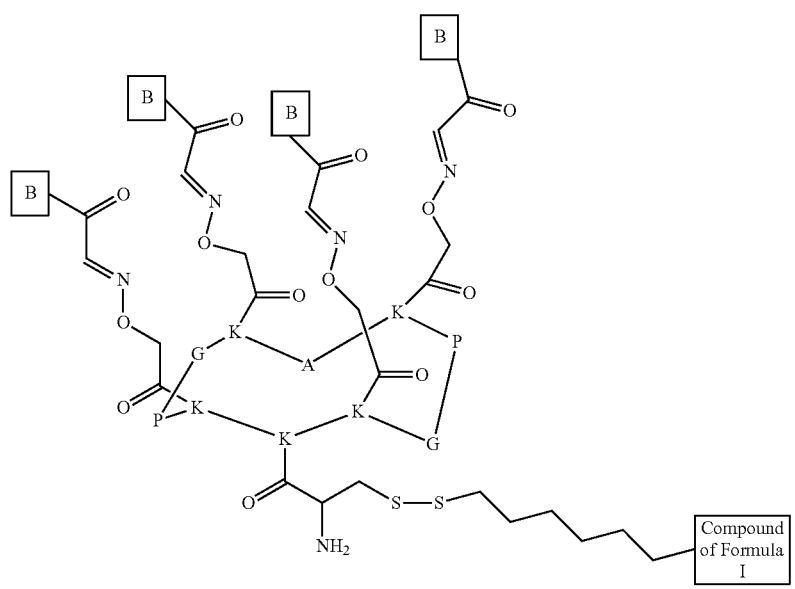

B group being chosen from a peptide or an acid residue selected from a hyaluronic acid or a folic acid.

5. A pharmaceutical or diagnostic composition comprising a compound of formula I according to claim 1 as active agent and a pharmaceutically acceptable vehicle.

6. Compound of the following formula I (bis)

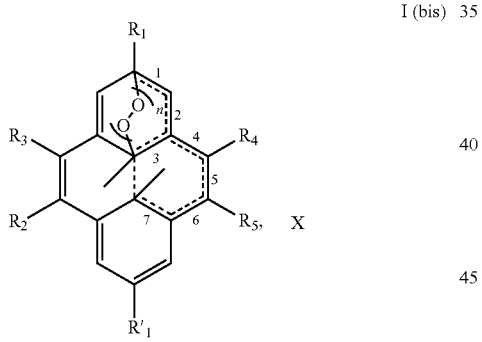

I (bis)

wherein:
n is 1,
----- represents a single bond or no bond,
═ represents a single or a double bond,
$R_1$ and $R'_1$ represent independently from each other:
H,
a linear or branched $(C_1-C_{18})$-alkyl,
a $(C_3-C_8)$-cycloalkyl,

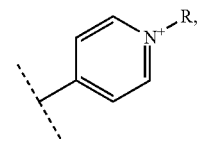

—$N(R)_3^+$,

R representing:
H,
a linear or branched $(C_1-C_{18})$-alkyl,
a $(C_3-C_8)$-cycloalkyl,
$R_2$, $R_3$, $R_4$ and $R_5$ represent independently from each other:
H,
a linear or branched $(C_1-C_{18})$-alkyl,
a $(C_3-C_8)$-cycloalkyl,

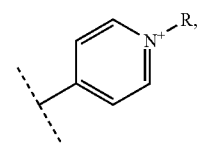

—$N(R)_3^+$,
R representing:
H,
a linear or branched $(C_1-C_{18})$-alkyl,
a $(C_3-C_8)$-cycloalkyl,
X represents one or more counter anion(s), in particular one or more physiologically acceptable counter anion(s),
providing that:
at least one of $R_1$, $R'_1$, $R_2$, $R_3$, $R_4$ and $R_5$ represents one of the following groups:

or
—$N(R)_3^+$, n, ---- and the bonds 1 to 7 are such as:
- n=1, ---- represents no bond, bonds 2, 5 and 7 represent a double bond, and bonds 1, 3, 4 and 6 represent a single bond.

7. Compound according to claim 6, wherein:
- $R_1$ and $R'_1$ are identical;
- $R_1$ and/or $R'_1$ represent(s) a linear or branched ($C_1$-$C_{18}$)-alkyl, in particular a tert-butyl;
- $R_2$ and/or $R_4$ represent(s)

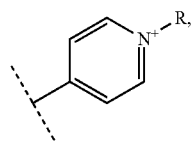

$R_3$ and $R_5$ representing in particular H;
- $R_3$ and/or $R_5$ represent(s)

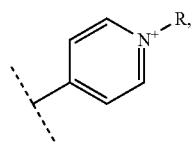

$R_2$ and $R_4$ representing in particular H;
- X is (are) chosen from the group consisting in Cl⁻, $PF_6^-$, $BF_4^-$, $CH_3COO^-$, Br⁻, F⁻, $SO_4^{2-}$, $HSO_4^-$, $HPO_4^{2-}$, $H_2PO_4^-$; or
- R represents a linear or branched ($C_1$-$C_{18}$)-alkyl, in particular —$CH_3$.

8. Compound according to claim 7, of one of the following formulae:

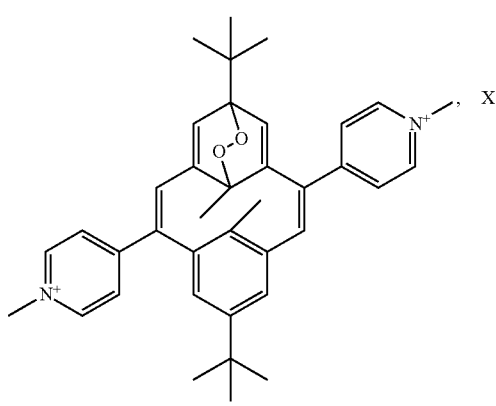

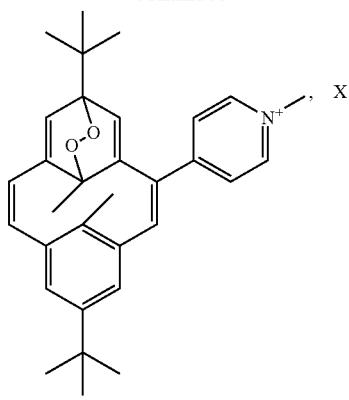

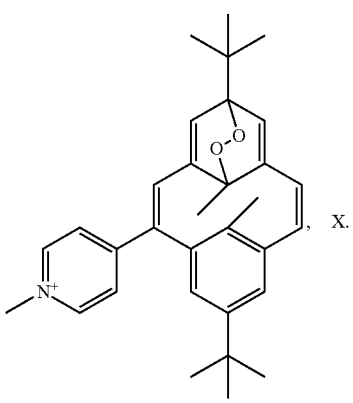

9. A pharmaceutical or diagnostic composition comprising a compound of formula I according to claim 1 as active agent and a pharmaceutically acceptable vehicle.

10. A pharmaceutical or diagnostic composition comprising a compound of formula I according to claim 2 as active agent and a pharmaceutically acceptable vehicle.

11. A pharmaceutical or diagnostic composition comprising a compound of formula I according to claim 3 as active agent and a pharmaceutically acceptable vehicle.

12. A pharmaceutical or diagnostic composition comprising a complex of formula II according to claim 4 as active agent and a pharmaceutically acceptable vehicle.

13. The method according to claim 4, wherein the B group is a peptide of the following formula:

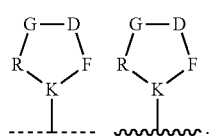

14. A compound of the following formula I (bis)

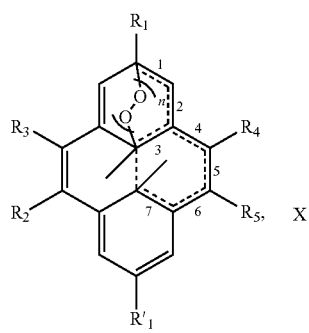

wherein:
n represents 0 or 1,
---- represents a single bond or no bond,
== represents a single or a double bond,
$R_1$ and $R'_1$ represent independently from each other:
H,
a linear or branched $(C_1-C_{18})$-alkyl,
a $(C_3-C_8)$-cycloalkyl,

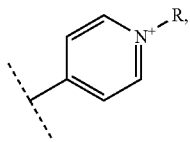

—$N(R)_3^+$,
R representing:
H,
a linear or branched $(C_1-C_{18})$-alkyl,
a $(C_3-C_8)$-cycloalkyl,
$R_2$, $R_3$, $R_4$ and $R_5$ represent independently from each other:
H,
a linear or branched $(C_1-C_{18})$-alkyl,
a $(C_3-C_8)$-cycloalkyl,

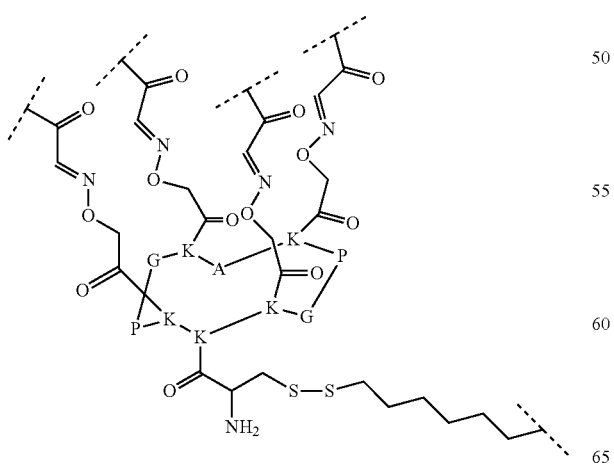

—$N(R)_3^+$,
R representing:
H,
a linear or branched $(C_1-C_{18})$-alkyl,
a $(C_3-C_8)$-cycloalkyl,
X represents one or more counter anion(s), in particular one or more physiologically acceptable counter anion(s),
providing that:
at least one of $R_1$, $R'_1$, $R_2$, $R_3$, $R_4$ and $R_5$ represents one of the following groups:

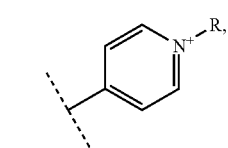

or
—$N(R)_3^+$,
n, ---- and the bonds 1 to 7 are such as:
n=0, ---- represents a single bond, bonds 1, 4 and 6 represent a double bond, and bonds 2, 3, 5 and 7 represent a single bond, or
n=0, ---- represents no bond, bonds 1, 3, 5 and 7 represent a double bond, and bonds 2, 4 and 6 represent a single bond, or
n=1, ---- represents no bond, bonds 2, 5 and 7 represent a double bond, and bonds 1, 3, 4 and 6 represent a single bond,
when n=0, $R_1$ and/or $R'_1$ are different from one of the following groups:

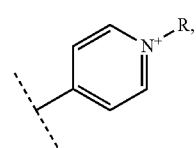

or
—$N(R)_3^+$,
wherein the compound of formula I(bis) forms a complex of the following formula II(bis)

II(bis)

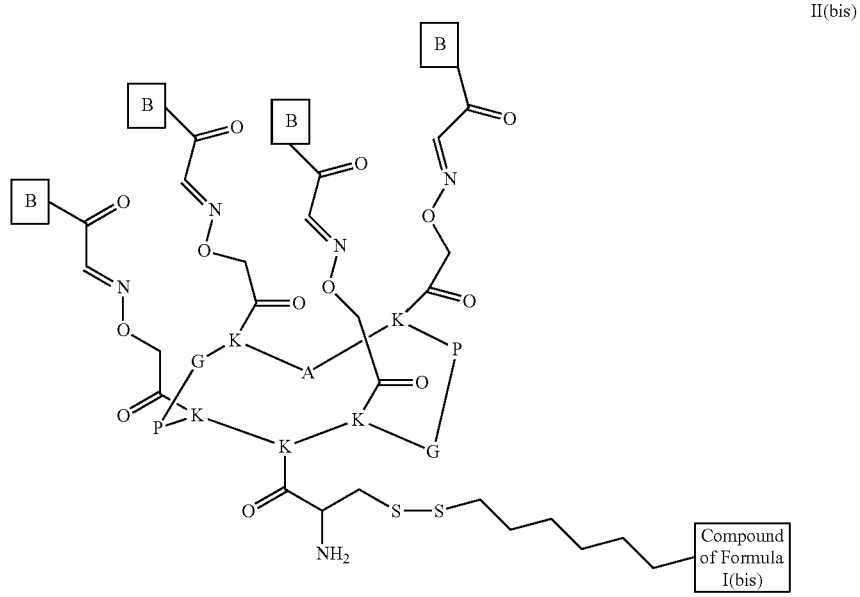

II (bis)

B group being chosen from a peptide or an acid residue selected from a hyaluronic acid or a folic acid.

15. The compound according to claim 14, wherein:

$R_1$ and $R'_1$ are identical;

$R_1$ and/or $R'_1$ represent(s) a linear or branched $(C_1-C_{18})$-alkyl, in particular a tert-butyl;

$R_2$ and/or $R_4$ represent(s)

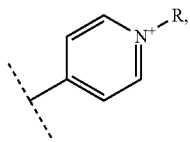

$R_3$ and $R_5$ representing in particular H;

$R_3$ and/or $R_5$ represent(s)

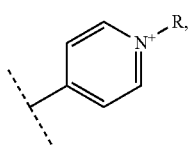

$R_2$ and $R_4$ representing in particular H;

X is (are) chosen from the group consisting in $Cl^-$, $PF_6^-$, $BF_4^-$, $CH_3COO^-$, $Br^-$, $F^-$, $SO_4^{2-}$, $HSO_4^-$, $HPO_4^{2-}$, $H_2PO_4^-$; or R represents a linear or branched $(C_1-C_{18})$-alkyl, in particular —$CH_3$.

16. The compound according to claim 14, of one of the following formulae:

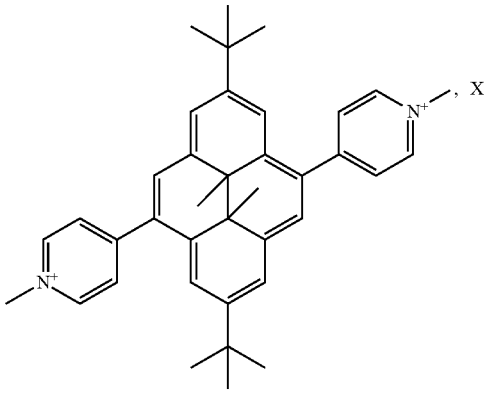

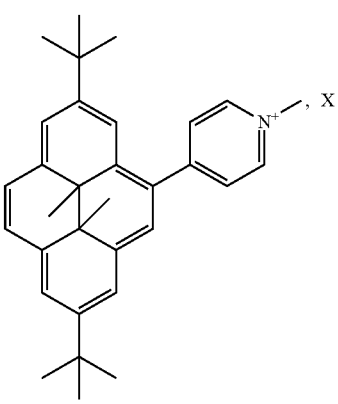

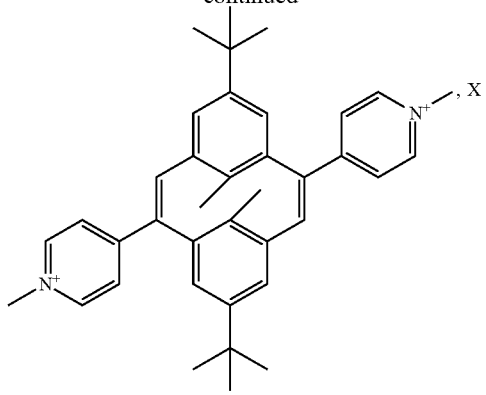
17. The compound according to claim 14, wherein the B group is a peptide of the following formula:
* * * * *